(12) United States Patent
Thanou et al.

(10) Patent No.: US 11,786,468 B2
(45) Date of Patent: Oct. 17, 2023

(54) NANOPARTICLES

(71) Applicant: KING'S COLLEGE LONDON, London (GB)

(72) Inventors: Maria Thanou, London (GB); Michael James Lee Wright, London (GB); Miguel Centelles, London (GB); Andrew David Miller, London (GB); Wladyslaw Gedroyc, London (GB)

(73) Assignee: KING'S COLLEGE LONDON, London (GB)

( * ) Notice: Subject to any disclaimer, the term of this patent is extended or adjusted under 35 U.S.C. 154(b) by 430 days.

(21) Appl. No.: 15/580,189

(22) PCT Filed: Jun. 8, 2016

(86) PCT No.: PCT/GB2016/051693
§ 371 (c)(1),
(2) Date: Dec. 6, 2017

(87) PCT Pub. No.: WO2016/198862
PCT Pub. Date: Dec. 15, 2016

(65) Prior Publication Data
US 2018/0177728 A1   Jun. 28, 2018

(30) Foreign Application Priority Data

Jun. 8, 2015 (GB) .................................... 1509934

(51) Int. Cl.
| | | |
|---|---|---|
| *A61K 9/127* | (2006.01) | |
| *A61K 49/08* | (2006.01) | |
| *A61K 31/4745* | (2006.01) | |
| *A61K 31/704* | (2006.01) | |
| *A61K 49/10* | (2006.01) | |
| *A61K 49/18* | (2006.01) | |
| *A61K 41/00* | (2020.01) | |

(52) U.S. Cl.
CPC ........ *A61K 9/1272* (2013.01); *A61K 31/4745* (2013.01); *A61K 31/704* (2013.01); *A61K 41/0052* (2013.01); *A61K 49/085* (2013.01); *A61K 49/106* (2013.01); *A61K 49/1812* (2013.01); *A61K 49/1839* (2013.01)

(58) Field of Classification Search
CPC ............ A61K 41/0052; A61K 49/1812; A61K 31/4745; A61K 31/704; A61K 9/1272; A61K 9/085; A61K 49/106; A61K 49/1839
See application file for complete search history.

(56) References Cited

U.S. PATENT DOCUMENTS

| | | | | |
|---|---|---|---|---|
| 2002/0102298 A1* | 8/2002 | Needham | ............... | A61K 9/127 424/450 |
| 2011/0020239 A1* | 1/2011 | Bulte | ................. | A61K 49/0002 424/9.6 |
| 2011/0270151 A1 | 11/2011 | Li | | |
| 2012/0100079 A1* | 4/2012 | Burdinski | ............ | A61K 9/0009 424/9.321 |
| 2013/0129636 A1* | 5/2013 | Kamaly | ............. | A61K 49/1812 424/9.321 |
| 2013/0230457 A1 | 9/2013 | Reed et al. | | |

FOREIGN PATENT DOCUMENTS

| | | |
|---|---|---|
| EP | 2229182 A2 | 9/2010 |
| WO | 2010/094043 A2 | 8/2010 |

(Continued)

OTHER PUBLICATIONS

Ahmed N, et al., Theranostic applications of nanoparticles in cancer Drug Discov Today. 2012;17(17-18):928-34. Epub Apr. 10, 2012.

(Continued)

*Primary Examiner* — Michael G. Hartley
*Assistant Examiner* — Leah H Schlientz
(74) *Attorney, Agent, or Firm* — MH2 TECHNOLOGY LAW GROUP, LLP

(57) ABSTRACT

The invention provides a (drug-containing) lipid nanoparticle with:
(i) at least one phospholipid;
(ii) at least one lysolipid; and
(iii) at least one phospholipid comprising a hydrophilic polymer; and
(iv) at least one structural lipid of formula (I) which has the following general structure:

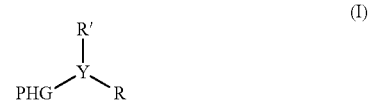

(I)

wherein R and R' are long hydrocarbyl hydrophobic chains, Y is a linker element, and PHG is a polar head group described as large according to its van der Waals radius, and which is different from the phospholipid (i). The lipid nanoparticle can release a drug (or API) from within the lipid nanoparticle as a result of focused ultrasound (FUS) applied continuously, at least twice, to a desired part of the body to induce hyperthermia (an increase in temperature). FUS is applied after the lipid nanoparticle containing the drug has been administered to the live subject, and causes controlled release of the drug at the desired site of the body. Ultrasound is then halted, and the site of interest allowed to cool. Ultrasound is then applied again. Lipid nanoparticles can be labelled (for MRI, NIRF imaging), enabling real time monitoring of the drug in the human body. Imaging information can be used to direct and guide the nature of the FUS applied to the site of interest.

16 Claims, 28 Drawing Sheets

(56) References Cited

FOREIGN PATENT DOCUMENTS

| WO | 2011/061541 A1 | 5/2011 |
|---|---|---|
| WO | 2012/139080 A2 | 10/2012 |
| WO | 2013/123407 A1 | 8/2013 |
| WO | 2014/037498 A2 | 3/2014 |

OTHER PUBLICATIONS

Bijman MN, et al., Inhibition of functional her family members increases the sensitivity to docetaxel in human ovarian cancer cell lines. Anticancer Drugs 2009;20:450-460.

Chakraborty AK, Mehra R, Digiovanna MP. Co-targeting erand her family receptors induces apoptosis in her2-normal or overexpressing breast cancer models. Anticancer Res 2015;35:1243-1250.

Chen Q, et al., Nanoscale theranostics for physical stimulus-responsive cancer therapies Biomaterials 2015;73:214-230.

Cohen R, et al., Inert coupling of irdye800cw and zirconium-89 to monoclonal antibodies for single- or dual-mode fluorescence and pet imaging. Nat Protoc 2013;8:1010-1018.

Cuadros M, Villegas R. Systematic review of her2 breast cancer testing. Appl Immunohistochem Mol Morphol 2009;17:1-7.

Datta NR, et al., Local hyperthermia combined with radiotherapy and-for chemotherapy: Recent advances and promises for the future. Cancer Treat Rev 2015;41:742-753.

De Goeij BE, Lambert JM. New developments for antibody-drug conjugate-based therapeutic approaches. Curr Opin Immunol 2016;40:14-23.

De Jong M, Essers J, van Weerden WM. Imaging preclinical tumour models: Improving translational power. Nat Rev Cancer 2014;14:481-493.

Dromi S, et al., Pulsed-high intensity focused ultrasound and low temperature-sensitive liposomes for enhanced targeted drug delivery and antitumor effect Clin Cancer Res. 2007;13(9):2722-7. Epub May 3, 2007.

Ebbini ES, ter Haar G. Ultrasound-guided therapeutic focused ultrasound: Current status and future directions. Int J Hyperthermia 2015;31:77-89.

Eberhard A,, et al., Heterogeneity of angiogenesis and blood vessel maturation in human tumors: implications for antiangiogenic tumor therapies. Cancer Res. 2000;60(5):1388-93. Epub Mar. 23, 2000.

Escoffre JM, et al., Mild hyperthermia influence on herceptin((r)) properties. Radiol Oncol 2015;49:41-49.

Etrych T, et al., Fluorescence optical imaging in anticancer drug delivery. J Control Release 2016;226:168-181.

Fleuren ED, et al., Theranostic applications of antibodies in oncology. Mol Oncol 2014;8:799-812.

Frazier N, Ghandehari H, Hyperthermia approaches for enhanced delivery of nanomedicines to solid tumors. Biotechnology and Bioengineering, May 20, 2015. doi: 10.1002/bit.25653 [Epub ahead of print].

Frenkel et al, Acad. Radiol. 2006;469-479, Delivery of Doxil in Breast cancer (investigation Tumour Model by pulsed HIFU).

Gasselhuber, Astrid, et al., Targeted drug delivery by high intensity focused ultrasound mediated hyperthermia combined with temperature-sensitive liposomes: Computational modelling and preliminary in vivovalidation, International Journal of Hyperthermia (2012), 28(4), 337-348.

Hauck ML, et al., Phase I trial of doxorubicin-containing low temperature sensitive liposomes in spontaneous canine tumors. Clin Cancer Res. 2006;12(13):4004-10. Epub Jul. 5, 2006.

Hijnen N, Langereis S, Grull H. Magnetic resonance guided high-intensity focused ultrasound for image-guided temperature-induced drug delivery. Adv Drug Deliv Rev 2014;72:65-81.

Horsman MR. Tissue physiology and the response to heat. Int J Hyperthermia. 2006;22(3):197-203. Epub Jun. 7, 2006.

http://ferraralab.bme.ucdavis.edu/research/.

Huang H, et al., Comparison of computed tomography- and optical image-based assessment of liposome distribution. Mol Imaging. 2013;12(3):148-60. Epub Mar. 16, 2013.

Janib SM, et al., Imaging and drug delivery using theranostic nanoparticles. Adv Drug Deliv Rev. 2010;62(11):1052-63. Epub Aug. 17, 2010.

Kamaly N et al. Imaging of Gadolinium Spatial Distribution in Tumor Tissue by Laser Ablation Inductively Coupled Plasma Mass Spectrometry Molecular Imaging and Biology, vol. 12, 2010, pp. 361-366.

Kamaly N, et al., A novel bimodal lipidic contrast agent for cellular labelling and tumour MRI. Org Biomol Chem. 2010;8(1):201-11.

Kamaly N, et al., Bimodal paramagnetic and fluorescent liposomes for cellular and tumor magnetic resonance imaging. Bioconjug Chem. 2008;19(1):118-29. Epub Nov. 8, 2007.

Kamaly N, et al., Folate receptor targeted bimodal liposomes for tumor magnetic resonance imaging. Bioconjug Chem. 2009; 20(4):648-55. [Also cited in ISR].

Kelkar SS, et al., Theranostics: Combining imaging and therapy. Bioconjug Chem 2011;22:1879-1903.

Kenny GD, et al., Novel multifunctional nanoparticle mediates siRNA tumour delivery, visualisation and therapeutic tumour reduction in vivo. J Control Release. 2011;149(2):111-6. Epub Oct. 5, 2010.

Khaibullina A, et al., Pulsed high-intensity focused ultrasound enhances uptake of radiolabeled monoclonal antibody to human epidermoid tumor in nude mice. J Nucl Med 2008;49:295-302.

Kiessling F, et al., Recent advances in molecular, multimodal and theranostic ultrasound imaging. Adv Drug Deliv Rev 2014;72:15-27.

Kneidl B, et al., Thermosensitive liposomal drug delivery systems: State of the art review. Int J Nanomedicine 2014;9:4387-4398.

Kong G et al. Efficacy of liposomes and hyperthermia in a human tumor xenograft model: importance of triggered drug release. Cancer Research., vol. 60, 2000, pp. 6950-6957.

Kong G, et al., Characterization of the effect of hyperthermia on nanoparticle extravasation from tumor vasculature. Cancer Res. 2001;61(7):3027-32. Epub Apr. 18, 2001.

Kong G, et al., Hyperthermia enables tumor-specific nanoparticle delivery: effect of particle size. Cancer Res. 2000;60(16):4440-5. Epub Sep. 2, 2000.

Landon CD, et al., Nanoscale Drug Delivery and Hyperthermia: The Materials Design and Preclinical and Clinical Testing of Low Temperature-Sensitive Liposomes Used in Combination with Mild Hyperthermia in the Treatment of Local Cancer. Open Nanomed J. 2011;3:38-64. Epub Jan. 1, 2011.

Lanza GM, et al., Assessing the barriers to image-guided drug delivery. Wiley Interdiscip Rev Nanomed Nanobiotechnol. 2014;6(1):1-14. Epub Dec. 18, 2013.

Leveque D, Gigou L, Bergerat JP. Clinical pharmacology of trastuzumab. Curr Clin Pharmacol 2008;3:51-55.

Li L, et al., A novel two-step mild hyperthermia for advanced liposomal chemotherapy. J Control Release 2014;174:202-208.

Li L, et al., Mild hyperthermia triggered doxorubicin release from optimized stealth thermosensitive liposomes improves intratumoral drug delivery and efficacy. J Control Release. 2013;168(2):142-50. Epub Mar. 26, 2013.

Lorenzato, Cyril; et al., MRI contrast variation of thermosensitive magnetoliposomes triggered by focused ultrasound: a tool for image-guided local drug delivery, Contrast Media & Molecular Imaging (2013), 8(2), 185-192.

Ma X, et al., Theranostic nanoparticles engineered for clinic and pharmaceutics. Acc Chem Res. 2011;44(10):1114-22. Epub Jul. 8, 2011.

Mahajan A, et al., Bench to bedside molecular functional imaging in translational cancer medicine: To image or to imagine? Clin Radiol 2015;70:1060-1082.

Mariska de Smet et al., Journal of Controlled Release 169 (2013); 82-90, SPECT/CT Imaging of TSLs for MR-image guided delivery with HIFU.

May JP, et al., Hyperthermia-induced drug targeting. Expert Opin Drug Deliv. 2013;10(4):511-27. Epub Jan. 8, 2013.

Melancon MP, et al., Near-infrared light modulated photothermal effect increases vascular perfusion and enhances polymeric drug delivery. J Control Release 2011;156(2):265-72. Epub Jul. 19, 2011.

(56) References Cited

OTHER PUBLICATIONS

Miller AD. Delivery of RNAi therapeutics: work in progress. Expert review of medical devices. 2013;10(6):781-811. Epub Nov. 8, 2013.
Miller AD. Lipid-based nanoparticles in cancer diagnosis and therapy. Journal of drug delivery. 2013;2013:165981. Epub Aug. 13, 2013.
Mitchell N et al., Incorporation of paramagnetic, fluorescent and PET/SPECT contrast agents into liposomes for multimodal imaging. Biomaterials, vol. 34, Issue 4, Jan. 2013, pp. 1179-1192.
Miyamoto R, et al., Cetuximab delivery and antitumor effects are enhanced by mild hyperthermia in a xenograft mouse model of pancreatic cancer. Cancer Sci 2016;107:514-520.
Needham D, et al., The development and testing of a new temperature-sensitive drug delivery system for the treatment of solid tumors. Adv Drug Deliv Rev. 2001;53(3):285-305. Epub Dec. 18, 2001.
Nitta H, et al., The assessment of her2 status in breast cancer: The past, the present, and the future. Pathol Int 2016.
O'Neill B., et al., J. Hyperthermia, Sep. 2008, 24(6):506-520 (Augmentation of targeted delivery with pulsed HIFU).
Oude Munnink TH, et al., Molecular imaging of breast cancer. Breast 2009;18 Suppl 3:S66-73.
Paoli EE, et al., An optical and microPET assessment of thermally-sensitive liposome biodistribution in the Met-1 tumor model: Importance of formulation. J Control Release. 2010;143(1):13-22. Epub Dec. 17, 2009.
Park et al, Novel temperature-triggered liposome with high stability: Formulation, in vitro evaluation, and in vivo study combined with high-intensity focused ultrasound (HIFU). J Control Release. 2013;170(3):373-9.
Patankar NA, et al., a liposomal nanoparticle formulation of topotecan for treatment of ovarian cancer. Invest New Drugs. 2013;31(1):46-58. Epub May 23, 2012.
Pinto AC, et al., Trastuzumab for patients with her2 positive breast cancer: Delivery, duration and combination therapies. Breast 2013;22 Suppl 2:S152-155.
Poon RT, et al., Lyso-thermosensitive liposomal doxorubicin: an adjuvant to increase the cure rate of radiofrequency ablation in liver cancer. Future Oncol. 2011;7(8):937-45. Epub Aug. 10, 2011.
Quinn SD, Gedroyc WM. Thermal ablative treatment of uterine fibroids. Int J Hyperthermia 2015;31:272-279.
Rosca, EV et al., Thermosensitive, Near-Infrared-Labeled Nanoparticles for Topotecan Delivery to Tumors. Mol. Pharmaceutics, 2015, 12 (5), pp. 1335-1346.
Song S, et al., Novel peptide ligand directs liposomes toward EGF-R high-expressing cancer cells in vitro and in vivo. Faseb J. 2009;23(5):1396-404.
Sonnenblick A, et al., Lapatinib-related rash and breast cancer outcome in the altto phase iii randomized trial. J Natl Cancer Inst 2016;108.
Stipsanelli E, et al., Monoclonal antibodies: Old and new trends in breast cancer imaging and therapeutic approach. Hell J Nucl Med 2005;8:103-108.
Suganami A, et al., Preparation and characterization of phospholipid-conjugated indocyanine green as a near-infrared probe. Bioorg Med Chem Lett. 2012;22(24):7481-5. Epub Nov. 6, 2012.
Tagami et al, Optimization of a novel and improved thermoosensitive liposome formulated with DPPC and a Brij surfactant using a robust in vitro system. J Control Release 2011;154(3):290-7 [Also cited in ISR].
Tardi P, et al., Liposomal encapsulation of topotecan enhances anticancer efficacy in murine and human xenograft models. Cancer Res. 2000;60(13):3389-93. Epub Jul. 26, 2000.
Thanou M, Gedroyc W. MRI-guided focused ultrasound as a new method of drug delivery. J Drug Deliv 2013; 2013:616197. [Also cited in ISR].
Thanou, M., et al., Nanoparticles for image guided focused ultrasound drug delivery, [abstract]. In: Proceedings of the 105th Annual Meeting of the American Association for Cancer Research; Apr. 5-9, 2014; San Diego, CA. Philadelphia (PA): AACR; Cancer Res 2014;74(19 Suppl):Abstract nr 5398. doi:10.1158/1538-7445.AM2014-5398.
Thanou, M., et al., Poster, Nanoparticles for image guided focused ultrasound drug delivery. [abstract]. In: Proceedings of the 105th Annual Meeting of the American Association for Cancer Research; Apr. 5-9, 2014; San Diego, CA. Philadelphia (PA): AACR; Cancer Res 2014;74(19 Suppl):Abstract nr 5398. doi:10.1158/1538-7445. AM2014-5398.
Tu J, et al., Controllable in vivo hyperthermia effect induced by pulsed high intensity focused ultrasound with low duty cycles. Appl Phys Lett. 2012;101(12):124102. Epub Nov. 1, 2012.
Wang S, et al., Pulsed high intensity focused ultrasound increases penetration and therapeutic efficacy of monoclonal antibodies in murine xenograft tumors. J Control Release 2012;162:218-224.
Wang S, Frenkel V, Zderic V. Optimization of pulsed focused ultrasound exposures for hyperthermia applications. J Acoust Soc Am 2011;130:599-609.
Weber WA, et al., Technology insight: Novel imaging of molecular targets is an emerging area crucial to the development of targeted drugs. Nat Clin Pract Oncol 2008;5:44-54.
Wu F. Extracorporeal high intensity focused ultrasound in the treatment of patients with solid malignancy. Minim Invasive Ther Allied Technol 2006;15:26-35.
Yarden Y, Sliwkowski MX. Untangling the erbb signalling network. Nat Rev Mol Cell Biol 2001;2:127-137.
Zelmer A, Ward TH. Noninvasive fluorescence imaging of small animals. J Microsc 2013;252:8-15.
Zhu W, et al., Pamam dendrimer-based contrast agents for mr imaging of her-2/neu receptors by a three-step pretargeting approach. Magn Reson Med 2008;59:679-685.
Jeon et al., Iron Oxide Nanoparticles as T1 Contrast Agents for Magnetic Resonance Imaging: Fundamentals, Challenges, Applications, and Prospectives, Adv. Mater. 2020:1906539 (2020).
Han et al., Research into europium complexes as magnetic resonance imaging contrast agents (Review), Exp. Ther. Med. 9:1561-66 (2015).
Ren et al., MRI-visible liposome nanovehicles for potential tumor-targeted delivery of multimodal therapies, Nanoscale 7:12843-50 (2015).
Vazquez et al., Plasma protein denaturation with graded heat exposure, Perfusion 28:557-59 (2013).
Hijnen et al., Thermal combination therapies for local drug delivery by magnetic resonance-guided high-intensity focused ultrasound, Proc. Natl. Acad Sci. USA 114:E4802-11 (2017).
Leone et al., Optimizing the Relaxivity of MRI Probes at High Magnetic Field Strengths With Binuclear Gd111 Complexes, Front. Chem. 6:158 (2018).

* cited by examiner

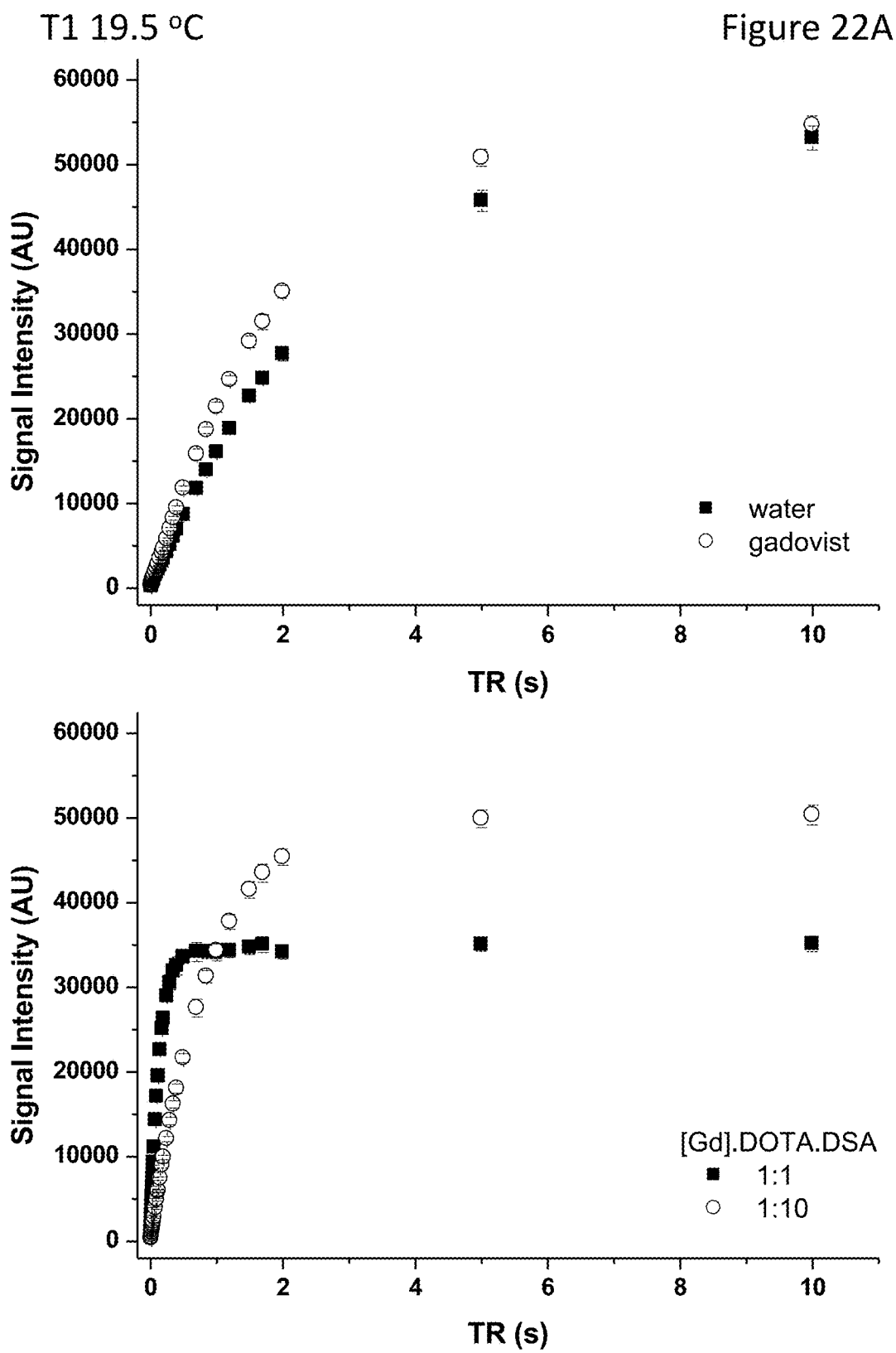

T2 19.5 °C

NANOPARTICLES

CROSS-REFERENCE TO RELATED APPLICATIONS

This application claims the benefit of priority to International Patent Application No.: PCT/GB2016/051693, filed Jun. 8, 2016, which claims priority to Great Britain Patent Application No.: 1509934.4, filed on Jun. 8, 2015, the entire content of these applications is incorporated by reference herein in its entirety.

FIELD OF THE INVENTION

The present invention relates to a new lipid nanoparticle (LNP) and its use in therapy. In one embodiment, the invention relates to lipid nanoparticles comprising a magnetic resonance imaging and/or a Near IR fluorescence label, and use of such lipid nanoparticles in a method of image-guided focused hyperthermia, e.g. for drug delivery. In one embodiment, the lipid nanoparticles are thermosensitive.

BACKGROUND TO THE INVENTION

Nanoparticle drug delivery systems for cancer have not shown the expected therapeutic results. For example, in the case of Doxil®, the nanoparticle mediated increases in drug (doxorubicin) concentration in tumours has been poor (approx. 3% of overall dose) and release of drug from encapsulation is slow, not reaching therapeutic levels of drug in the tumour. In addition, biological factors such as tumour vascularisation and perfusion can influence cancer cell uptake of nanoparticles (1).

Mild hyperthermia can enhance local blood flow which will diminish tumour interstitial pressure thereby promoting the tumour uptake of therapeutic nanoparticles, macromolecules and drug delivery systems (of up to 400 nm) (2, 3). Various methods have been introduced to generate hyperthermia such as lasers, hot water baths, plus microwave and radiofrequency applicators with different heat transfer rates.

Thermosensitive drug carriers, such as thermosensitive liposomes (TSLs), can be used in conjunction with hyperthermia in order to enhance cancer treatment. For example doxorubicin-enclosing TSLs (thermosensitive liposomal doxorubicin known as Thermodox®) were used in combination with mild hyperthermia and found to be significantly more effective than free drug or Doxil® formulations at reducing tumour growth in mice xenografts as well as in canine tumours (4, 5, 35). Thermodox® has been used with radiofrequency (RF) ablation (6).

However, Thermodox® has problems with instability in vivo and drug leakage. Thus improved nanoparticle drug delivery systems, in particular improved TSLs, are sought. Improved methods of generating hyperthermia are also desired to improve uptake of drugs from nanoparticle drug delivery systems/TSLs upon image guidance.

WO 2009/05944 describes thermosensitive liposomes containing therapeutic agents. WO 2013/123407 describes thermosensitive nanoparticle formulations.

SUMMARY OF THE INVENTION

The present invention can solve, or at least alleviate, (some of) the problems of the prior art.

In one aspect, the present invention provides a lipid nanoparticle comprising:
(i) at least one phospholipid;
(ii) at least one lysolipid;
(iii) at least one phospholipid comprising a hydrophilic polymer; and
(iv) at least one structural lipid of formula (I):

wherein R and R' are long hydrocarbyl hydrophobic chains, Y is a linker element, and PHG is a polar head group described as large according to its van der Waals radius, and which is different from the phospholipid (i).

In one embodiment, the lipid nanoparticle is thermosensitive.

The structural lipid (iv) of formula (I) may comprise a magnetic resonance imaging (MRI) label comprising a paramagnetic metal lipid.

The lipid nanoparticle may further comprise a near infrared fluorescence (NIRF) imaging label.

In one embodiment, the lipid nanoparticle may further comprise an active pharmaceutical ingredient (API). Such LNPs may also be referred to as theranostic nanoparticles (TNPs) (i.e. capable of therapy and diagnostic imaging applications).

In another aspect, the present invention provides a pharmaceutical composition incorporating the lipid nanoparticle and a pharmaceutically acceptable carrier.

The invention further provides a lipid nanoparticle or pharmaceutical composition for use in the treatment of cancer.

The invention also relates to a method of treatment comprising:
administering to a subject in need thereof a therapeutically effective amount of a lipid nanoparticle or pharmaceutical composition of the invention;
monitoring the progress of the lipid nanoparticle or pharmaceutical composition to an area of interest using MRI and/or optical imaging methods; and
heating the area of interest, preferably by applying continuous and/or high frequency ultrasound, particularly high intensity focused ultrasound (HIFU).

In another aspect, the present invention provides a lipid of formula (II)

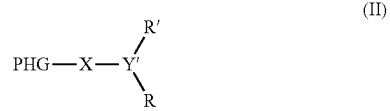

wherein R and R' are long hydrocarbyl hydrophobic chains, X and Y' are linker elements and PHG is a polar head group described as large according to its van der Waals radius, as discussed further below.

The present invention further provides a lipid nanoparticle comprising a lipid of formula (II), a pharmaceutical composition comprising a lipid of formula (II) (e.g. as a lipid nanoparticle comprising a lipid of formula (II)) and a pharmaceutically acceptable carrier, and a lipid of formula (II) (or said lipid nanoparticle and/or pharmaceutical composition comprising a lipid of formula (II)) for use in a method of therapy or diagnosis of the human or animal body, such as in the treatment of cancer.

BRIEF DESCRIPTION OF THE DRAWINGS

FIGS. 22A, 22B, 23A, and 23B—Example T1 and T2 brightness traces for controls and liposome samples. Curve fitting from this data to gives the T1 or T2 values for these samples

DETAILED DESCRIPTION OF THE INVENTION

Lipid Nanoparticles

Figure 1:
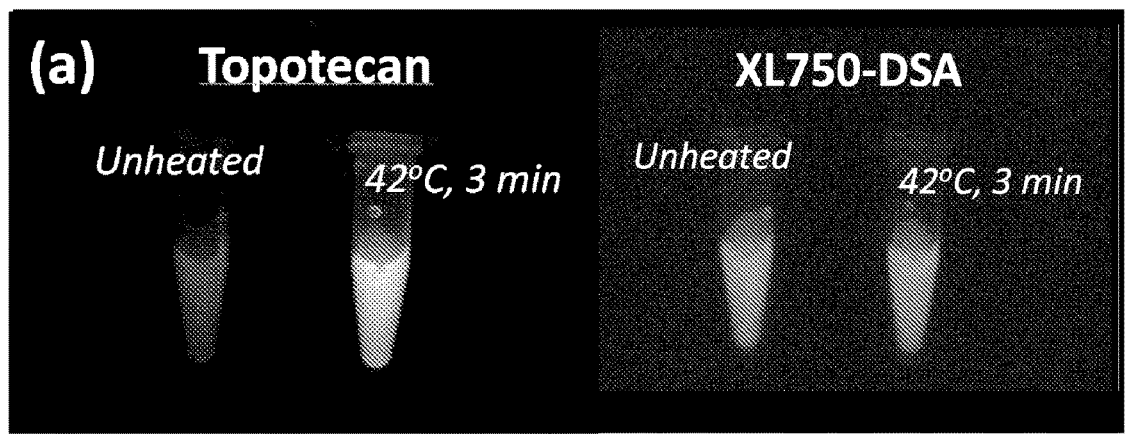
FIG. 1: Topotecan released from thermosensitive liposomes (TNPs) monitored by changes in the intrinsic fluorescence of the drug (Ex 410 nm, Em 540 nm); (a) Spectrally deconvulated ('unmixed') images of collected data from a Maestro EX in vivo multispectral analyser of unheated (left) and heated (right) samples, showing topotecan fluorescence emission at the top, and at the bottom no change in NIRF signal from the XL750-DSA labelled lipids. (b) Topotecan release profiles after incubation at different temperatures (critical $T_m$ 40° C.), error bars show ±3×S.D.
Figure 1:
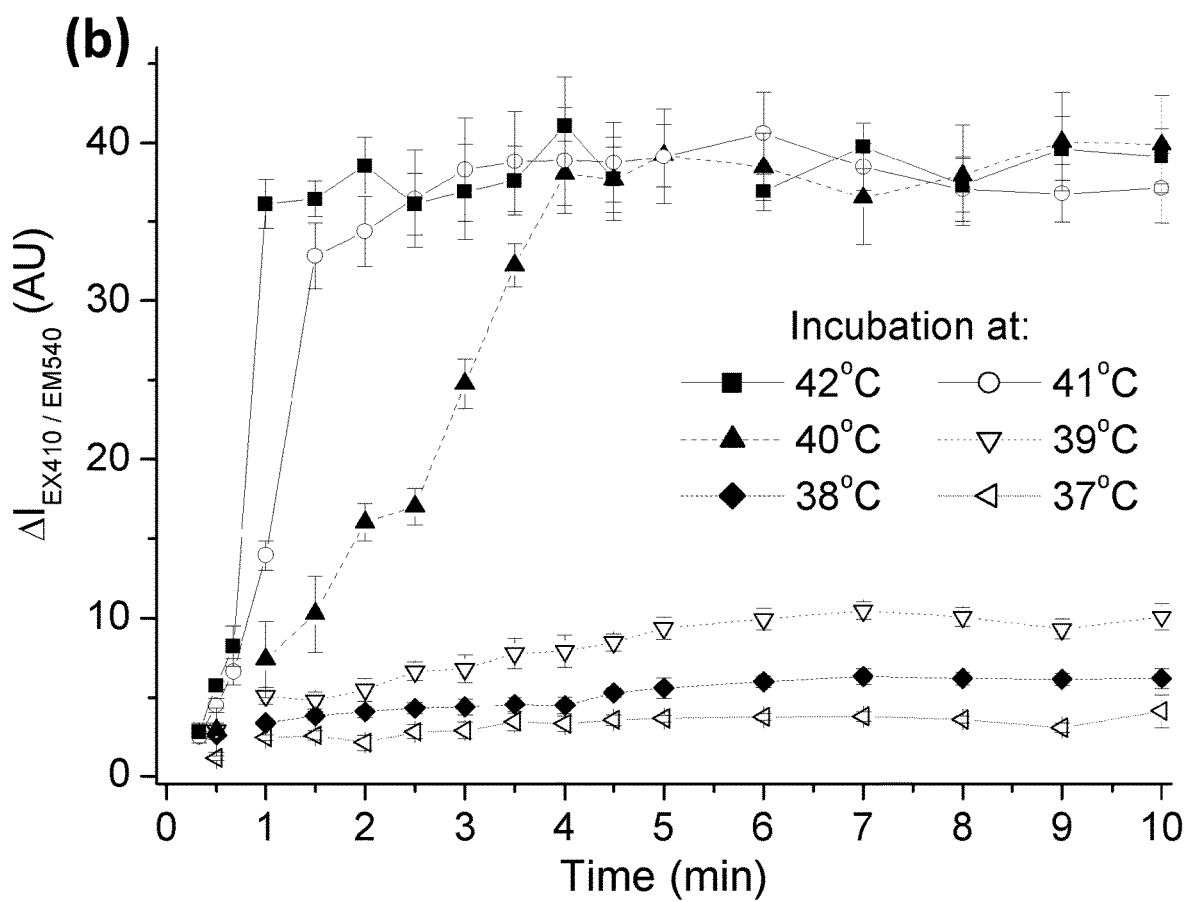

The present invention relates to a lipid nanoparticle comprising:
(i) at least one phospholipid;
(ii) at least one lysolipid;
(iii) at least one phospholipid comprising a hydrophilic polymer;
(iv) at least one structural lipid of formula (I):

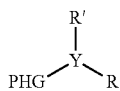

wherein R and R' are long hydrocarbyl hydrophobic chains, Y is a linker element, and PHG is a polar head group described as large according to its van der Waals radius, and which is different from the phospholipid (i).

In one embodiment, the lipid nanoparticle is thermosensitive.

The lipid nanoparticles, or LNPs, of the present invention are typically lipid-based vesicles that may be classed generically as liposomes. Thus where used herein, the term "lipid nanoparticle" refers in a preferred embodiment to a liposome (i.e. liposome is a subset of lipid nanoparticle). Liposomes are typically spherical or particulate structures comprising one or more lipid bilayer membranes. They may contain an encapsulated aqueous volume. Liposomes may contain many concentric lipid bilayer(s), e.g. separated by an aqueous phase (multilamellar vesicles), or alternatively, they may comprise a single membrane bilayer (unilamellar vesicles). In the membrane bilayer, the hydrophobic (non-polar) "tails" of the lipid monolayers normally orient toward the centre of the bilayer; whereas the hydrophilic (polar) "heads" orient toward the aqueous phases. The lipid nanoparticles of the present invention are typically nanoparticles.

In one embodiment, the lipid nanoparticle of the present invention comprises:
(i) at least one phospholipid;
(ii) at least one lysolipid;
(iii) at least one phospholipid comprising a hydrophilic polymer; and
(iv) at least one structural lipid of formula (I) as described above, which comprises a magnetic resonance imaging (MRI) label comprising a paramagnetic metal lipid.

In one embodiment, the above-described lipid nanoparticle is thermosensitive.

In another embodiment, the lipid nanoparticle of the present invention comprises:
(i) at least one phospholipid;
(ii) at least one lysolipid;
(iii) at least one phospholipid comprising a hydrophilic polymer;
(iv) at least one structural lipid of formula (I) as described above; and
(v) a near infrared fluorescence (NIRF) imaging label.

In one embodiment, the above-described lipid nanoparticle is thermosensitive.

In one embodiment, the lipid nanoparticle of the present invention comprises:
(i) at least one phospholipid;
(ii) at least one lysolipid;
(iii) at least one phospholipid comprising a hydrophilic polymer;
(iv) at least one structural lipid of formula (I) as described above, which comprises a magnetic resonance imaging (MRI) label comprising a paramagnetic metal lipid; and
(v) a near infrared fluorescence (NIRF) imaging label.

In one embodiment, the above-described lipid nanoparticle is thermosensitive.

Since the lipid nanoparticle of the present invention can comprise imaging label(s) (e.g. MRI and/or NIRF), it is possible to monitor the lipid nanoparticles in vivo. The lipid nanoparticles can thus be theranostic, i.e. they are capable of simultaneous therapeutic and diagnostic applications.

The components (i) to (iv) of the lipid nanoparticle of the present invention, in particular the thermosensitive lipid nanoparticle of the present invention, can be classed into three lipid groups which may work in synergy (it should be noted that these groups are not mutually exclusive and each component may have a number of functions within the lipid nanoparticle):
1. Structural lipids: the "pure structural" phospholipid (ii) and the structural lipid (iv) of formula (I);
2. Stealth/biocompatibility lipids: the phospholipid comprising a hydrophilic polymer (iii); and
3. Thermosensitising lipids: lysolipid (ii).

Components (i) to (v) of the lipid nanoparticle of the present invention are described in more detail below.

Phospholipid

The lipid nanoparticle of the present invention can comprise a phospholipid, which forms the "base" lipid and may provide structural stability to the lipid nanoparticle. The phospholipid may be a single phospholipid or a mixture of one or more different phospholipids.

The phospholipid may be selected from, for example, phosphatidylcholines, phosphatidylethanolamines, phosphatidylglycerols, phosphatidylserines, phosphatidic acids, phosphatidylinositols and/or sphingolipids. Preferably, the phospholipid is selected from phosphatidylcholines and phosphatidylethanolamines. In one embodiment, the phospholipid is not a phosphatidylglycerol (for example the phospholipid is not 1,2-dipalmitoyl-sn-glycero-3-phospho-(1'-rac-glycerol)).

In one embodiment, the phospholipid has the following general structure:

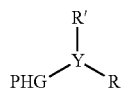

wherein R and R' are long hydrocarbyl hydrophobic chains, Y is a linker element, typically glycerol, and PHG is a polar head group. The PHG may for example have a diameter of preferably greater than about 5 Å, more preferably from about 5 to about 15 Å. Alternatively, the PHG may have a diameter of from about 3 to about 5 Å. (In this context, the "diameter" may correspond, for example, to the longest atom-to-atom distance measured from a suitable van der Waals space fill model, such as Chem3D).

Thus, for example, the phospholipid may be selected from one or more phosphatidylcholines and phosphatidylethanolamines, such as 1,2-di($C_{12}$-$C_{20}$ lipid)-sn-glycero-3-phosphocholines and/or 1,2-di($C_{12}$-$C_{20}$ lipid)-sn-glycero-3-phosphoethanolamines, wherein the lipid groups can be the same or different from each other. Preferably the phospholipid may be selected from one or more 1,2-di($C_{12}$-$C_{20}$ saturated lipid)-sn-glycero-3-phosphocholines and/or 1,2-di($C_{12}$-$C_{20}$ saturated lipid)-sn-glycero-3-phosphoethanolamines, wherein the saturated lipid groups can be the same or different from each other. Suitable examples of the 1,2-di($C_{12}$-$C_{20}$ saturated lipid)-sn-glycero-3-phosphocholine are 1,2-dipalmitoyl-sn-glycero-3-phosphocholine (DPPC) and 1,2-distearoyl-sn-glycero-3-phosphocholine (DSPC). A suitable example of the 1,2-di($C_{12}$-$C_{20}$ saturated lipid)-sn-glycero-3-phosphoethanolamine is 1,2-dioctadecanoyl-sn-glycero-3-phosphoethanolamine (DSPE).

Suitably the phospholipid comprises at least one phosphatidylcholine. Preferably, the phosphatidylcholine comprises a 1,2-di($C_{12}$-$C_{20}$ saturated lipid)-sn-glycero-3-phosphocholine, wherein the saturated lipid groups can be the same or different from each other. For example, the phosphatidylcholine may comprise DPPC and/or DSPC.

In one embodiment, the phospholipid may comprise two or more, preferably two, different phosphatidylcholines, preferably two or more different 1,2-di($C_{12}$-$C_{20}$ saturated lipid)-sn-glycero-3-phosphocholines, preferably two different 1,2-di($C_{12}$-$C_{20}$ saturated lipid)-sn-glycero-3-phosphocholines. For example, in one preferred embodiment, the phosphatidylcholine comprises DPPC and DSPC.

The phospholipid is preferably contained in the lipid nanoparticle in an amount of from about 30 to about 90 mol %, preferably from about 40 to about 75 mol %. When the phospholipid comprises a mixture of phospholipids, preferably a first phospholipid (such as a phosphatidylcholine or phosphatidylethanolamine) is contained in an amount of from about 40 to about 70 mol %, preferably about 45 to about 55 mol %, and a second phospholipid (such as a phosphatidylcholine or phosphatidylethanolamine) is contained in an amount of from about 0.1 to about 10 mol %, preferably from about 2 to about 8 mol %. For example, in one embodiment a first phosphatidylcholine is contained in an amount of from about 40 to about 70 mol %, preferably about 45 to about 55 mol %, and a second phosphatidylcholine is contained in an amount of from about 0.1 to about 10 mol %, preferably from about 2 to about 8 mol %.

If the phospholipid comprises two different 1,2-di($C_{12}$-$C_{20}$ saturated lipid)-sn-glycero-3-phosphocholines, preferably the phosphatidylcholine having shorter $C_{12}$-$C_{20}$ saturated lipid chains is the "first phosphatidylcholine" as described above, and is thus present in a greater amount than the phosphatidylcholine having longer $C_{12}$-$C_{20}$ saturated lipid chains, which is the "second phosphatidylcholine" as described above. Thus, for example, when the "first phosphatidylcholine" is DPPC and the "second phosphatidylcholine" is DSPC, the amount of DPPC is greater than the amount of DSPC. Preferably, the lipid nanoparticle comprises DPPC in an amount of from about 40 to about 70 mol %, preferably about 45 to about 55 mol %, and DSPC in an amount of from about 0.1 to about 10 mol %, preferably from about 2 to about 8 mol %.

Including two (or more) different phosphatidylcholines can be advantageous in allowing the stability and release properties of the lipid nanoparticle to be tailored, for example to improve colloidal stability. For thermosensitive lipid nanoparticles the inclusion of two (or more) different phosphatidylcholines can adjust the temperature at which the lipid nanoparticles are thermosensitive. For example, when the major component of the phospholipid is DPPC, including a small amount of DSPC can improve colloidal stability and increase the thermosensitive temperature.

The phospholipid should be selected such that the lipid bilayer membranes of the lipid nanoparticle (i.e. the liposome) are not too stable, e.g. such that they are insensitive to drug loading protocols and/or not thermosensitive (e.g. are insensitive to ultrasound induced hyperthermia). In one embodiment, the phospholipid does not comprise a mixture in which the proportion of DSPC is greater than 80% and the proportion of DPPC is less than 20%, such as HydroSoy PC.

Lysolipid

The lipid nanoparticle of the present invention may also comprise a lysolipid. In the case of thermosensitive lipid nanoparticles, the lysolipid can contribute to the thermosensitive properties of the lipid nanoparticle. The lysolipid may in particular be an ultrasound induced hyperthermia sensitive lipid.

In one embodiment, the lysolipid has the following general structure:

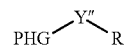

wherein R is a long hydrocarbyl hydrophobic chain, Y" is a linker element, typically glycerol, and PHG is a polar head group.

The PHG may be for example have a diameter (as described above for the phospholipid) of greater than about 3 Å, preferably greater than about 5 Å, more preferably from about 5 to about 15 Å. Alternatively, the PHG may have a diameter of from about 3 to about 5 Å.

The lysolipid may be a lysophospholipid selected from, for example, monoacylphosphatidylcholines, monoacylphosphatidylglycerols, monoacylphosphatidylinositols, and monoacylphosphatidyl-ethanolamines. The lysolipid may have molecular weight of from about 100 to about 1500 Da.

Suitably the lysolipid comprises a monoacylphosphatidylcholine. Preferably, the lysolipid comprises a 1-($C_{12}$-$C_{20}$ saturated lipid)-sn-glycero-3-phosphocholine. For example, the lysolipid may comprise monopalmitoylphosphatidylcholine (MPPC), monolaurylphosphatidylcholine (MLPC), monomyristoylphosphatidylcholine (MMPC) and/or monostearoylphosphatidylcholine (MSPC). Preferably, the lysolipid comprises MPPC and/or MSPC. In one preferred embodiment, the lysolipid comprises monostearoylphosphatidylcholine (MSPC):

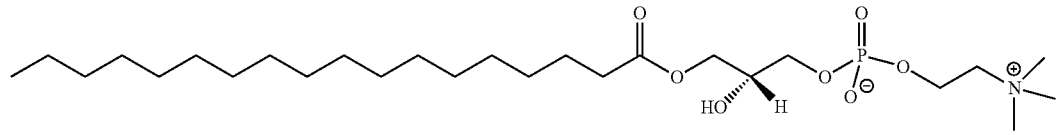 [SMILES: CCCCCCCCCCCCCCCCCC(=O)OC[C@@H](O)COP(=O)([O-])OCC[N+](C)(C)C]

1-stearoyl-2-hydroxy-sn-glycero-3-phosphocholine (MSPC; 18:0 lyso PC)

In an alternative embodiment, the lysolipid may be substituted by a «lysolipid mimic», i.e. another component that provides thermosensitivity. An Example is the surfactant Brij78 (BrijS20): $C_{18}H_{37}(OCH_2CH_2)_{20}OH$:

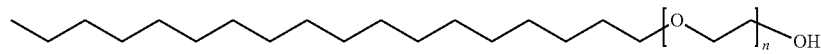

Brij-78 (Stearyl alcohol EO; n~20)

The use of this component is described in Tagami et al, J Control Release. 2011; 154(3):290-7. 2011. Optimization of a novel and improved thermosensitive liposome formulated with DPPC and a Brij surfactant using a robust in vitro system.

Another example is SA-EL$_3$-NH$_2$ (8):

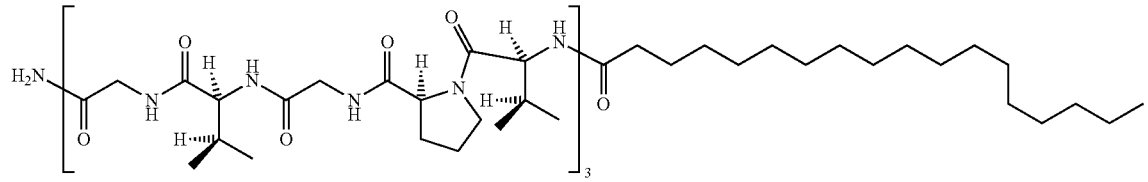

Novel temperature-triggered liposome with high stability: formulation, in vitro evaluation, and in vivo study combined with high-intensity focused ultrasound (HIFU).

The lysolipid is preferably contained in the lipid nanoparticle in an amount of from about 2 to about 15 mol %, preferably from about 3 to about 10 mol %. When the lysolipid is MSPC, it may preferably be present in an amount of about 5 mol %, more preferably wherein the lipid nanoparticle also comprises the phospholipid DSPC in an amount of about 5 mol %.

As noted above, the lysolipid can contribute to the thermosensitive properties of the lipid nanoparticle, for example assisting the rapidity of lipid nanoparticle content release on reaching the critical temperature. Without wishing to be bound by theory, this may be due to the formation of "pore" or crystal flaws on the lipid film due to the presence of the lysolipid (in particular where the lysolipid is colloidally unstable, as in the case of MSPC).

Phospholipid Comprising a Hydrophilic Polymer

The lipid nanoparticle of the present invention may also comprise a phospholipid comprising (e.g. derivatized with) a hydrophilic polymer. This component can provide (colloidal) stability to the lipid nanoparticle and/or assist with stealth/biocompatibility. In the case of thermosensitive lipid nanoparticles, it may also influence the thermosensitive properties of the lipid nanoparticle.

In one embodiment, the phospholipid comprising a hydrophilic polymer has the following general structure:

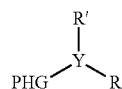

wherein R and R' are long hydrocarbyl hydrophobic chains, typically independently selected from $C_{12}$-$C_{20}$ (preferably saturated) alkyl groups, more preferably $C_{14}$-$C_{20}$ (preferably saturated) alkyl groups, Y is a linker element, typically glycerol, and PHG is a polar head group comprising the hydrophilic polymer. In this case the PHG may have a diameter (as described above for the phospholipid) of from about 20 to 25 Å.

The "hydrophilic polymer" part of the phospholipid comprising a hydrophilic polymer (e.g. PHG in the above structure) may be selected from, for example, polyethylene glycol, polyvinylpyrolidine, polylactic acid, polyglycolic acid, copolymers of polylactic acid and polyglycolic acid, polyvinyl alcohols, polyvinylpyrrolidone, dextrans and/or oligosaccharides. The phospholipid comprising a hydrophilic polymer is preferably a polyethylene glycol derivatized (PEGylated) lipid. The PEG polymer typically varies from short (350 MWt up to 10000 MWt). PEG mixtures could be used as well. In addition PEG lipids could be conjugated with receptor-specific targeting ligands such as folate, as described below.

Suitably the "phospholipid" part of the phospholipid comprising a hydrophilic polymer comprises a phospholipid selected from phosphatidylcholines, phosphatidylethanolamines, phosphatidylglycerols, phosphatidylserines, phosphatidic acids, phosphatidylinositols and/or sphingolipids. Preferably, the phospholipid in the phospholipid comprising a hydrophilic polymer comprises a phosphatidylethanolamine, for example a 1-($C_{12}$-$C_{20}$ saturated lipid)-sn-glycero-3-phosphoethanolamine.

The phospholipid comprising a hydrophilic polymer is preferably a PEGylated phosphatidylethanolamine, in particular a PEGylated 1-($C_{12}$-$C_{20}$ saturated lipid)-sn-glycero-3-phosphoethanolamine.

The phospholipid comprising a hydrophilic polymer preferably comprises (ω-methoxy-polyethylene glycol 2000)-N-carboxy-1,2-distearoyl-sn-glycero-3-phosphoethanolamine ($PEG^{2000}$-DSPE) and/or (ω-methoxy-polyethylene glycol 2000)-N-carboxy-1,2-palmitoyl-sn-glycero-3-phosphoethanolamine ($PEG^{2000}$-DPPE), preferably $PEG^{2000}$-DSPE.

The phospholipid comprising a hydrophilic polymer is preferably contained in the lipid nanoparticle in an amount of from about 3 or 4 to about 10 mol %, e.g. from about 5 to about 10 mol %, preferably from about 3 to about 8 mol %, e.g. from about 5 or 6 to about 8 mol %, more preferably from about 4 to about 7 mol %, e.g. from about 6 to about 6.5 mol %. In particular, when the phospholipid comprising a hydrophilic polymer is $PEG^{2000}$-DSPE, this is preferably contained in the lipid nanoparticle in an amount of from about 3 or 4 to about 8 mol %, e.g. from about 5 or 6 to about 8 mol %, more preferably from about 4 to about 7 mol %, e.g. from about 6 to about 6.5 mol %.

By using the phospholipid comprising a hydrophilic polymer in such amount, it may be possible to tailor the desired stability-temperature release profile, i.e. to improve thermal stability and/or adjust the temperature at which the lipid nanoparticles are thermosensitive. For example in the case of thermosensitive lipid nanoparticles, using the phospholipid comprising a hydrophilic polymer in a preferred amount can contribute to improved thermal stability below a critical temperature (i.e. the temperature at which the lipid nanoparticles become thermosensitive) and to a rapid release of lipid nanoparticle content on reaching the critical temperature. Thus a "sharp" temperature release profile can be achieved.

Structural Lipid of Formula (I)

The lipid nanoparticle of the present invention may also comprise at least one structural lipid of formula (I), which, with the phospholipid, forms the "base" lipid and may provide structural stability to the lipid nanoparticle.

The structural lipid is of formula (I):

(I)

wherein R and R' are long hydrocarbyl hydrophobic chains, Y is a linker element, and PHG is a polar head group described as large according to its van der Waals radius with the proviso that it is different from the phospholipid (i). Preferably, the structural lipid of formula (I) is not a phospholipid.

The polar head group described as large according to its van der Waals radius may for example have a diameter (as described above for the phospholipid) of greater than about 3 Å, preferably greater than about 5 Å, more preferably from about 5 to about 15 Å. Alternatively, the PHG may have a diameter of from about 3 to about 5 Å. The polar head group described as large according to its van der Waals radius may also (or alternatively) be defined in terms of its molecular weight, which is typically greater than 200, preferably greater than 300, more preferably from 400 to 3000.

Examples of suitable polar head groups PHG include protecting groups, such as tert-butoxycarbonyl (Boc); amino acids, such as lysine; oligomers, e.g. of amino acids, for example di-, tri- or tetra-peptides, which may be formed from the same or different amino acids, such as $Gly_2Lys$ or $Glu_2Lys$; and optionally substituted poly(aminocarboxylate) groups. Suitably, PHG may have a terminal carboxylic acid/carboxylate group in the free form, so that it can form e.g. an amide link with YRR'.

PHG is preferably an optionally substituted poly(aminocarboxylate) group, preferably an unsubstituted poly(aminocarboxylate) group, such as diethylene triamine pentaacetic acid (DTPA) or 1,4,7,10-tetraazacyclododecane-1,4,7,10-tetraacetic acid (DOTA), which may or may not contain a chelated metal cation.

The hydrophobic hydrocarbon chains R and R' may independently be, for example, an alkyl group, preferably independently selected from $C_{12}$-$C_{20}$ (preferably saturated) alkyl groups, more preferably $C_{14}$-$C_{20}$ (preferably saturated) alkyl groups. R and R' may be the same or different. In one embodiment, R and R' are the same. Thus in one embodiment, R and R' are the same and are each a $C_{14}$-$C_{20}$ saturated alkyl group, preferably $C_{18}$ saturated alkyl group.

In one embodiment, the linker Y preferably comprises an amide functional group, such as an amidomethylamine group (wherein the terminal amine forms an amide link with a terminal carboxylic acid group of PHG). The group represented by YRR' may thus correspond to a lipid moiety which may comprise, for example, one or more alkyl groups, preferably $C_{12}$-$C_{20}$ (preferably saturated) alkyl groups, more preferably $C_{14}$-$C_{20}$ (preferably saturated) alkyl groups as described above. A suitable lipid moiety comprising alkyl groups may comprise a N,N-di($C_{12}$-$C_{20}$ saturated lipid) methylamine or a N,N-di($C_{12}$-$C_{20}$ saturated lipid) amidomethylamine, such as N,N-distearylamidomethylamine (DSA, also known as 2-amino-N,N-dioctadecylacetamide).

Examples of the structural lipid of formula (I) include 6,9-bis(carboxylatomethyl)-11-oxo-3-(2-oxo-2-(tetradecylamino)ethyl)-3,6,9,12-tetraazahexacosanoatic acid (DTPA-bis(myrisitylamide); DTPA.BMA); 2-{4,7-bis-carboxymethyl-10-[(N,N-distearylamidomethyl-N'-amido-methyl]-1,4,7,10-tetra-azacyclododec-1-yl}-acetic acid (DOTA.DSA; also known as 2,2',2"-(10-(2-((2-(dioctadecylamino)-2-oxoethyl)amino)-2-oxoethyl)-1,4,7,10-tetraazacyclododecane-1,4,7-triyl)triacetic acid); 2-(1-[(N,N-distearyl-amidomethyl]-N'-amidomethyl]-4,7,7-tris-carboxymethyl-1,4,7-triaza-sept-1-yl) acetic acid (DTPA.DSA; also known as 3,6,9-tris(carboxylatomethyl)-15-octadecyl-11,14-dioxo-3,6,9,12,15-pentaazatritriacontanoatic acid), or one of the structures shown below:

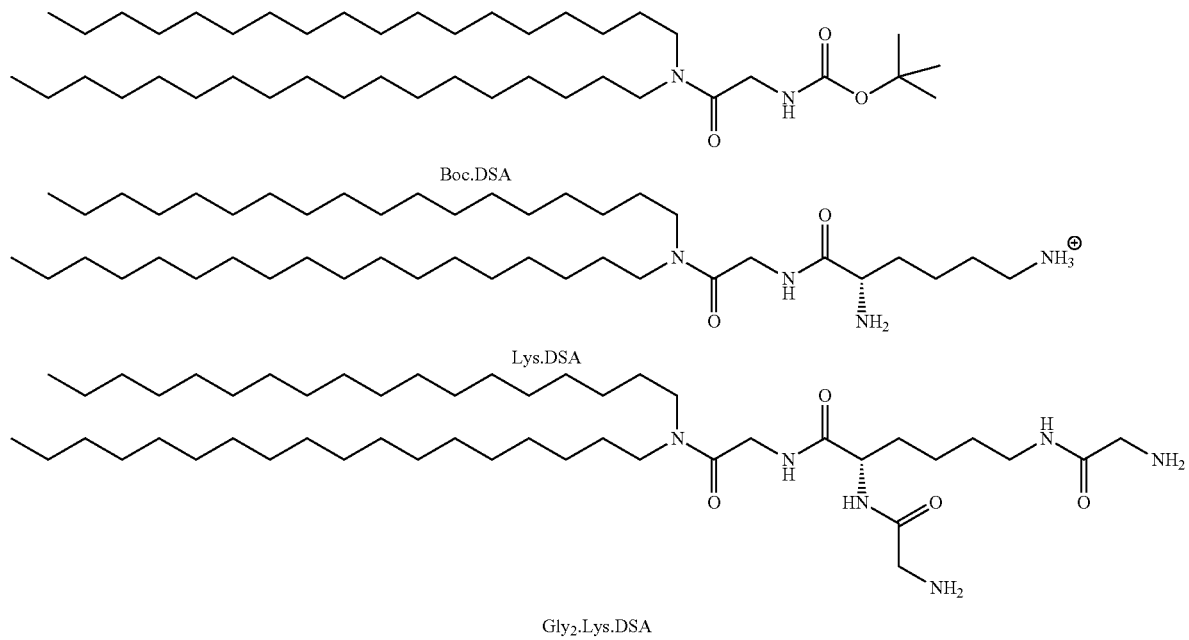

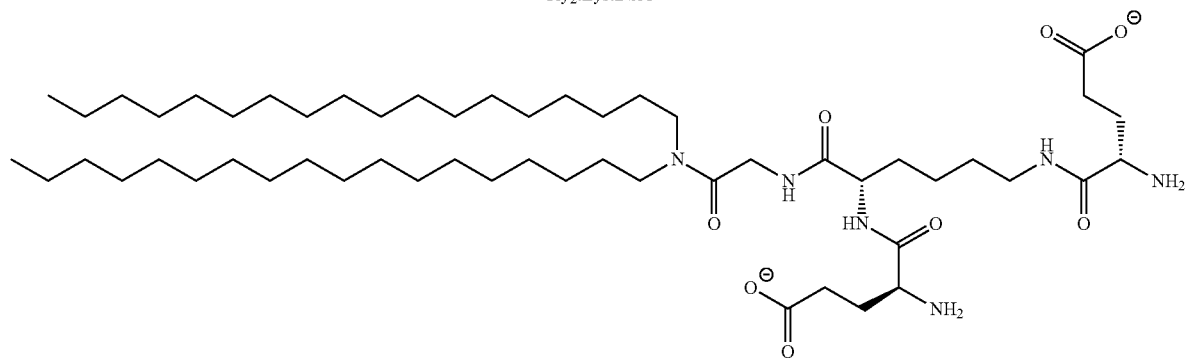

In one preferred embodiment, the structural lipid of formula (I) comprises DSA as the group YRR'. Thus in one preferred embodiment, the structural lipid of formula (I) comprises DOTA.DSA and/or DTPA.DSA as shown below (where R represents DOTA or DTPA), preferably DOTA.DSA.

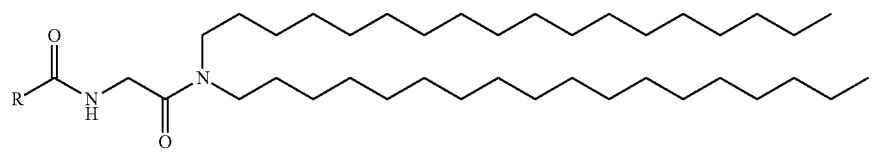

In another embodiment, the linker Y preferably comprises a group X-Y', for example such that the structural lipid of formula (I) is a lipid of formula (II):

$$PHG-X-Y'\begin{matrix}R'\\R\end{matrix} \quad (II)$$

wherein PHG, R and R' are as described above for formula (I), Y' is a linker element and X is a further linker which extends the distance between PHG and the hydrocarbyl chains R and R'.

The linker Y' preferably comprises a terminal functional group which may react with a terminal functional group of the linker X. For example, the linker Y' may comprise a terminal carboxylic acid group which reacts with a terminal amine group of X to form an amide link, or alternatively the linker Y' may comprise a terminal amine group which reacts with a terminal carboxylic acid group of X to form an amide link. In one preferred embodiment, Y' comprises an amide functional group, such as an amidomethylamine group (wherein the terminal amine forms an amide link with a terminal carboxylic acid group of X). The group represented by Y'RR' may thus correspond to a lipid moiety which may comprise, for example, one or more alkyl groups, preferably $C_{12}$-$C_{20}$ (preferably saturated) alkyl groups, more preferably $C_{14}$-$C_{20}$ (preferably saturated) alkyl groups as described above. A suitable lipid moiety comprising alkyl groups may comprise a N,N-di($C_{12}$-$C_{20}$ saturated lipid) amidomethylamine, such as N,N-distearylamidomethylamine (DSA).

The further linker X is preferably an organic linker group having a linear chain length of from 3 to 40 atoms (for example including, but not limited to, carbon, oxygen and/or nitrogen atoms). For example, the further linker X may comprise a hydrocarbyl chain, or may comprise carbon atoms and further functional groups such as ether, carboxyl, amine, amide or hydroxyl groups. Preferably X comprises a hydrocarbyl chain of from 3 to 12 carbon atoms, preferably from 3 to 10 carbon atoms, preferably a $C_3$-$C_{12}$ alkyl group (such as a $C_3$-$C_{12}$ saturated alkyl group), more preferably a $C_3$-$C_{10}$ alkyl group (such as a $C_3$-$C_{10}$ saturated alkyl group); a polyethylene glycol (PEG) group, in particular a PEG oligomer having for example from 2 to 10 ethylene oxide repeat units; one or more (e.g. one or two) aminooxy (AN) group; and/or one or more amino acid residues (such as alanine and/or glycine), preferably a dipeptide or tripeptide residue (e.g. comprising alanine and/or glycine).

The linker X may comprise terminal functional groups such as carboxylic acid and/or amine, to facilitate linking to Y' and/or PHG. Thus X may for example comprise a terminal amine which forms an amide link with a terminal carboxylic acid group of PHG, and/or a terminal carboxylic acid group which forms an amide link with a terminal amine group of Y'. When X is an amino acid or peptide residue, the terminal amine and carboxylic acid groups may be used to link to PHG and Y'. Suitable examples of X which comprise a hydrocarbyl group, such as an alkyl group, include amino carboxylic acids, such as a $C_3$-$C_{12}$ amino carboxylic acid, preferably a $C_3$-$C_{10}$ amino carboxylic acid. The amino carboxylic acid maybe a $C_3$-$C_{12}$ or $C_3$-$C_{10}$ saturated carboxylic acid, for example aminohexanoic acid, aminoheptanoic acid or aminooctanoic acid.

The structural lipid of formula (I) is preferably contained in the lipid nanoparticle in an amount of from about 10 to about 50 mol %, such as from about 20 to about 40 mol %, preferably from about 20 to about 35 mol %, further preferably from about 25 to about 35 mol %. Without wishing to be bound by theory, when the structural lipid is present in such amounts this may contribute to an improved stability-temperature release profile, as discussed below.

Magnetic Resonance Imaging (MRI) Label

In one embodiment, the structural lipid of formula (I) comprises a magnetic resonance imaging (MRI) label. Thus the structural lipid of formula (I) can comprise a paramagnetic metal lipid. This component can provide imaging functionality to the lipid nanoparticle, as well as structural functionality. This means that the lipid nanoparticle may be useful, for example, for diagnostic purposes.

The paramagnetic metal lipid may comprise, for example, a paramagnetic metal suitable for MRI, e.g. chelated to the head group PHG of the above formula (I). Thus the paramagnetic metal lipid may have the following general structure:

(I)

wherein R and R' are long hydrocarbyl hydrophobic chains, Y is a linker element, and PHG is a polar head group described as large according to its van der Waals radius, for example having a diameter (as described above for the phospholipid) of greater than about 3 Å, preferably greater than about 5 Å, more preferably from about 5 to about 15 Å, and/or a molecular weight of greater than 200, preferably greater than 300, more preferably from 400 to 3000. Alternatively, the PHG may have a diameter of from about 3 to about 5 Å.

PHG may be as described above for the structural lipid of formula (I). Typically, PHG is an optionally substituted poly(aminocarboxylate) group, such as DTPA or DOTA, comprising a paramagnetic metal suitable for MRI. The hydrophobic hydrocarbon chain may be, for example, an alkyl group, preferably a $C_{12}$-$C_{20}$ (preferably saturated) alkyl group, more preferably a $C_{14}$-$C_{20}$ (preferably saturated) alkyl group. The linker Y preferably comprises an amide functional group.

The group represented by YRR' may correspond to a lipid moiety which may comprise, for example, one or more alkyl groups, preferably $C_{12}$-$C_{20}$ (preferably saturated) alkyl groups, more preferably $C_{14}$-$C_{20}$ (preferably saturated) alkyl groups. A suitable lipid moiety comprising alkyl groups may comprise a N,N-di($C_{12}$-$C_{20}$ saturated lipid) methylamine, such as N,N-distearylamidomethylamine (DSA). Alternatively, the lipid moiety may comprise a phospholipid, such as a phosphatidylethanolamine.

The paramagnetic metal may be, for example, Gd, or radiometals such as $^{64}Cu$. Preferably, the paramagnetic metal is gadolinium (Gd).

In one preferred embodiment, the gadolinium lipid comprises DSA. Thus in one preferred embodiment, the gadolinium lipid comprises Gd.DOTA.DSA and/or Gd.DTPA.DSA, preferably Gd.DOTA.DSA, as shown below (where the top structure corresponds to DSA and the bottom structures represent Gd.DOTA and Gd.DTPA):

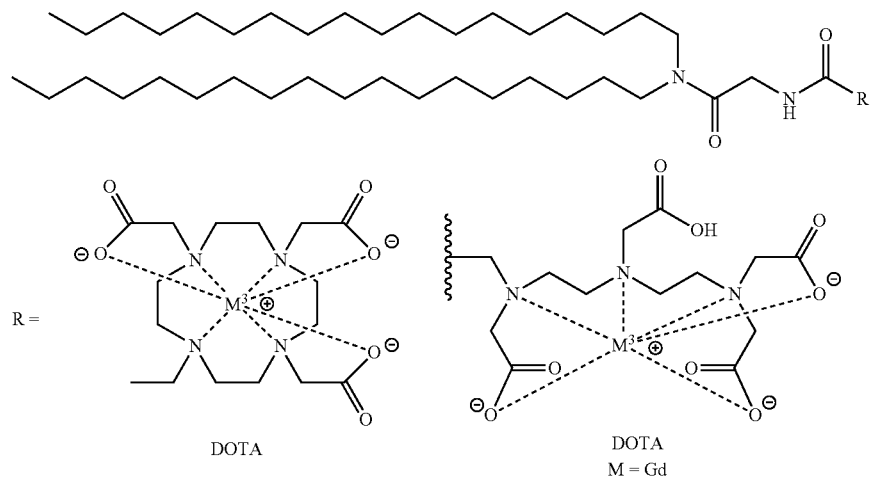

In other embodiments, the linker Y preferably comprises a group X-Y', for example such that the paramagnetic metal lipid (preferably a gadolinium lipid) of formula (I) is a lipid of formula (II):

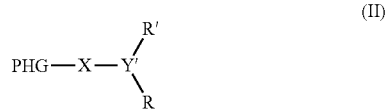

(II)

wherein PHG, R and R' are as described above for formula (I), Y' is a linker element and X is a further linker which extends the distance between PHG and the hydrocarbyl chains R and R'.

The linker Y' preferably comprises a terminal functional group which may react with a terminal functional group of the linker X. For example, the linker Y' may comprise a terminal carboxylic acid group which reacts with a terminal amine group of X to form an amide link, or alternatively the linker Y' may comprise a terminal amine group which reacts with a terminal carboxylic acid group of X to form an amide link. In one preferred embodiment, Y' comprises an amide functional group, such as an amidomethylamine group (wherein the terminal amine forms an amide link with a terminal carboxylic acid group of X). The group represented by Y'RR' may thus correspond to a lipid moiety which may comprise, for example, one or more alkyl groups, preferably $C_{12}$-$C_{20}$ (preferably saturated) alkyl groups, more preferably $C_{14}$-$C_{20}$ (preferably saturated) alkyl groups as described above. A suitable lipid moiety comprising alkyl groups may comprise a N,N-di($C_{12}$-$C_{20}$ saturated lipid) amidomethylamine; such as N,N-distearylamidomethylamine (DSA).

The further linker X is preferably an organic linker group having a linear chain length of from 3 to 40 atoms (for example including, but not limited to, carbon, oxygen and/or nitrogen atoms). For example, the further linker X may comprise a hydrocarbyl chain, or may comprise carbon atoms and further functional groups such as ether, carboxyl, amine, amide or hydroxyl groups. Preferably X comprises a hydrocarbyl chain of from 3 to 12 carbon atoms, preferably from 3 to 10 carbon atoms, preferably a $C_3$-$C_{12}$ alkyl group (such as a $C_3$-$C_{12}$ saturated alkyl group), more preferably a $C_3$-$C_{10}$ alkyl group (such as a $C_3$-$C_{10}$ saturated alkyl group); a polyethylene glycol group (PEG) group, in particular a PEG oligomer having for example from 2 to 10 ethylene oxide repeat units; one or more (e.g. one or two) aminooxy (AN) group; and/or one or more amino acid residues (such as alanine and/or glycine), preferably a dipeptide or tripeptide residue (e.g. comprising alanine and/or glycine).

The linker X may comprise terminal functional groups such as carboxylic acid and/or amine, to facilitate linking to Y' and/or PHG. Thus X may for example comprise a terminal amine which forms an amide link with a terminal carboxylic acid group of PHG, and/or a terminal carboxylic acid group which forms an amide link with a terminal amine group of Y'. When X is an amino acid or peptide residue, the terminal amine and carboxylic acid groups may be used to link to PHG and Y'. Suitable examples of X which comprise a hydrocarbyl group, such as an alkyl group, include amino carboxylic acids, such as a $C_3$-$C_{12}$ amino carboxylic acid, preferably a $C_3$-$C_{10}$ amino carboxylic acid. The amino carboxylic acid maybe a $C_3$-$C_{12}$ or $C_3$-$C_{10}$ saturated carboxylic acid, for example aminohexanoic acid, aminoheptanoic acid or aminooctanoic acid.

In preferred embodiments of the paramagnetic lipid of formula (II), PHG comprises Gd.DOTA or Gd.DOTA and/or Y'RR' comprises a or a N,N-di($C_{12}$-$C_{20}$ saturated lipid) amidomethylamine, such as N,N-distearylamidomethylamine (DSA).

The inclusion of a "chain-extended" linker group X-Y' in a gadolinium lipid can provide improved contrast agents for in vivo MRI. The inventors consider that the further linker X increases the distance between the gadolinium and the hydrophobic "tails" R and R'. This in turn increases the distance between the gadolinium and the liposome surface. The effect may provide improved relaxivity.

Specific examples are shown below:

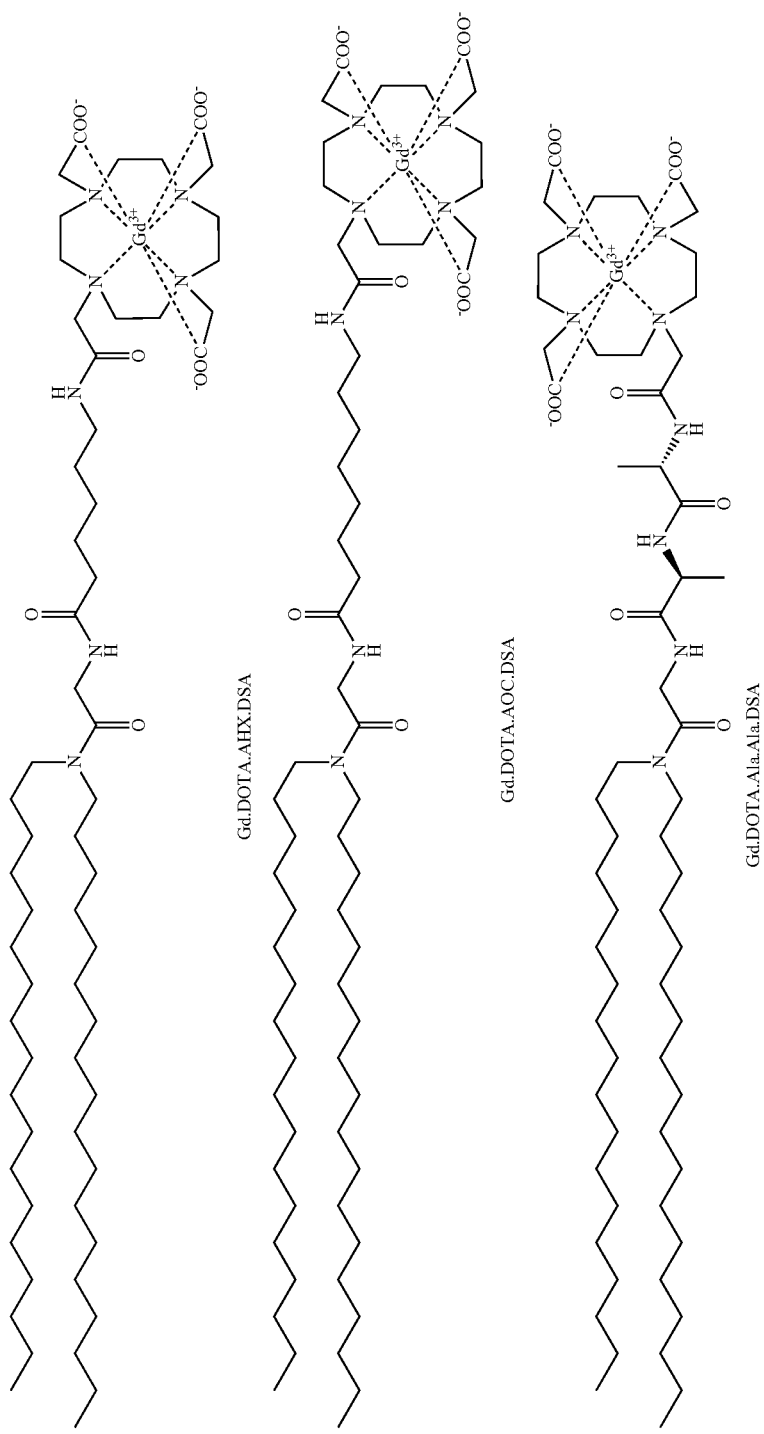

-continued
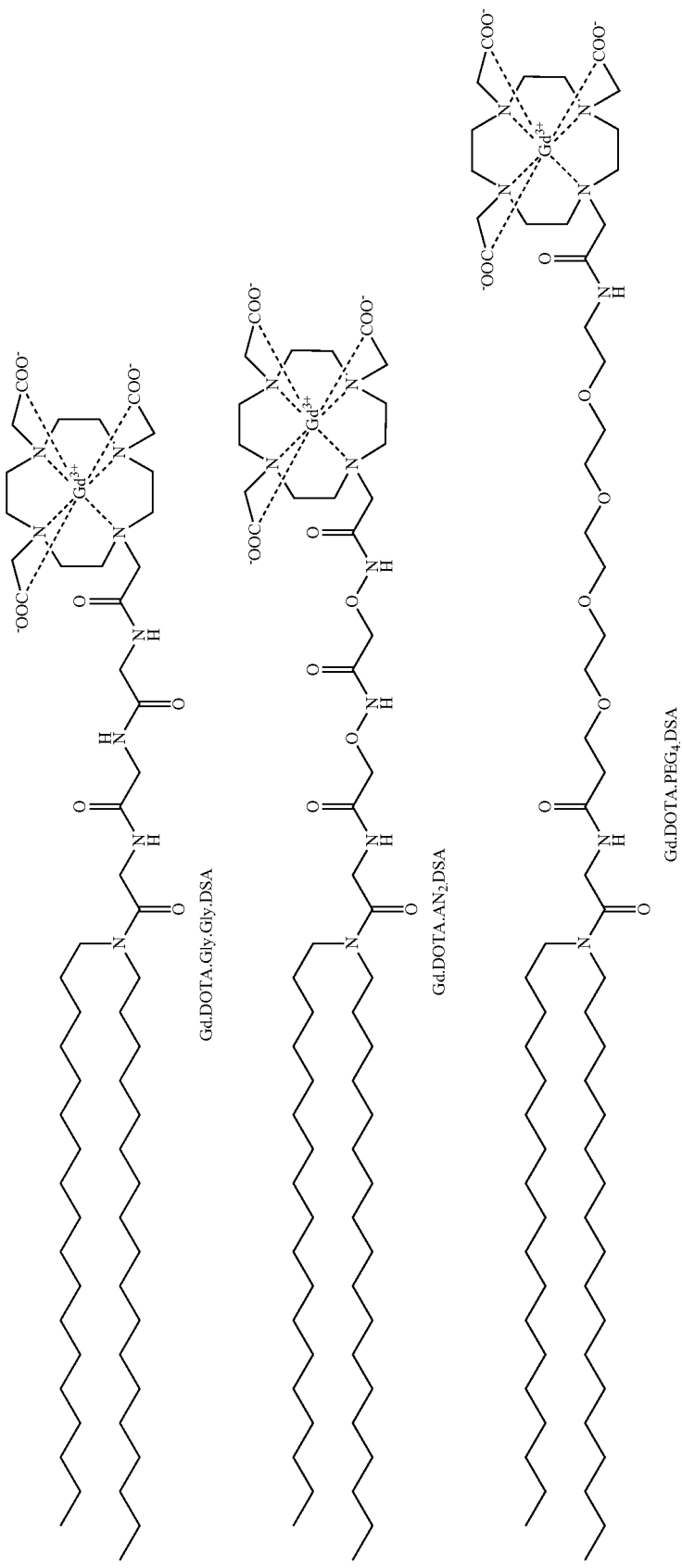
Gd.DOTA.Gly.Gly.DSA
Gd.DOTA.AN₂.DSA
Gd.DOTA.PEG₄.DSA

Preferably, the MRI label comprises a gadolinium lipid selected from gadolinium (III) 6,9-bis(carboxylatomethyl)-3-(2-(octadecylamino)-2-oxoethyl)-11-oxo-3,6,9,12-tetraazatriacontanoate (Gd-DTPA-bis(stearylamide); Gd-BSA, or Gd.DTPA.BSA); gadolinium (III) 6,9-bis(carboxylatomethyl)-11-oxo-3-(2-oxo-2-(tetradecylamino)ethyl)-3,6,9,12-tetraazahexacosanoate (Gd-DTPA-bis(myrisitylamide); GdDTPA-BMA, or Gd.DTPA.BMA); 1,2-dimyristoyl-sn-glycero-3-phosphoethanolaminediethylene-triamine-pentaacetate:$Gd^{3+}$ (DMPEDTPA:$Gd^{3+}$, or Gd.DTPA.DMP); D35-1,2-dihexanoyl-sn-glycero-3-phosphocholine; gadolinium (III) 2-{4,7-bis-carboxymethyl-10-[(N,N-distearylamidomethyl-N'-amido-methyl]-1,4,7,10-tetra-azacyclododec-1-yl}-acetic acid (Gd.DOTA.DSA, also known as gadolinium (III) 2,2',2''-(10-(2-((2-(dioctadecylamino)-2-oxoethyl)amino)-2-oxoethyl)-1,4,7,10-tetraazacyclododecane-1,4,7-triyl)triacetate); gadolinium (III) 2-(1-[(N,N-distearyl-amidomethyl)-N'-amidomethyl]-4,7,7-tris-carboxymethyl-1,4,7-triaza-sept-1-yl) acetic acid (Gd.DTPA.DSA, also known as gadolinium (III) 3,6,9-tris(carboxylatomethyl)-15-octadecyl-11,14-dioxo-3,6,9,12,15-pentaazatritriacontanoate); gadolinium (III) 1,4,7,10-tetraazacyclododecane-1,4,7,10-tetraacetic acid mono($N^1$-distearoylphosphatidylethanolamine)amide (Gd.DOTA.DSPE, also known as gadolinium (III) 2,2',2''-(10-(2-((2-((((R)-2,3-bis(stearoyloxy)propoxy)(hydroxy)phosphoryl)oxy)ethyl)amino)-2-oxoethyl)-1,4,7,10-tetraazacyclododecane-1,4,7-triyl)triacetate); gadolinium (III) 2,2',2''-(10-(2-((6-((2-(dioctadecylamino)-2-oxoethyl)amino)-6-oxohexyl)amino)-2-oxoethyl)-1,4,7,10-tetraazacyclododecane-1,4,7-triyl)triacetate (Gd.DOTA.AHX.DSA); gadolinium (III) 2,2',2''-(10-(2-((8-((2-(dioctadecylamino)-2-oxoethyl)amino)-8-oxooctyl)amino)-2-oxoethyl)-1,4,7,10-tetraazacyclododecane-1,4,7-triyl)triacetate (Gd.DOTA.AOC.DSA); gadolinium (III) 2,2',2''-(10-((4S,7S)-4,7-dimethyl-12-octadecyl-2,5,8,11-tetraoxo-3,6,9,12-tetraazatriacontyl)-1,4,7,10-tetraazacyclododecane-1,4,7-triyl)triacetate (Gd.DOTA.Ala.Ala.DSA), gadolinium (III) 2,2',2''-(10-(12-octadecyl-2,5,8,11-tetraoxo-3,6,9,12-tetraazatriacontyl)-1,4,7,10-tetraazacyclododecane-1,4,7-triyl)triacetate (Gd.DOTA.Gly.Gly.DSA); gadolinium (III) 2,2',2''-(10-(14-octadecyl-2,6,10,13-tetraoxo-4,8-dioxa-3,7,11,14-tetraazadotriacontyl)-1,4,7,10-tetraazacyclododecane-1,4,7-triyl)triacetate (Gd.DOTA.$AN_2$.DSA); and gadolinium (III) 2,2',2''-(10-(22-octadecyl-2,18,21-trioxo-6,9,12,15-tetraoxa-3,19,22-triazatetracontyl)-1,4,7,10-tetraazacyclododecane-1,4,7-triyl)triacetate (Gd.DOTA.$PEG_4$.DSA).

When the structural lipid of formula (I) (or formula (II)) comprises an MRI label, it is preferably contained in the lipid nanoparticle in an amount sufficient for MRI imaging, suitably from about 10 to about 50 mol %, such as from about 20 to about 40 mol %, preferably from about 20 to about 35 mol %, further preferably from about 25 to about 35 mol %. Without wishing to be bound by theory, when the MRI lipid is present in such amounts this may also contribute to an improved stability-temperature release profile, as discussed below.

Thermosensitivity

In one embodiment, the lipid nanoparticle of the present invention is thermosensitive, i.e. undergoes a phase transition at a particular temperature. Typically, the thermosensitive lipid nanoparticle of the present invention is thermosensitive at a temperature of from 39.0° C. to 45.0° C., preferably from 39.0° C. to 43.0° C., more preferably from 40.0° C. to 41.0° C.

The thermosensitivity of the lipid nanoparticle is affected by the nature and proportion of the components (in particular the lipid components) making up the lipid nanoparticle. For example, the thermosensitivity may depend on the nature and ratio of the phospholipid, lysolipid, phospholipid comprising a hydrophilic polymer and structural lipid of formula (I) (or formula (II)), as well as any other, non-functional, lipids. The skilled person would be able to determine effective formulations which show thermosensitivity at the desired temperature. In particular, by selecting the preferred lipids and preferred amounts discussed above, the skilled person would be able to arrive at a thermosensitive lipid nanoparticle having thermosensitivity at the desired temperature.

The thermosensitive lipid nanoparticles of the present invention may be advantageous because they have an improved stability-temperature release profile, having improved thermal stability below a critical temperature (i.e. the temperature at which the lipid nanoparticles become thermosensitive) and providing a rapid release of lipid nanoparticle content on reaching the critical temperature, i.e. a "sharp" temperature release profile. For example, the thermosensitive lipid nanoparticles of the present invention may show improved serum stability at about 37° C. to below 39° C., particularly at about 37° C. Such improved stability can mean that any release of lipid nanoparticle content at these temperatures is reduced. The lipid nanoparticle content can be substantially retained within the lipid nanoparticle at these temperatures, i.e. the thermosensitive lipid nanoparticles are not "leaky". The lipid nanoparticles may also show an improved release, for example in terms of reduced time taken for content to be released and/or increased amount of content released, at the critical temperatures described above, i.e. from 39.0° C. to 45.0° C., preferably from 39.0° C. to 43.0° C., more preferably from 40.0° C. to 41.0° C.

Near Infrared Fluorescence (NIRF) Imaging Label

In one embodiment, the lipid nanoparticle of the present invention may further comprise an NIRF imaging label, for example comprising a near infrared fluorescence (NIRF) imaging agent comprising (e.g. conjugated to) a lipid, such as a fatty acid. The NIRF imaging label may provide imaging and/or diagnostic functionality to the lipid nanoparticle, as well as structural functionality.

In one embodiment, the NIRF imaging label provides the only imaging functionality in the lipid nanoparticle. In alternative embodiments, the NIRF imaging agent may be combined with other types of imaging functionality, such as MRI. Thus, for example, the NIRF imaging label may be present in addition to an MRI label as described above, and/or one or more of the other labels described below.

The NIRF imaging label may be present as a lipid component (e.g. forming part of the lipid bilayer). Alternatively, the lipid nanoparticles may comprise the NIRF imaging label encapsulated within the lipid nanoparticle (i.e. inside the liposome).

In one embodiment, the NIRF imaging label may have the following general structure:

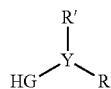

wherein R and R' are hydrogen or long hydrocarbyl hydrophobic chains (provided that at least one of R and R' are is a long hydrocarbyl hydrophobic chain), Y is a linker element, preferably an amide group, and HG is a head group. Preferably, HG is a polar head group PHG, preferably a PHG described as large according to its van der Waals radius, for example having a diameter (as described above for the phospholipid) of greater than about 3 Å, preferably greater than about 5 Å, more preferably from about 5 to about 15 Å, and/or a molecular weight of greater than 200, preferably greater than 300, more preferably from 400 to 3000. Alternatively, the PHG may have a diameter of from about 3 to about 5 Å. Typically, HG or PHG comprises the NIRF imaging agent.

The group represented by YRR' may correspond to a lipid moiety which may comprise, for example, one or more alkyl groups, preferably $C_{12}$-$C_{20}$ (preferably saturated) alkyl groups, more preferably $C_{14}$-$C_{20}$ (preferably saturated) alkyl groups. This group may correspond to the lipid of the NIRF imaging agent comprising a lipid. Preferably, the lipid comprises a NA-di($C_{12}$-$C_{20}$ saturated lipid)methylamine or a NA-di($C_{12}$-$C_{20}$ saturated lipid) amidomethylamine. In one preferred embodiment, the lipid comprises N,N-distearylamidomethylamine (DSA).

In another embodiment, the linker Y preferably comprises a group X-Y', for example such that the NIRF imaging label has the following structure:

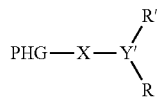

wherein PHG, R and R' are as described above, Y' is a linker element, X is a further linker which extends the distance between PHG and the hydrocarbyl chains R and R', and Y' and X are as described above for the structural lipid of formula (II).

The NIRF imaging agent may be any suitable imaging moiety for NIRF. Suitable examples are XenoLight750™, IRDye™ 800CW, TTO680™ or DyLight 680™. This group may correspond to PHG in the structure above. Examples of the structures of some of these NIRF imaging agent components of the NIRF imaging label are shown below:

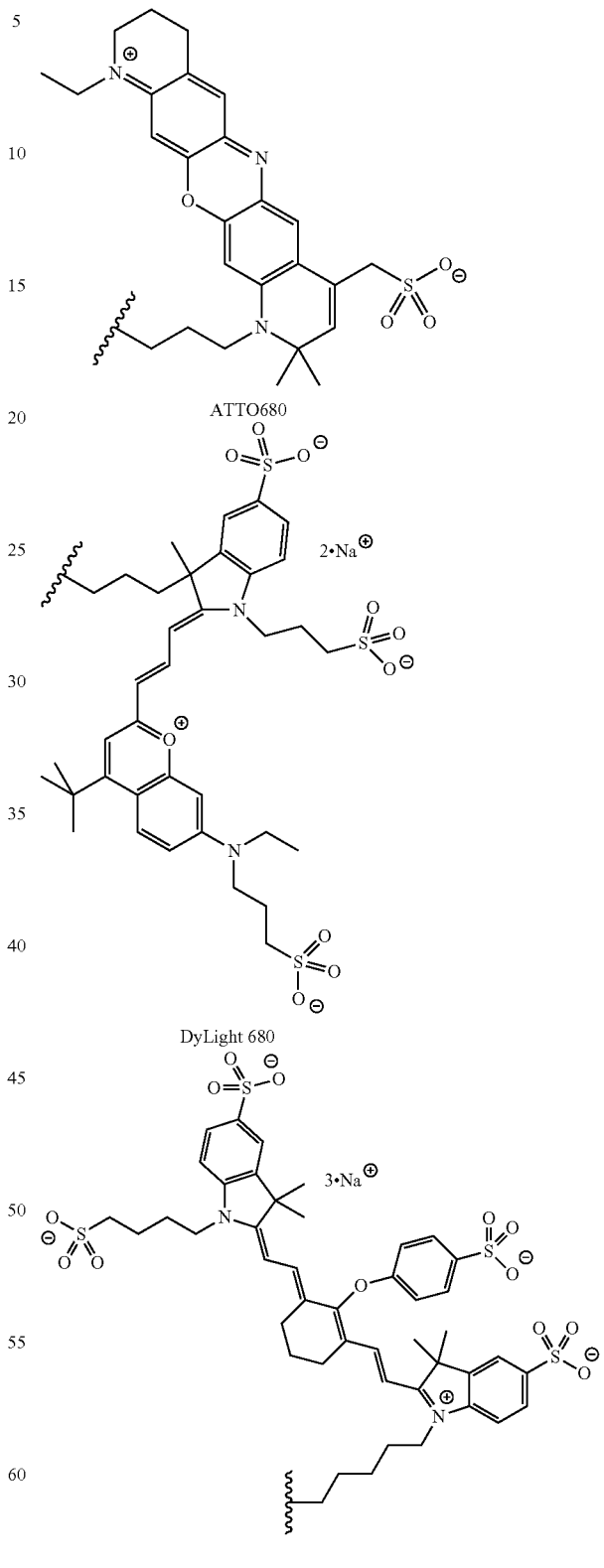

Thus preferred NIRF imaging agents according to the present invention comprise DSA:

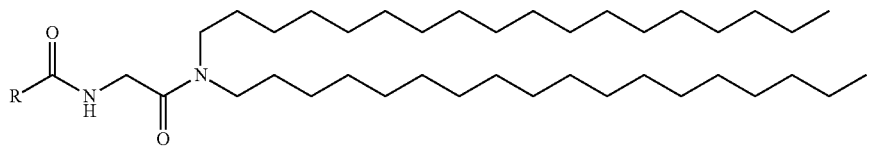

wherein R is IRDye™ 800CW, ATTO680™ or DyLight 680™ as shown above, or R is XenoLight750™.

A preferred NIRF imaging agent according to the present invention is N-XenoLight750-N,N-distearylamidomethylamine (XL750.DSA).

The NIRF imaging label is preferably contained in the lipid nanoparticle in an amount of from about 0.001 to about 10 mol %, preferably about 0.01 to about 10.0 mol %, about 0.01 to about 1 mol %, preferably from about 0.01 to about 0.3 mol %, e.g. about 0.05 mol %.

Preferred Lipid Nanoparticles

The phospholipid (i) and the structural lipid (iv) of formula (I) (or formula (II)) typically together comprise 80 mol % or more of the lipid nanoparticle. The combination of these lipids renders the lipid nanoparticle of the present invention stable to drug encapsulation and, when imaging lipids are present, to multi-modal imaging (hence theranostic).

In one embodiment, preferably the molar ratio of (i) phospholipid:(ii) lysolipid:(iii) phospholipid comprising a hydrophilic polymer:(iv) structural lipid of formula (I) (or formula (II)) is about (i) 30-90:(ii) 2-15:(iii) 4 or 5-10:(iv) 10-50, preferably about (i) 40-75:(ii) 3-10:(iii) 6-8: (iv) 20-40. Preferably the lipid nanoparticle comprises about 5 or 6-8 mol % of PEG$^{2000}$-DSPE, and/or comprises a first phosphatidylcholine in an amount of from about 40-70 mol %, preferably 45-55 mol %, and a second phosphatidylcholine in an amount of from about 0-10 mol %, preferably 2-8 mol %. The same preferred ratios apply when the structural lipid of formula (I) comprises a magnetic resonance imaging (MRI) label.

In another embodiment, the lipid nanoparticle of the present invention preferably comprises the structural lipid of formula (I) (or formula (II)) in an amount of about 10-50 mol %, preferably about 20-40 mol %, more preferably about 20-35 mol %, e.g. about 25-35 mol %, preferably wherein the amounts of the other components are as described above. Thus preferably, the lipid nanoparticle of the present invention may comprise an MRI label as described herein in an amount of about 10-50 mol %, preferably about 20-40 mol %, more preferably about 20-35 mol %, e.g. about 25-35 mol %, preferably wherein the amounts of the other components are as described above.

In another embodiment, the lipid nanoparticle comprises a near infrared fluorescence (NIRF) imaging label, and the molar ratio of (i) phospholipid:(ii) lysolipid:(iii) phospholipid comprising a hydrophilic polymer:(iv) structural lipid of formula (I) (or formula (II)):(v) NIRF imaging label is about (i) 30-90:(ii) 2-15:(iii) 4 or 5-10:(iv) 10-50:(v) 0.001-10, preferably about (i) 40-75:(ii) 3-10:(iii) 5 or 6-8:(iv) 20-40:(v) 0.01-1. The present invention further relates to such lipid nanoparticles comprising an NIRF imaging label wherein the structural lipid of formula (I) (or formula (II)) is contained in an amount of about 10-50 mol %, preferably about 20-40 mol %, more preferably about 20-35 mol %, e.g. about 25-35 mol %, preferably wherein the amounts of the other components are as described above.

In one preferred embodiment, the lipid nanoparticle comprise an MRI label and an NIRF imaging label. In this embodiment, preferably the molar ratio of (i) phospholipid:(ii) lysolipid:(iii) phospholipid comprising a hydrophilic polymer:(iv) MRI label:(v) NIRF imaging label is about (i) 30-90:(ii) 2-15:(iii) 4 or 5-10:(iv) 10-50:(v) 0.001-10, preferably about (i) 40-75:(ii) 3-10:(iii) 5 or 6-8:(iv) 20-40:(v) 0.01-1. The present invention further relates to such lipid nanoparticles comprising an NIRF imaging label wherein the MRI label is contained in an amount of about 10-50 mol %, preferably about 20-40 mol %, more preferably about 20-35 mol %, e.g. about 25-35 mol %, preferably wherein the amounts of the other components are as described above.

In certain embodiments, the present invention may relate to a lipid nanoparticle comprising one or more of the following preferred components:
(i) at least one phosphatidylcholine;
(ii) at least one lysolipid;
(iii) at least one PEGylated phospholipid;
(iv) an MRI label comprising a gadolinium lipid, preferably a gadolinium lipid of formula (I) or (II) as described above, more preferably wherein PHG is an (optionally substituted) poly(amino carboxylate) group comprising gadolinium, R and R' are each independently a $C_{12}$-$C_{20}$ (preferably saturated) alkyl group, the linker Y or Y' comprises an amide functional group and the optional linker X comprises a $C_3$-$C_{12}$ alkyl group (such as a $C_3$-$C_{12}$ amino carboxylic acid group), a polyethylene glycol group, one or more aminoxy groups and/or one or more amino acid residues; and/or
(v) a near infrared fluorescence (NIRF) imaging label;
preferably wherein the amounts of components (i) to (v) correspond to the molar ratios described above.

For example, a preferred lipid nanoparticle according to the present invention may comprise:
(i) a 1,2-di($C_{12}$-$C_{20}$ saturated lipid)-sn-glycero-3-phosphocholine, wherein the saturated lipid groups can be the same or different from each other;
(ii) a 1-($C_{12}$-$C_{20}$ saturated lipid)-sn-glycero-3-phosphocholine;
(iii) a PEGylated phospholipid, wherein the phospholipid comprises a 1-($C_{12}$-$C_{20}$ saturated lipid)-sn-glycero-3-phosphoethanolamine;
(iv) an MRI label comprising a gadolinium lipid, preferably a gadolinium lipid of formula (I) or (II) as described above, for example selected from gadolinium (III) 6,9-bis (carboxylatomethyl)-3-(2-(octadecylamino)-2-oxoethyl)-11-oxo-3,6,9,12-tetraazatriacontanoate (Gd-DTPA-bis (stearylamide); Gd-BSA, or Gd.DTPA.BSA); gadolinium (III) 6,9-bis(carboxylatomethyl)-11-oxo-3-(2-oxo-2-(tetradecylamino)ethyl)-3,6,9,12-tetraazahexacosanoate (Gd-DTPA-bis(myrisitylamide); GdDTPA-BMA, or Gd.DTPA.BMA); 1,2-dimyristoyl-sn-glycero-3-phosphoethanolaminediethylene-triamine-pentaacetate: $Gd^{3+}$ (DMPEDTPA:$Gd^{3+}$, or Gd.DTPA.DMP); D35-1,2-dihexanoyl-sn-glycero-3-phosphocholine; gadolinium (III) 2-{4,7-bis-carboxymethyl-10-[(N,N-distearylamidomethyl-N'-amido-methyl]-1,4,7,10-tetra-azacyclododec-1-yl}-acetic acid (Gd.DOTA.DSA, also known as gadolinium (III) 2,2',2"-(10-(2-((2-(dioctadecylamino)-2-oxoethyl)amino)-2-oxoethyl)-1,4,7,10-tetraazacyclododecane-1,4,7-triyl)triacetate); gadolinium (III) 2-(1-[(N,N-distearyl-amidomethyl]-N'-amidomethyl]-4,7,7-tris-carboxymethyl-1,4,7-triaza-sept-1-yl) acetic acid (Gd.DTPA.DSA, also known as gadolinium (III) 3,6,9-tris(carboxylatomethyl)-15-octadecyl-11,14-dioxo-3,6,9,12,15-pentaazatritriacontanoate); gadolinium (III) 1,4,7,10-tetraazacyclododecane-1,4,7,10-tetraacetic acid mono($N^1$-distearoylphosphatidylethanolamine)amide (Gd.DOTA.DSPE, also known as gadolinium (III) 2,2',2"-(10-(2-((2-((((R)-2,3-bis(stearoyloxy)propoxy)(hydroxy)phosphoryl)oxy)ethyl)amino)-2-oxoethyl)-1,4,7,10-tetraazacyclododecane-1,4,7-triyl) triacetate); gadolinium (III) 2,2',2"-(10-(2-((6-((2-(dioctadecylamino)-2-oxoethyl)amino)-6-oxohexyl)amino)-2-oxoethyl)-1,4,7,10-tetraazacyclododecane-1,4,7-triyl) triacetate (Gd.DOTA.AHX.DSA); gadolinium (III) 2,2',2"-(10-(2-((8-((2-(dioctadecylamino)-2-oxoethyl)amino)-8-oxooctyl)amino)-2-oxoethyl)-1,4,7,10-tetraazacyclododecane-1,4,7-triyl)triacetate (Gd.DOTA.AOC.DSA); gadolinium (III) 2,2',2"-(10-((4S,7S)-4,7-dimethyl-12-octadecyl-2,5,8,11-tetraoxo-3,6,9,12-tetraazatriacontyl)-1,4,7,10-tetraazacyclododecane-1,4,7-triyl)triacetate (Gd.DOTA.Ala.Ala.DSA), gadolinium (III) 2,2',2"-(10-(12-octadecyl-2,5,8,11-tetraoxo-3,6,9,12-tetraazatriacontyl)-1,4,7,10-tetraazacyclododecane-1,4,7-triyl) triacetate (Gd.DOTA.Gly.Gly.DSA); gadolinium (III) 2,2',2"-(10-(14-octadecyl-2,6,10,13-tetraoxo-4,8-dioxa-3,7,11,14-tetraazadotriacontyl)-1,4,7,10-tetraazacyclododecane-1,4,7-triyl)triacetate (Gd.DOTA.$AN_2$.DSA); and gadolinium (III) 2,2',2"-(10-(22-octadecyl-2,18,21-trioxo-6,9,12,15-tetraoxa-3,19,22-triazatetracontyl)-1,4,7,10-tetraazacyclododecane-1,4,7-triyl)triacetate (Gd.DOTA.$PEG_4$.DSA);

(v) a near infrared fluorescence (NIRF) imaging agent comprising a lipid, such as a fatty acid;

preferably wherein the amounts of components (i) to (v) correspond to the molar ratios described above.

A further preferred lipid nanoparticle according to the present invention may comprise one or more of the following preferred components:

(i) DPPC and DSPC;
(ii) MSPC;
(iii) $PEG^{2000}$-DSPE;
(iv) Gd.DOTA.DSA, Gd.DTPA.DSA, Gd.DOTA.AHX.DSA and/or Gd.DOTA.AOC.DSA; and/or
(v) a near infrared fluorescence (NIRF) imaging agent comprising a N,N-di($C_{12}$-$C_{20}$ saturated lipid)methylamine;

preferably wherein the amounts of components (i) to (v) correspond to the molar ratios described above; more preferably wherein DPPC is present in an amount of from about 40-70 mol %, preferably 45-55 mol %, and DSPC is present in an amount of from about 0.1-10 mol %, preferably 2-8 mol %, and/or $PEG^{2000}$-DSPE is present in an amount of from about 6-8 mol %, preferably from about 6-6.5 mol %, and/or MSPC is present in an amount of about 5 mol %.

Suitably the lipid nanoparticle may comprise one or more of the following preferred components:

(i) DPPC and DSPC;
(ii) MSPC;
(iii) $PEG^{2000}$-DSPE;
(iv) Gd.DOTA.DSA, Gd.DOTA.AHX.DSA and/or Gd.DOTA.AOC.DSA; and/or
(v) XL750.DSA;

preferably wherein the amounts of components (i) to (v) correspond to the molar ratios described above; more preferably comprising DPPC:DSPC:MSPC:$PEG^{2000}$-DSPE:Gd.DOTA.DSA:XL750.DSA in a molar ratio of 54:5:5:6:30:0.05.

Preparation

The basic structure of the lipid nanoparticles (in particular, the liposomes) may be made by a variety of techniques known in the art.

For example, lipid nanoparticles have typically been prepared using a process whereby lipids suspended in organic solvent are evaporated under reduced pressure to a dry film in a reaction vessel. An appropriate amount of aqueous phase is then added to the vessel to hydrate the dry film. After 5 freeze thaw cycles, sonication at 60° C., extrusion through a polycarbonate membrane (100 nm) at 55° C., followed by final buffer exchange as required, lipid nanoparticles are ready for use.

Lipid nanoparticles may also be reproducibly prepared using a number of currently available techniques that are known in the art. The types of lipid nanoparticles which may be produced using a number of these techniques include small unilamellar vesicles (SUVs), reverse-phase evaporation vesicles (REV) and stable plurilamellar vesicles (SPLV).

The lipid nanoparticles according to the present invention may be formulated with one or more active pharmaceutical ingredients (APIs) as described below.

Further Components

It may also be desirable to include other ingredients in the lipid nanoparticle, such diagnostic markers including radiolabels, dyes, chemiluminescent and fluorescent markers; contrasting media; imaging aids; targeting agents and so forth.

Preferably the lipid nanoparticle does not comprise cholesterol, since this typically imparts too much rigidity to the lipid nanoparticle.

In one embodiment the lipid nanoparticle of the present invention may further comprise a targeting agent, for example comprising an antibody, diabody, nanobody, aptamer or peptide. For example, the targeting agent may be selected from folic acid (folate); antibodies (such as Trastuzumab or cetuximab); peptides (such as octreotide, LHRH antagonists or uPAR specific peptides); transferrin; mannose and galactose for asialoglycoprotein receptors; and aptamers.

The targeting agent may be a tumour targeting agent. The tumour targeting agent may comprise, for example, a ligand for a receptor that is over-expressed in tumour cells relative to the expression of said receptors in the cells of non-tumourous tissue of mammals, such as a folate moiety. For example, the tumour targeting agent may be a phospholipid-polyethylene glycol-folate compound, such as folate-$PEG^{2000}$-DSPE [distearoylphosphatidylethanolamine-polyethylene glycol 2000-folate]. The amount of the folate moiety present in the lipid nanoparticle is suitably from about 1-2 mol % of the total lipid nanoparticle formulation.

In one aspect further lipids suitable for use in imaging applications may incorporated in the lipid nanoparticle. Thus the lipid nanoparticle of the present invention may further comprise one or more further imaging agents, such as an imaging lipid selected from fluorescent lipids, nuclear magnetic resonance imaging lipids, electron microscopy and image processing lipids, electron spin resonance lipids and radioimaging lipids. The further imaging agent may also be a positron emission tomography (PET) or single-photon emission computed tomography (SPECT) imaging agent. Suitable and preferred lipids in each of these classes are given below.

Fluorescent Lipids

Examples of fluorescent lipids are 1,2-dioleoyl-sn-glycero-3-Phosphoethanolamine-N-(5-dimethylamino-1-naphthalenesulfonyl), 1,2-dioleoyl-sn-glycero-3-phosphoethanolamine-N-(1-pyrenesulfonyl), 1,2-dioleoyl-sn-glycero-3-phosphoethanolamine-N-(carboxyfluorescein), 1-oleoyl-2-[6-[(7-nitro-2-1,3-benzoxadiazol-4-yl)amino]hexanoyl]-sn-glycero-3-phospho-L-serine, 25-{N-[(7-nitrobenz-2-oxa-1,3-diazol-4-yl)-methyl]amino}-27-norcholesterol, -oleoyl-2-[6-[(7-nitro-2-1,3-benzoxadiazol-4-yl)amino]hexanoyl]-sn-glycero-3-phosphoethanolamine and 1,2-dioleoyl-sn-glycero-3-phosphoethanolamine-N-(lissamine rhodamine B sulfonyl).

Magnetic Resonance Imaging

As an alternative to, or in addition to, the MRI label described above as an optional embodiment of the structural lipid (iv) of formula (I) (or formula (II)), the lipid nanoparticle of the present invention may comprise a lipid for magnetic resonance imaging (MRI).

The lipid for MRI may be present as a lipid component (e.g. forming part of the lipid bilayer). Alternatively, the lipid nanoparticles may comprise the lipid for MRI encapsulated within the lipid nanoparticle (i.e. inside the liposome).

Such an MRI lipid may comprise, for example, a paramagnetic metal suitable for MRI, e.g. chelated to a head group, preferably an optionally substituted poly(aminocarboxylate) group, such as DTPA or DOTA. The head group (preferably poly(aminocarboxylate)) chelate may be used as it is, or alternatively may be conjugated to one or more hydrophobic hydrocarbon chains via a linker For example, the paramagnetic metal lipid may have the following general structure:

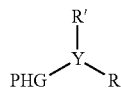

wherein R and R' are hydrogen or long hydrocarbyl hydrophobic chains (provided that at least one of R and R' are is a long hydrocarbyl hydrophobic chain), Y is a linker element, and PHG is a polar head group, preferably described as large according to its van der Waals radius, for example having a diameter (as described above for the phospholipid) of greater than about 3 Å, preferably greater than about 5 Å, more preferably from about 5 to about 15 Å, and/or a molecular weight of greater than 200, preferably greater than 300, more preferably from 400 to 3000. Alternatively, the PHG may have a diameter of from about 3 to about 5 Å.

Typically, PHG is as described above.

The group represented by YRR' may be as described above. For example in one embodiment, the linker group Y preferably comprises a group X-Y', wherein Y' is a linker element and X is a further linker which extends the distance between PHG and the hydrocarbyl chains R and R', as described above.

The paramagnetic metal may be, for example, Gd, or radiometals such as $^{64}$Cu. Preferably, the paramagnetic metal is gadolinium (Gd).

Examples of such lipids are Gd-DTPA, Gd.DOTA, GdHPDO3A, Gd-DTPA-bis(stearylamide) (Gd-BSA); Gd-DTPA-bis(myrisitylamide) (GdDTPA-BMA); 1,2-dimyristoyl-sn-glycero-3-phosphoethanolaminediethylene-triamine-pentaacetate:Gd$^{3+}$ (DMPEDTPA:Gd$^{3+}$); D35-1,2-dihexanoyl-sn-glycero-3-phosphocholine; gadolinium (III) 2-{4,7-bis-carboxymethyl-10-[(N,N-distearylamidomethyl-N'-amido-methyl]-1,4,7,10-tetra-azacyclododec-1-yl}-acetic acid (Gd.DOTA.DSA); gadolinium (III) 2-(1-[(N,N-distearyl-amidomethyl)-N'-amidomethyl]-4,7,7-tris-carboxymethyl-1,4,7-triaza-sept-1-yl) acetic acid (Gd.DTPA.DSA); gadolinium (III) 1,4,7,10-tetraazacyclododecane-1,4,7,10-tetraacetic acid mono(N$^1$-distearoylphosphatidylethanolamine)amide (Gd.DOTA.D-SPE); Gd.DOTA.AHX.DSA; Gd.DOTA.AOC.DSA; Gd.DOTA.Ala.Ala.DSA; Gd.DOTA.Gly.Gly.DSA; Gd.DOTA.AN$_2$.DSA; and Gd.DOTA.PEG$_4$.DSA.

Electron Microscopy and Image Processing

An example of a suitable lipid is 1,2-dioleoyl-sn-glycero-3-{[N(5-amino-1-carboxypentyl) iminodiacetic acid]succinyl}-(nickel salt).

Electron Spin Resonance

An example of a suitable lipid is 1,2-diacyl-sn-glycero-3-phosphotempocholine, 1-palmitoyl-2-stearoyl(n-DOXYL)-sn-glycero-3-phosphocholine.

Radioimaging

An example of a suitable lipid is (99m)Tc-DTPA-bis(stearylamide); (99m)Tc-DTPA-bis(myrisitylamide).

PET/SPECT

Suitable PET/SPECT radiometals can be incorporated into lipids for bilayer inclusion, and include $^{89}$Z; $^{111}$I; $_{64}$Cu; $^{68}$Ga; $^{124}$I and $^{86}$Y. For example, these agents can provide signal when chelated to the head group (preferably an optionally substituted poly(aminocarboxylate) group, such as DTPA or DOTA) of the paramagnetic metal lipid used as the MRI label; preferably when the head group is itself conjugated to a hydrophobic hydrocarbon chain and/or to a lipid moiety via a linker. For example, these agents may be chelated to the DOTA headgroup of the DOTA.DSA lipid.

Near Infrared Fluorescence (NIRF) Imaging Label

In another embodiment, the present invention also relates to a NIRF imaging label comprising a near infrared fluorescence imaging agent conjugated to a lipid. This may be as defined above for component (v) of the lipid nanoparticle of the present invention. The invention further relates to a lipid nanoparticle comprising a near infrared fluorescence (NIRF) imaging label of the present invention.

Lipid of Formula (II)

In another embodiment, the present invention also relates to a lipid of formula (II):

wherein R and R' are long hydrocarbyl hydrophobic chains, Y' is a linker element, X is a further linker which extends the distance between PHG and the hydrocarbyl chains R and R' and PHG is a polar head group described as large according to its van der Waals radius.

The polar head group described as large according to its van der Waals radius may for example have a diameter (as described above for the phospholipid) of greater than about 3 Å, preferably greater than about 5 Å, more preferably from about 5 to about 15 Å. Alternatively, the PHG may have a diameter of from about 3 to about 5 Å. The polar head group described as large according to its van der Waals radius may also (or alternatively) be defined in terms of its molecular weight, which is typically greater than 200, preferably greater than 300, more preferably from 400 to 3000.

Examples of suitable polar head groups PHG include protecting groups, such as tert-butoxycarbonyl (Boc); amino acids, such as lysine; oligomers, e.g. of amino acids, for example di-, tri- or tetra-peptides, which may be formed from the same or different amino acids, such as $Gly_2Lys$ or $Glu_2Lys$; and optionally substituted poly(aminocarboxylate) groups. Suitably, PHG may have a terminal carboxylic acid/carboxylate group in the free form, so that it can form e.g. an amide link with Y'RR'.

PHG is preferably an optionally substituted poly(aminocarboxylate) group, preferably an unsubstituted poly(aminocarboxylate) group, such as diethylene triamine pentaacetic acid (DTPA) or 1,4,7,10-tetraazacyclododecane-1,4,7,10-tetraacetic acid (DOTA), which may or may not contain a chelated metal cation.

In a preferred embodiment, the lipid of formula (II) comprises a paramagnetic metal lipid comprising, for example, a paramagnetic metal suitable for MRI, e.g. chelated to the head group PHG of formula (II). Typically, PHG is an optionally substituted poly(aminocarboxylate) group, such as DTPA or DOTA, comprising a paramagnetic metal suitable for MRI. The paramagnetic metal may be, for example, Gd, or radiometals such as $^{64}Cu$. Preferably, the paramagnetic metal is gadolinium (Gd).

The hydrophobic hydrocarbon chains R and R' may independently be, for example, an alkyl group, preferably independently selected from $C_{12}$-$C_{20}$ (preferably saturated) alkyl groups, more preferably $C_{14}$-$C_{20}$ (preferably saturated) alkyl groups. R and R' may be the same or different. In one embodiment, R and R' are the same. Thus in one embodiment, R and R' are the same and are each a $C_{14}$-$C_{20}$ saturated alkyl group, such as a $C_{18}$ saturated alkyl group.

The linker Y' preferably comprises a terminal functional group which may react with a terminal functional group of the linker X. For example, the linker Y' may comprise a terminal carboxylic acid group which reacts with a terminal amine group of X to form an amide link, or alternatively the linker Y' may comprise a terminal amine group which reacts with a terminal carboxylic acid group of X to form an amide link. In one preferred embodiment, Y' comprises an amide functional group, such as an amidomethylamine group (wherein the terminal amine forms an amide link with a terminal carboxylic acid group of X). The group represented by Y'RR' may thus correspond to a lipid moiety which may comprise, for example, one or more alkyl groups, preferably $C_{12}$-$C_{20}$ (preferably saturated) alkyl groups, more preferably $C_{14}$-$C_{20}$ (preferably saturated) alkyl groups as described above. A suitable lipid moiety comprising alkyl groups as the group Y'RR' may comprise a N,N-di($C_{12}$-$C_{20}$ saturated lipid) amidomethylamine, such as N,N-distearylamidomethylamine (DSA).

The further linker X is preferably an organic linker group having a linear chain length of from 3 to 40 atoms (for example including, but not limited to, carbon, oxygen and/or nitrogen atoms). For example, the further linker X may comprise a hydrocarbyl chain, or may comprise carbon atoms and further functional groups such as ether, carboxyl, amine, amide or hydroxyl groups. Preferably X comprises a hydrocarbyl chain of from 3 to 12 carbon atoms, preferably from 3 to 10 carbon atoms, preferably a $C_3$-$C_{12}$ alkyl group (such as a $C_3$-$C_{12}$ saturated alkyl group), more preferably a $C_3$-$C_{10}$ alkyl group (such as a $C_3$-$C_{10}$ saturated alkyl group); a polyethylene glycol (PEG) group, in particular a PEG oligomer having for example from 2 to 10 ethylene oxide repeat units; one or more (e.g. one or two) aminooxy (AN) group; and/or one or more amino acid residues (such as alanine and/or glycine), preferably a dipeptide or tripeptide residue (e.g. comprising alanine and/or glycine).

The linker X may comprise terminal functional groups such as carboxylic acid and/or amine, to facilitate linking to Y' and/or PHG. Thus X may for example comprise a terminal amine which forms an amide link with a terminal carboxylic acid group of PHG, and/or a terminal carboxylic acid group which forms an amide link with a terminal amine group of Y'. When X is an amino acid or peptide residue, the terminal amine and carboxylic acid groups may be used to link to PHG and Y'. Suitable examples of X which comprise a hydrocarbyl group, such as an alkyl group, include amino carboxylic acids, such as a $C_3$-$C_{12}$ amino carboxylic acid, preferably a $C_3$-$C_{10}$ amino carboxylic acid. The amino carboxylic acid maybe a $C_3$-$C_{12}$ or $C_3$-$C_{10}$ saturated carboxylic acid, for example aminohexanoic acid, aminoheptanoic acid or aminooctanoic acid.

In preferred embodiments of the paramagnetic lipid of formula (II), PHG comprises Gd.DOTA or Gd.DOTA and/or Y'RR' comprises a N,N-di($C_{12}$-$C_{20}$ saturated lipid) amidomethylamine, such as N,N-distearylamidomethylamine (DSA). Specific examples are shown below:

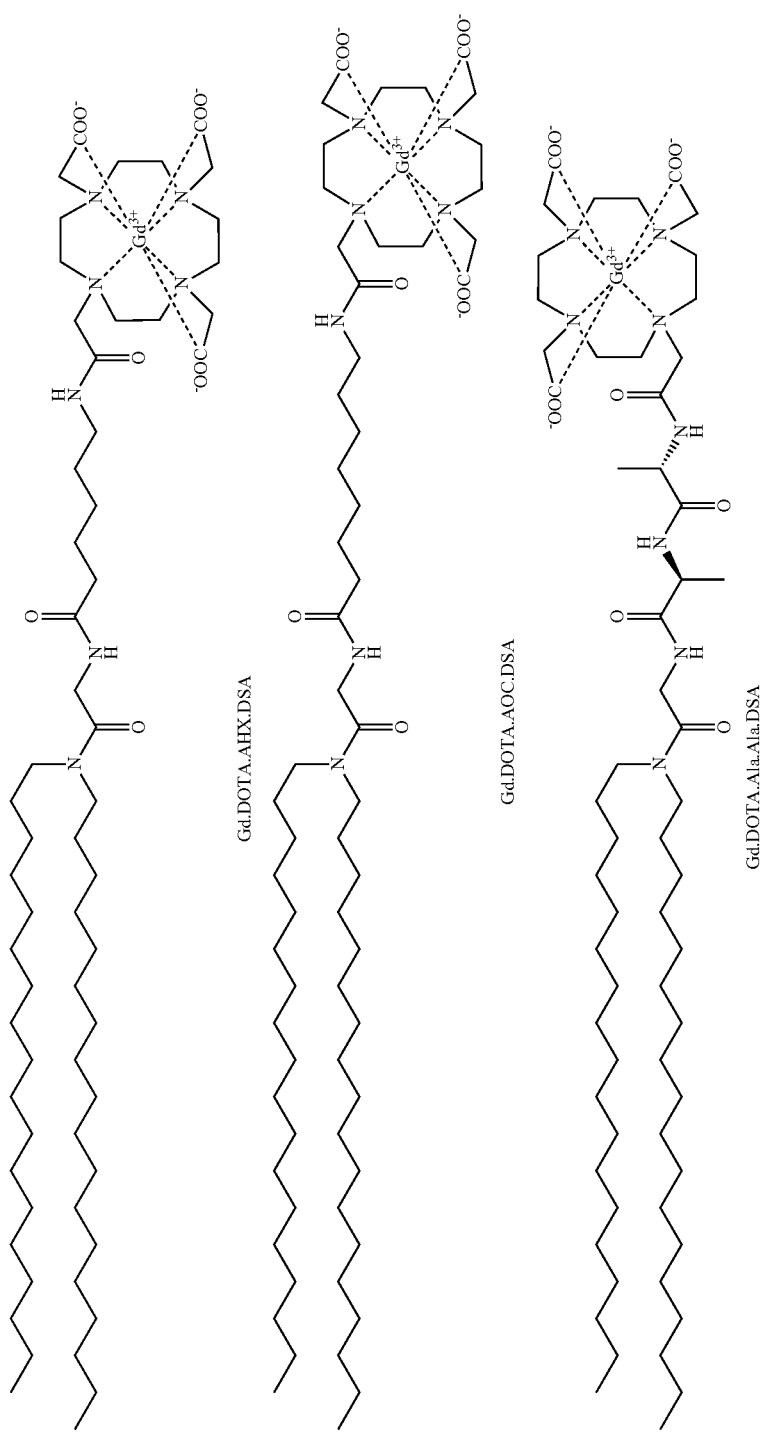

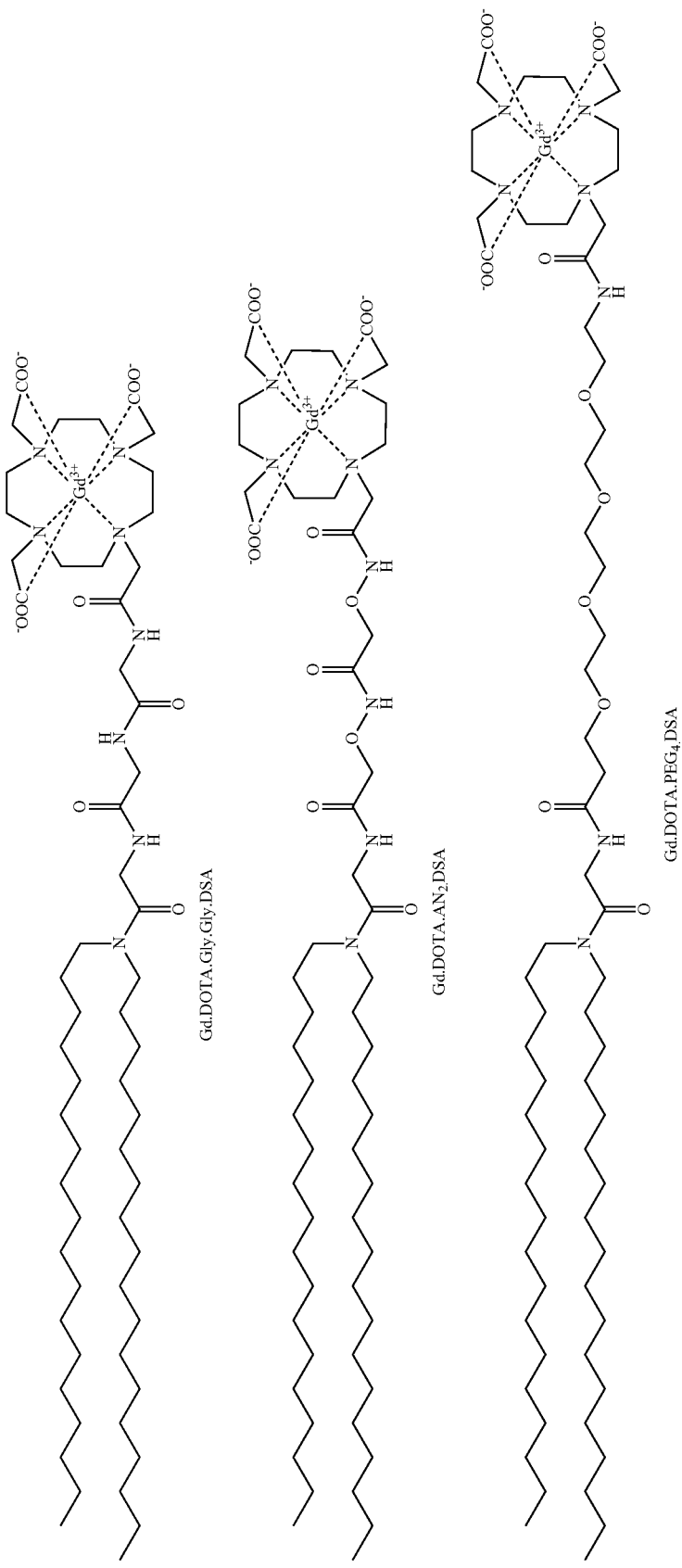

The invention further relates to a lipid nanoparticle comprising a lipid of formula (II).

API

The lipid nanoparticles described herein may be formulated with one or more active pharmaceutical ingredients (APIs) in order to prepare a delivery vehicle that is suitable for the delivery of one or more agents in vivo or in vitro.

The API is associated with the lipid nanoparticle such that the API is made available for therapy on thermal activation of the lipid nanoparticle. For example, the API (typically a small molecule API such as a drug) may be present in the interior of the lipid nanoparticle structure (encapsulated), and released on thermal activation of the lipid nanoparticle. Alternatively, the API (such as a biopharmaceutical agent) may be associated with the lipid nanoparticle (e.g. incorporated with the lipid, such as in the lipid bilayer) and made available (e.g. exposed or released) on thermal activation of the lipid nanoparticle.

The API may be a drug, compound or analogue thereof, particularly a small molecular weight compound, or a biopharmaceutical agent. For example, the agent may be a known drug or compound or an analogue thereof. In one embodiment, the API is a drug or biopharmaceutical agent.

Examples of APIs include, but are not limited to, anti-inflammatory agents; anti-cancer and anti-tumour agents; anti-microbial and anti-viral agents, including antibiotics; anti-parasitic agents; vasodilators; bronchodilators, anti-allergic and anti-asthmatic agents; peptides, proteins, glycoproteins, and lipoproteins; carbohydrates; receptors; growth factors; hormones and steroids; neurotransmitters; analgesics and anaesthetics; narcotics; catalysts and enzymes; vaccines or genetic material. Additional examples of APIs include a nucleic acid or a polynucleotide (which may be single or double-stranded), for example DNA, RNA, mRNA, siRNA or antisense olignucleotides. These may be naturally occurring or synthetic. A further examples of the API includes an antibody, for example, a polyclonal antibody, a monoclonal antibody or a monoclonal humanised antibody.

In a preferred embodiment, the API is an anti-cancer agent, an antibody or an antibiotic.

Suitable drugs include, but are not limited to hydrophilic drugs, hydrophobic drugs, and water-insoluble drugs. A hydrophilic drug or other active agent is readily dissolved in water. A hydrophobic drug or other active agent has a low affinity for water, and does not readily dissolve in aqueous solutions. The dissolution of hydrophobic drugs or other active agents in water, however, is not impossible, and can be achieved under certain conditions that are known to those skilled in the art. Hydrophobic drugs or other active agents typically are dissolved in non-polar (e.g., lipophilic) solvents. Organic solvents can be used to dissolve water-insoluble drugs or other active agents. Hydrophilic active agents may be included in the interior of the lipid nanoparticles such that the vesicle bilayer creates a diffusion barrier preventing it from diffusing throughout the body.

In one embodiment, the drugs or other APIs are preferably anticancer agents—such as chemotherapeutic agents—in that they are capable of inducing (either directly or indirectly) cancer cell or tumour cell cytotoxicity. Examples of such anticancer agents include, but are not limited to, mitoxantrone (as described in WO02/32400), taxanes (as described in WO01/70220 and WO00/01366), paclitaxel, camptothecin, camptothecin derivatives (as described in WO02/058622 and WO04/017940), topotecan, gemcitabine (as described in WO04/017944), vinorelbine (as described in WO03/018018), vinblastine, anthracyclines, adria, adriamycin, adriamycine, capecitabine, docetaxel, doxorubicin, didanosine (ddl), stavudine (d4T), antisense oligonucleotides—such as c-raf antisense oligonucleotide (RafAON) (as described in U.S. Pat. Nos. 6,126,965 and 6,559,129), antibodies—such as herceptin, immunotoxins, hydroxyurea, melphalan, chlormethine, extramustinephosphate, uramustine, ifosfamide, mannomustine, trifosfamide, streptozotocin, mitobronitol, mitoxantrone, methotrexate, 5-fluorouracil, cytarabine, tegafur, idoxide, taxol, daunomycin, daunorubicin, bleomycin, amphotericin (e. g., amphotericin B), carboplatin, cisplatin, BCNU, vincristine, camptothecin, mitomycin, etopside, histermine dihydrochloride, tamoxifen, cytoxan, leucovorin, oxaliplatin, irinotecan (as described in WO03/030864), 5-irinotecan, raltitrexed, epirubicin, anastrozole, proleukin, sulindac, EKI-569, erthroxylaceae, cerubidine, cytokines—such as interleukins (e.g. interleukin-2), ribozymes, interferons, oligonucleotides, and functional derivatives of the foregoing.

Preferably, the anti-cancer agent is selected from topotecan and doxorubicin.

In another embodiment, the drugs or other APIs can be nephrotoxic, such as cyclosporin and amphotericin B, or cardiotoxic, such as amphotericin B and paclitaxel. Additional examples of drugs which may be delivered include but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone,17a-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, heparin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, somatotropins (e.g., bovine somatotropin, porcine somatotropin, etc.), oxytocin, vasopressin, GRF, somatostatin, lypressin, pancreozymin, luteinizing hormone, LHRH, LHRH agonists and antagonists, leuprolide, interferons, interleukins, growth hormones (e.g. human growth hormone and its derivatives such as methione-human growth hormone and des-phenylalanine human growth hormone, bovine growth hormone, porcine growth hormone, insulin-like growth hormone, etc.), fertility inhibitors such as the prostaglandins, fertility promoters, growth factors such as insulin-like growth factor, coagulation factors, pancreas hormone releasing factor, analogues and derivatives of these compounds, and pharmaceutically acceptable salts of these compounds, or their analogues or derivatives.

The term "derivative" or "derivatised" as used herein includes chemical modification of an agent. Illustrative of such chemical modifications would be replacement of hydrogen by a halo group, an alkyl group, an acyl group or an amino group.

Further examples of suitable drugs include disease modifying antirheumatoid agents (DMARDs).

Examples of biopharmaceutical agents include peptides, RNAi effectors and anti-TNF agents.

The amount of API to be incorporated in the lipid nanoparticle will depend on the nature of the API and the application in question. As an example, when the API is a drug, such as topetecan or doxorubicin, it may be present in a concentration of from about 5 mg/mL to about 100 μg/mL, preferably from about 2 mg/mL to about 70 μg/mL. For example, lipid nanoparticles may be formulated with about 1.5-1.0 mg/mL doxorubicin, or 0.7-0.3 mg/mL topetecan. In general, the ratio of lipid:drug is suitably from about 10:1 to about 100:1 w/w.

Preferred Lipid Nanoparticles with API

The present invention may thus relate to a lipid nanoparticle as described herein further comprising an API as described herein (such as a drug or biopharmaceutical agent, in particular topetecan or doxorubicin), wherein the molar ratio of (i) phospholipid:(ii) lysolipid:(iii) phospholipid comprising a hydrophilic polymer:(iv) structural lipid of formula (I) (or formula (II)) is about (i) 30-90:(ii) 2-15:(iii) 4 or 5-10:(iv)10-50, preferably about (i) 40-75:(ii) 3-10:(iii) 6-8:(iv) 20-40. Preferably the lipid nanoparticle comprises about 5 or 6-8 mol % of PEG$^{2000}$-DSPE, and/or comprises a first phosphatidylcholine in an amount of from about 40-70 mol %, preferably 45-55 mol %, and a second phosphatidylcholine in an amount of from about 0-10 mol %, preferably 2-8 mol %. The same preferred ratios apply when the structural lipid of formula (I) (or formula (II)) comprises a magnetic resonance imaging (MRI) label.

In another embodiment, the lipid nanoparticle preferably comprises the structural lipid of formula (I) (or formula (II)) in an amount of about 10-50 mol %, preferably about 20-40 mol %, more preferably about 20-35 mol %, e.g. about 25-35 mol %, preferably wherein the amounts of the other components are as described above. Thus preferably, the lipid nanoparticle of the present invention may comprise an MRI label as described herein in an amount of about 10-50 mol %, preferably about 20-40 mol %, more preferably about 20-35 mol %, e.g. about 25-35 mol %, preferably wherein the amounts of the other components are as described above.

In another embodiment, the lipid nanoparticle comprises a near infrared fluorescence (NIRF) imaging label, and the molar ratio of (i) phospholipid:(ii) lysolipid:(iii) phospholipid comprising a hydrophilic polymer:(iv) structural lipid of formula (I) (or formula (II)):(v) NIRF imaging label is about (i) 30-90:(ii) 2-15:(iii) 4 or 5-10:(iv) 10-50:(v) 0.001-10, preferably about (i) 40-75:(ii) 3-10:(iii) 5 or 6-8:(iv) 20-40:(v) 0.01-1. The present invention further relates to such lipid nanoparticles comprising an NIRF imaging label wherein the structural lipid of formula (I) (or formula (II)) is contained in an amount of about 10-50 mol %, preferably about 20-40 mol %, more preferably about 20-35 mol %, e.g. about 25-35 mol %, preferably wherein the amounts of the other components are as described above.

In one preferred embodiment, the present invention relates to a lipid nanoparticle comprising an MRI label and an NIRF imaging label, wherein the molar ratio of (i) phospholipid:(ii) lysolipid:(iii) phospholipid comprising a hydrophilic polymer:(iv) MRI label:(v) NIRF imaging label is about (i) 30-90:(ii) 2-15:(iii) 4 or 5-10:(iv) 10-50:(v) 0.001-10, preferably about (i) 40-75:(ii) 3-10:(iii) 5 or 6-8:(iv) 20-40:(v) 0.01-1, which further comprises an API as described herein (such as a drug or biopharmaceutical agent, in particular topetecan or doxorubicin). The present invention further relates to such lipid nanoparticles comprising an NIRF imaging label wherein the MRI label is contained in an amount of about 10-50 mol %, preferably about 20-40 mol %, more preferably about 20-35 mol %, e.g. about 25-35 mol %, preferably wherein the amounts of the other components are as described above.

In one preferred embodiment, the present invention relates to a lipid nanoparticle comprising one or more of the following preferred components:
(i) at least one phosphatidylcholine;
(ii) at least one lysolipid;
(iii) at least one PEGylated phospholipid;
(iv) an MRI label comprising a gadolinium lipid, preferably a gadolinium lipid of formula (I) or (II) as described above, more preferably wherein PHG is an (optionally substituted) poly(amino carboxylate) group comprising gadolinium, R and R' are each independently a $C_{12}$-$C_{20}$ (preferably saturated) alkyl group, the linker Y or Y' comprises an amide functional group and the optional linker X comprises a $C_3$-$C_{12}$ (preferably saturated) alkyl group (such as a $C_3$-$C_{12}$ amino carboxylic acid group), a polyethylene glycol group, one or more aminoxy groups and/or one or more amino acid residues; and/or
(v) a near infrared fluorescence (NIRF) imaging label;
preferably wherein the amounts of components (i) to (v) correspond to the molar ratios described above, which further comprises an API as described herein (such as a drug or biopharmaceutical agent, in particular topetecan or doxorubicin).

For example, a preferred lipid nanoparticle according to the present invention may comprise one or more of the following preferred components:
(i) a 1,2-di($C_{12}$-$C_{20}$ saturated lipid)-sn-glycero-3-phosphocholine, wherein the saturated lipid groups can be the same or different from each other;
(ii) a 1-($C_{12}$-$C_{20}$ saturated lipid)-sn-glycero-3-phosphocholine;
(iii) a PEGylated phospholipid, wherein the phospholipid comprises a 1-($C_{12}$-$C_{20}$ saturated lipid)-sn-glycero-3-phosphoethanolamine;
(iv) an MRI label comprising a gadolinium lipid, preferably a gadolinium lipid of formula (I) or (II) as described above, for example selected from gadolinium (III) 6,9-bis(carboxylatomethyl)-3-(2-(octadecylamino)-2-oxoethyl)-11-oxo-3,6,9,12-tetraazatriacontanoate (Gd-DTPA-bis (stearylamide); Gd-BSA, or Gd.DTPA.BSA); gadolinium (III) 6,9-bis(carboxylatomethyl)-11-oxo-3-(2-oxo-2-(tetradecylamino)ethyl)-3,6,9,12-tetraazahexacosanoate (Gd- DTPA-bis(myrisitylamide); GdDTPA-BMA, or Gd.DT-PA.BMA); 1,2-dimyristoyl-sn-glycero-3-phosphoethanolaminediethylene-triamine-pentaacetate: $Gd^{3+}$ (DMPEDTPA:$Gd^{3+}$, or Gd.DTPA.DMP); D35-1,2-dihexanoyl-sn-glycero-3-phosphocholine; gadolinium (III) 2-{4,7-bis-carboxymethyl-10-[(N,N-distearylamidomethyl-N'-amido-methyl]-1,4,7,10-tetra-azacyclododec-1-yl}-acetic acid (Gd.DOTA.DSA, also known as gadolinium (III) 2,2',2"-(10-(2-((2-(dioctadecylamino)-2-oxoethyl)amino)-2-oxoethyl)-1,4,7,10-tetraazacyclododecane-1,4,7-triyl)triacetate); gadolinium (III) 2-(1-[(N,N-distearyl-amidomethyl)-N'-amidomethyl]-4,7,7-tris-carboxymethyl-1,4,7-triaza-sept-1-yl) acetic acid (Gd.DTPA.DSA, also known as gadolinium (III) 3,6,9-tris(carboxylatomethyl)-15-octadecyl-11,14-dioxo-3,6,9,12,15-pentaazatritriacontanoate); gadolinium (III) 1,4,7,10-tetraazacyclododecane-1,4,7,10-tetraacetic acid mono($N^1$-distearoylphosphatidylethanolamine)amide (Gd.DOTA.DSPE, also known as gadolinium (III) 2,2',2"-(10-(2-((2-((((R)-2,3-bis(stearoyloxy)propoxy)(hydroxy)phosphoryl)oxy)ethyl)amino)-2-oxoethyl)-1,4,7,10-tetraazacyclododecane-1,4,7-triyl) triacetate); gadolinium (III) 2,2',2"-(10-(2-((6-((2-(dioctadecylamino)-2-oxoethyl)amino)-6-oxohexyl)amino)-2-oxoethyl)-1,4,7,10-tetraazacyclododecane-1,4,7-triyl) triacetate (Gd.DOTA.AHX.DSA); gadolinium (III) 2,2',2"-(10-(2-((8-((2-(dioctadecylamino)-2-oxoethyl)amino)-8-oxooctyl)amino)-2-oxoethyl)-1,4,7,10-tetraazacyclododecane-1,4,7-triyl)triacetate (Gd.DOTA.AOC.DSA); gadolinium (III) 2,2',2"-(10-((4S,7S)-4,7-dimethyl-12-octadecyl-2,5,8,11-tetraoxo-3,6,9,12-tetraazatriacontyl)-1,4,7,10-tetraazacyclododecane-1,4,7-triyl)triacetate (Gd.DOTA.Ala.Ala.DSA), gadolinium (III) 2,2',2"-(10-(12-octadecyl-2,5,8,11-tetraoxo-3,6,9,12-tetraazatriacontyl)-1,4,7,10-tetraazacyclododecane-1,4,7-triyl) triacetate (Gd.DOTA.Gly.Gly.DSA); gadolinium (III) 2,2',2"-(10-(14-octadecyl-2,6,10,13-tetraoxo-4,8-dioxa-3,7,11,14-tetraazadotriacontyl)-1,4,7,10-tetraazacyclododecane-1,4,7-triyl)triacetate (Gd.DOTA.$AN_2$.DSA); and gadolinium (III) 2,2',2"-(10-(22-octadecyl-2,18,21-trioxo-6,9,12,15-tetraoxa-3,19,22-triazatetracontyl)-1,4,7,10-tetraazacyclododecane-1,4,7-triyl)triacetate (Gd.DOTA.$PEG_4$.DSA); and/or (v) a near infrared fluorescence (NIRF) imaging agent comprising a lipid, such as a fatty acid;

preferably wherein the amounts of components (i) to (v) correspond to the molar ratios described above, and an API as described herein (such as a drug or biopharmaceutical agent, in particular topetecan or doxorubicin).

A further preferred lipid nanoparticle according to the present invention may comprise one or more of the following preferred components:
(i) DPPC and DSPC;
(ii) MSPC;
(iii) $PEG^{2000}$-DSPE;
(iv) Gd.DOTA.DSA, Gd.DTPA.DSA, Gd.DOTA.AHX.DSA and/or Gd.DOTA.AOC.DSA; and/or
(v) a near infrared fluorescence (NIRF) imaging agent comprising a N,N-di($C_{12}$-$C_{20}$ saturated lipid)methylamine;

preferably wherein the amounts of components (i) to (v) correspond to the molar ratios described above; more preferably wherein DPPC is present in an amount of from about 40-70 mol %, preferably 45-55 mol %, and DSPC is present in an amount of from about 0.1-10 mol %, preferably 2-8 mol %, and/or $PEG^{2000}$-DSPE is present in an amount of from about 6-8 mol %, preferably from about 6-6.5 mol %, and/or MSPC is present in an amount of about 5 mol %, and an API as described herein (such as a drug or biopharmaceutical agent, in particular topetecan or doxorubicin).

In one preferred embodiment, the lipid nanoparticle may comprise one or more of the following preferred components:
(i) DPPC and DSPC;
(ii) MSPC;
(iii) $PEG^{2000}$-DSPE;
(iv) Gd.DOTA.DSA, Gd.DOTA.AHX.DSA and/or Gd.DOTA.AOC.DSA; and/or
(v) XL750.DSA;

preferably wherein the amounts of components (i) to (v) correspond to the molar ratios described above; more preferably comprising DPPC:DSPC:MSPC:$PEG^{2000}$-DSPE:Gd.DOTA.DSA:XL750.DSA in a molar ratio of 54:5:5:6:30:0.05, and an API as described herein (such as a drug or biopharmaceutical agent, in particular topetecan or doxorubicin).

Pharmaceutical Compositions

The present invention also relates to a pharmaceutical composition comprising a lipid nanoparticle of the present invention, preferably wherein the lipid nanoparticle comprises at least one API, and a pharmaceutically acceptable carrier.

The formulation of the lipid nanoparticle will depend upon factors such as the nature of the API, whether a pharmaceutical or veterinary use is intended, etc.

The lipid nanoparticles are typically formulated for administration in the present invention with a pharmaceutically acceptable excipient (such as a carrier or diluents). The pharmaceutical carrier or diluent may be, for example, an isotonic solution.

Solutions for intravenous administration or infusion may contain as carrier, for example, sterile water or preferably they may be in the form of sterile, aqueous, isotonic saline solutions.

The dose of the lipid nanoparticles may be determined according to various parameters, especially according to the substance used; the age, weight and condition of the patient to be treated; the route of administration; and the required regimen.

Again, a physician will be able to determine the required route of administration and dosage for any particular patient. A typical dose is from about 0.01 to 1000 ng per kg of body weight, according to the age, weight and conditions of the individual to be treated, the type and severity of the condition and the frequency and route of administration. Dosage levels may be, for example, from 10 to 100 mg/$m^2$ (equivalent to drug dose; example Doxil® dose is 50 mg/$m^2$ equivalent to doxorubicin dose).

The lipid nanoparticles as described herein may be administered alone or in combination. They may also be administered in combination with another pharmacologically active agent, such as another agent for imaging and/or another drug, for example an anti-cancer drug. The combination of agents may be may be formulated for simultaneous, separate or sequential use.

In another embodiment, the present invention relates to a pharmaceutical composition comprising a lipid of formula (II) (e.g. as a lipid nanoparticle comprising a lipid of formula (II)) and a pharmaceutically acceptable carrier. The formulation of the pharmaceutical composition may be as described above for the lipid nanoparticle of the present invention.

Medical Use

Lipid Nanoparticles

The lipid nanoparticles of the present invention as described above (or a pharmaceutical composition as described above) may be for use in a method of therapy or diagnosis of the human or animal body. Lipid nanoparticles which comprise an MRI label and/or an NIRF imaging label as described above may be particularly suitable for use in the methods described herein.

In one embodiment, the lipid nanoparticles or pharmaceutical composition are for use in a method of treatment or diagnosis comprising hyperthermia and/or the application of ultrasound. In particular, the present invention relates to a lipid nanoparticle or pharmaceutical composition for such a use, wherein the method comprises:

administering to a subject (in need thereof) a (therapeutically effective amount of a) lipid nanoparticle as described above or pharmaceutical composition comprising a lipid nanoparticle as described above and a pharmaceutically acceptable carrier;

monitoring the progress of, or detecting, the lipid nanoparticle or pharmaceutical composition to or in an area of interest using MRI and/or optical imaging methods; and heating or applying ultrasound to the area of interest.

The invention also relates to a method of treatment comprising:

administering to a subject in need thereof a therapeutically effective amount of a lipid nanoparticle as described above or pharmaceutical composition comprising a lipid nanoparticle according as described above and a pharmaceutically acceptable carrier;

monitoring the progress of the lipid nanoparticle or pharmaceutical composition to an area of interest using MRI and/or optical imaging methods; and heating the area of interest, preferably by applying continuous and/or high frequency focused ultrasound.

The heating (i.e. the hyperthermia) may be generated using a method selected from laser heating, radiofrequency thermal ablation (RFA), microwave hyperthermia and/or focused ultrasound (FUS). In a preferred embodiment, the hyperthermia is generated using focused ultrasound (FUS), in particular continuous and/or high frequency focused ultrasound (FUS).

In one preferred embodiment, the lipid nanoparticles or pharmaceutical composition may be for use in the treatment of cancer or rheumatoid arthritis. Thus the present invention relates to use of lipid nanoparticles or pharmaceutical composition as described herein in the manufacture of a medicament for use in the treatment of cancer or rheumatoid arthritis, and to a method of treatment of cancer or rheumatoid arthritis, comprising administering to a subject in need thereof a therapeutically effective amount of a lipid nanoparticle or pharmaceutical composition as described above.

In particular, the present invention relates to a lipid nanoparticle or pharmaceutical composition for use in the treatment of cancer by a method comprising applying hyperthermia or continuous and/or high frequency focused ultrasound (FUS). Thus, the invention also relates to use of a lipid nanoparticle or pharmaceutical composition as described above for the manufacture of a medicament for use in the treatment of cancer by a method comprising applying hyperthermia or continuous and/or high frequency focused ultrasound (FUS). The invention may also relate to a method of treatment of cancer, comprising administering to a subject in need thereof a therapeutically effective amount of a lipid nanoparticle or pharmaceutical composition as described above, and applying hyperthermia or continuous and/or high frequency focused ultrasound (FUS).

In another embodiment, the present invention relates to a NIRF imaging label as described above (or a lipid nanoparticle and/or pharmaceutical composition comprising said label) for use in a method of therapy or diagnosis of the human or animal body as described above, such as in the treatment of cancer, in particular for use in a method of treatment comprising hyperthermia and/or the application of ultrasound as described above.

Lipid of Formula (II)

The lipid of formula (II) of the present invention as described above (or a lipid nanoparticle or pharmaceutical composition comprising said lipid) may be for use in a method of therapy or diagnosis of the human or animal body. Lipids which comprise a paramagnetic metal suitable for MRI as described above may be particularly suitable for use in the methods described herein.

In one embodiment, the lipid, lipid nanoparticles or pharmaceutical composition are for use in a method of treatment or diagnosis comprising hyperthermia and/or the application of ultrasound. In particular, the present invention relates to a lipid, lipid nanoparticle or pharmaceutical composition for such a use, wherein the method comprises:

administering to a subject (in need thereof) a (therapeutically effective amount of a) lipid, lipid nanoparticle or pharmaceutical composition as described above;

monitoring the progress of, or detecting, the lipid, lipid nanoparticle or pharmaceutical composition to or in an area of interest using MRI and/or optical imaging methods; and heating or applying ultrasound to the area of interest.

The invention also relates to a method of treatment comprising:

administering to a subject in need thereof a therapeutically effective amount of a lipid, lipid nanoparticle or pharmaceutical composition as described above;

monitoring the progress of the lipid, lipid nanoparticle or pharmaceutical composition to an area of interest using MRI and/or optical imaging methods; and heating the area of interest, preferably by applying continuous and/or high frequency focused ultrasound.

The heating (i.e. the hyperthermia) may be generated using a method selected from laser heating, radiofrequency thermal ablation (RFA), microwave hyperthermia and/or focused ultrasound (FUS). In a preferred embodiment, the hyperthermia is generated using focused ultrasound (FUS), in particular continuous and/or high frequency focused ultrasound (FUS).

In one preferred embodiment, the lipid, lipid nanoparticles or pharmaceutical composition may be for use in the treatment of cancer or rheumatoid arthritis. Thus the present invention relates to use of a lipid, lipid nanoparticles or pharmaceutical composition as described herein in the manufacture of a medicament for use in the treatment of cancer or rheumatoid arthritis, and to a method of treatment of cancer or rheumatoid arthritis, comprising administering to a subject in need thereof a therapeutically effective amount of a lipid, lipid nanoparticle or pharmaceutical composition as described above.

In particular, the present invention relates to a lipid, lipid nanoparticle or pharmaceutical composition for use in the treatment of cancer by a method comprising applying hyperthermia or continuous and/or high frequency focused ultrasound (FUS). Thus, the invention also relates to use of a lipid, lipid nanoparticle or pharmaceutical composition as described above for the manufacture of a medicament for use in the treatment of cancer by a method comprising applying hyperthermia or continuous and/or high frequency focused ultrasound (FUS). The invention may also relate to a method of treatment of cancer, comprising administering to a subject in need thereof a therapeutically effective amount of a lipid, lipid nanoparticle or pharmaceutical composition as described above, and applying hyperthermia or continuous and/or high frequency focused ultrasound (FUS).

Hyperthermia or Ultrasound Methodology

The method of inducing hyperthermia may be by using ultrasound (US), such as focused ultrasound (FUS), usually at high intensity (HIFU), on a subject, normally a living human (being) or animal preferably using imaging as guidance. The FUS is delivered in bursts of continuous ultrasound. By continuous it is usually meant that the ultrasound machine is switched on in its normal operating mode. In practice ultrasound machines may (also) deliver ultrasound in a pulsed mode.

Other methods include those where the US is pulsed (100 ms on, 900 ms off) at a pulse rate of 1 Hz[10, 36, 37]. This was for about 2 minutes, so 120 pulses were delivered. It was focused above a tumour and rastered. The temperature of the tissue was heated to 42° C.

Herein continuous usually means that a pulsed mode such as described above is used, or that the ultrasound is generated in an almost or truly continuous (non-pulsed) mode.

The method of inducing hyperthermia and/or applying ultrasound in the invention can be in a continuous or constant (or high frequency or non-pulsed) manner. The US may be applied in one or more burst(s), cycle(s)- or (short) period(s) of time, e.g. according to the information provided from the clinical imaging method and/or the distribution of the therapeutic. Each burst may be composed of (truly) continuous US or a sequence of pulses of US. The application of the ultrasound can therefore be cycled, or periodic. There may be cycles or periods of applying continuous, high frequency or high intensity) ultrasound, interspersed with (or before and/or after) reducing, or stopping, or reducing the intensity of, the application of ultrasound. This can be achieved by applying the ultrasound in one or more (e.g. short) (successive and/or consecutive) bursts or cycles.

The FUS or heating of the tissue may result in hyperthermia and therefore in higher blood supply and/or increased concentration of the drug in the treated area. It can also increase the (temperature controlled or triggered) release of a drug (or API) in, at or near the heated/FUS tissue. Accompanying imaging can allow the active or real time monitoring of the API in the body of a living (e.g. human) body. The FUS is thus applied suitably while the API is present in blood circulation or in the body (and at the site of interest).

Other suitable methods of inducing hyperthermia (other than US) include radiofrequency (RF) ablation and/or microwave (MW) hyperthermia.

The method of applying ultrasound and/or inducing hyperthermia may thus comprise:
  a. applying high intensity and/or pulse modulated US, e.g. in a pulsed or continuous mode, or inducing hyperthermia in, a (desired) part of a body of interest (such as a tissue or organ) of a (usually living) subject such as a human, mammal or animal;
  b. reducing (the power or intensity of) or stopping (such as halting or interrupting) the application of the ultrasound (such as FUS), or the induction of hyperthermia, such as to the subject (such as to allow cooling and as hypothesised in literature controlling the blood flow); and
  c. restarting or repeating the application of (usually continuous, such as pulsed) ultrasound, or the induction of hyperthermia, again preferably to the subject, and preferably to the same part of the body. The frequency and the timings of these repeats can be indicated by clinical imaging such as MRI, NIRF (Near infrared fluorescence) and/or PET/SPECT.

The FUS can induce hyperthermia (i.e. heat the body part).

This method may be conducted or repeated in order to heat or warm a tissue or body part to a desired temperature or temperature range (e.g. 39 to 42° C.). The various parameters of the US can be adjusted (such as constantly or regularly) in order to achieve this, for example when provided with feedback from the imaging.

Prior art US protocols can comprise a pulsed method of applying FUS (90 ms on, 910 ms off, 1 Hz) at high power levels. However, in the invention, preferably one uses continuous (high intensity or high frequency) US. Thus the US is applied for at least one second, preferably at least 10, 20 or 30 seconds. Usually it will be applied (e.g. continuously or at high intensity or frequency) for at least 1 or 2 minutes. Optimally FUS is applied for at least 3, 4 or 5 minutes. The time gap, or interval, between two consecutive applications or bursts of US is at least one second, preferably at least 10, 20 or 30 seconds. Usually the time interval between (e.g. bursts of US is at least 1, 2, 3 5 or 10 minutes. This can be up to 60 minutes or possibly over, depending on the pharmacokinetics (of the hyperthermia in a focused (e.g. short, but continuous), manner/API) and/or in the individual concerned.

The method can thus result in the warming, or heating (increase in temperature or hyperthermia) of a body part or (desired) tissue (of interest), followed by an interval in the US such as to allow cooling of the body part or tissue (either passively or actively). This may be followed by a further (e.g. second) application of FUS or warming or heating of the body part or tissue. This can be cycled, so that there may be alternating heating and/or cooling stages or cycles, e.g. using imaging as guidance. The heating and/or cooling can be repeated at least twice.

The cooling can be passive, in other words either reducing (the intensity or power of) or stopping the application of ultrasound (or any other focused heating source), so that the body part (or tissue) cools, for example naturally, or active steps could be taken to cool the body part (such as the application of a cooling, or reduced temperature, substance, for example ice). Cooling can thus be achieved simply by reducing or stopping the application of the ultrasound, for example providing an interval between two (consecutive) applications or sessions of ultrasound.

In this way one can provide cycles of heating (hyperthermia) and cooling usually by application of the ultrasound. This can result in an increase in temperature, followed by a decrease in temperature (cooling). It can then be followed by a further (e.g. second) increase in temperature or application of FUS. The invention therefore provides a fluctuating, periodic or cycling ultrasound and/or hyperthermia protocol, such as in a desired part of the subject.

The method can provide ultrasound or hyperthermia which can enhance the effect, efficacy local biodistribution and/or bioavailibility (such as accumulation or location at a site of interest) of a drug (or active ingredient, e.g. a pharmaceutical, or API, as defined later, or a protein or macromolecule such as an (e.g. labelled) antibody), usually in a subject, the method comprising focussing or applying the ultrasound/heat at a desired site in at least two cycles, bursts or periods. This is effectively two (or more) durations, or phases, of (e.g. continuous) ultrasound, each suitably separated or spaced by an interval.

The method can thus comprise:
a. focussing or applying (usually continuous) ultrasound to, or inducing hyperthermia in, a desired site in a subject, for example in order to enhance (e.g. locally) the concentration and/or the effect of a drug (or API) that will be, or may already be, present at, near or in that site, such that the tissue or desired body part is heated or subjected to hyperthermia;
b. stopping, or reducing (the intensity or power) of, the ultrasound/heating and/or allowing the (tissue at the) site to cool, e.g. using imaging as guidance; and
c. repeating a, and optionally b, at least once.

The invention also provides the use of a drug (or API) and/or drug combination and/or their drug delivery system in an ultrasound and/or hyperthermia method of the invention.

The invention may thus relate to a method of imaging, or drug (or API) delivery to a (e.g. human) body, the method comprising:
(a) administering the drug (e.g. alone or present in a (lipid) nanoparticle) to the body or a site of interest;
(b) imaging and/or detecting the drug (or nanoparticles), suitably at or near the site:
(c) applying, or inducing, hyperthermia at or near the site;
(d) not applying (stopping or halting) or not inducing hyperthermia (for a period of time, e.g. an interval);
(e) repeating (c) and (d) at least once;
suitably wherein the hyperthermia (or a parameter thereof) is guided or determined by the imaging (or information derived therefrom).

The total time for the method may be about the half life for the drug or nanoparticles in the body, for example when administered by intravenous injection, and may depend on the distribution of the drug when administered by other routes.

Ultrasound or Hyperthermia Protocol

The application of ultrasound (or heating, i.e. hyperthermia) can result in the drug delivery system (e.g. nanoparticle) or the biopharmaceutical or the drug or API being taken up into the tumour. It can also result in the drug or API being released, such as from the delivery system or (lipid and/or nano-) particle, suitably in, at or near the tissue or the desired site (e.g. that is to be imaged).

The separate bursts or phases of hyperthermia (ultrasound) may be applied for a (short) period of time, suitably to a desired site in the body, preferably to cause a temperature increase. The (application of the) ultrasound may cause (preferably controlled or sustained) release of the API, preferably from the drug delivery system (e.g. liposome or particles), in the body e.g. at or near a target site.

In a preferred embodiment the ultrasound or hyperthermia is stopped, reduced or halted, such as between applications or bursts of (continuous) US. However, alternatively, the ultrasound can be fluctuated, between a low and high setting, for example for periods of higher or lower intensity and/or power. One may therefore vary the intensity, power or time of the ultrasound (heat), and can apply this e.g. according to information (received about the location of the API) using imaging The ultrasound or hyperthermia method may involve the repetition (or cycles of application of) (e.g. continuous) bursts of US or heating, in a repetitive manner.

Preferably, the temperature of the tissue or desired body part is raised or increased to 39° C. to 42° C., such as to from 40° C. to 41° C. Suitably, the temperature of the desired site does not exceed 42° C. or 43° C.

Preferably the hyperthermia (such as ultrasound) application is started after (or even before) the drug has been administered to the subject, for example (up to) 10, 20, 30 or 40 minutes after (or before) administration, preferably 1 hour or 1 hour 30 minutes. Optimally the application of hyperthermia (e.g. US) starts when the drug or API is present at or near the tissue or site of interest, for example an image has been generated or imaging performed, e.g. the image signal is detected at the tumour site.

There may then follow an interval, or a period of no, reduced or halted application of US or hyperthermia (e.g. ultrasound). That time interval will depend on the local pharmacokinetics and biodistribution of the drug and/or its delivery system administered, the subject, the ultrasound or the source of provided focal hyperthermia and a variety of factors. However, it is preferably at least 1 or 10 seconds, or 1, 2, 3 or 5 minutes. Optimally it is at least 10 minutes up to 60, 90 or 120 minute(s). This interval is chosen to allow the tissue to cool down, or be actively cooled and can be adaptable to the drug's local kinetics observed via the imaging method.

After the interval there can be another (e.g. second) application or burst of ultrasound. This can be repeated up to three or multiple times, e.g. depending on the pharmacokinetics of the drug delivery system or API in the circulation.

Each cycle or application of FUS/heating may comprise a first stage, whereby the temperature (of the body part) is increased. This can be followed by a plateau or maintenance (e.g. second) stage where the temperature can remains substantially constant. There may then be a passive or active cooling stage.

After an interval of time, there may then be a second heating stage or application of FUS, whereby the temperature (of the body part) is increased.

Figure 14:
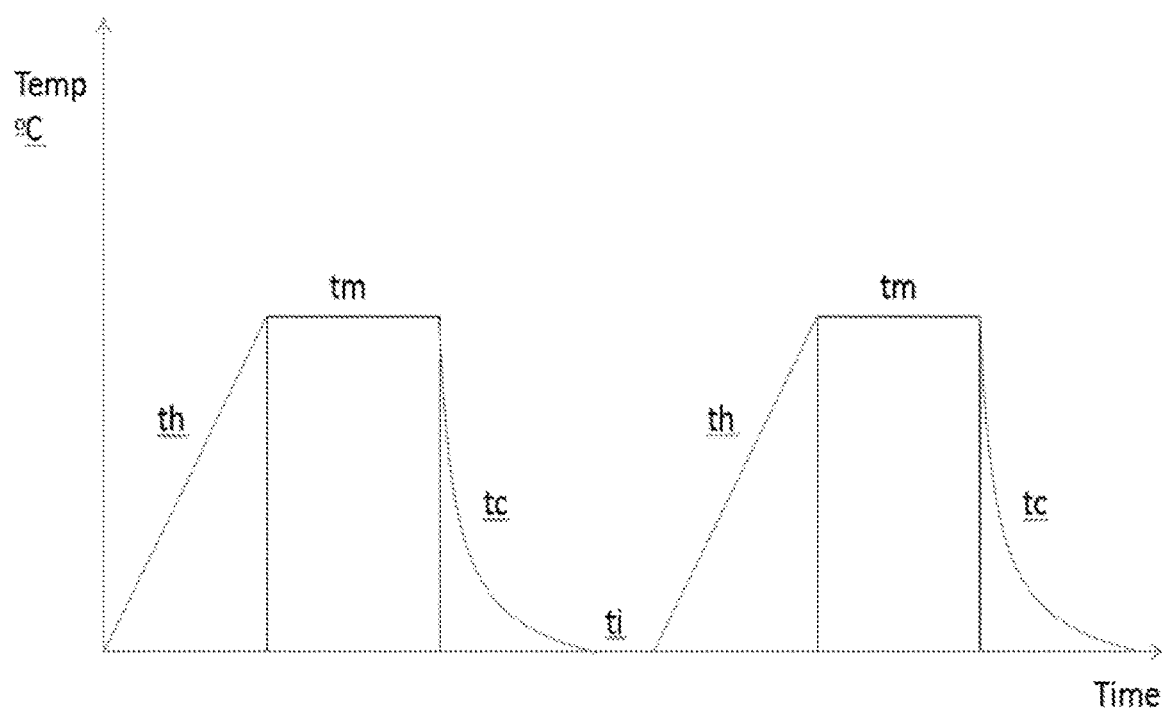
FIG. 14: Characteristics of timings of hyperthermia treatments

The preferred (cycled) application of ultrasound/heating is illustrated in FIG. 14. This shows the stages of the application of ultrasound. In this graph, the time (t) has a number of values, for the component stages, namely:
$t_h$=heating time, such as with application of ultrasound, resulting in an increase in temperature of the desired body site or part, or hyperthermia, e.g. at any point in the desired site of the body;
$t_m$=preferably a plateau, representing the time at which ultrasound/heat is applied or maintained (maintenance time) or where the temperature remains largely stable or constant and/or controlled;
$t_a$=is, preferably, the combination of $t_h + t_m$, namely the total time for, or during which, ultrasound/heat is applied;
$t_c$=is the time at which cooling takes place, preferably but not necessarily to usual body temperature, optionally also with ultrasound application;
$t_i$=is the interval time, or the time between cycles or bursts of ultrasound application or heating, which may be the time at which no ultrasound/heating is applied (or ultrasound is applied but at a lower intensity). $t_i = t_a + t_c$ Preferably, $t_h$ (and/or $t_a$) is from about 10, 20 or 30 seconds to 60, 90 or 120 seconds, preferably about a minute;
$t_m$ (and/or $t_a$) is preferably from about 2 or 3 and/or up to about 4, 5, 6 or 10 minutes, e.g. at any point in the desired site of the body; and/or
$t_i$ can range from about 1, 2, 3 or 5 minutes to about 30, 60, or 120 minutes.

Focussing

Preferably the (energy source providing) hyperthermia (ultrasound) is focused, in the sense that the hyperthermia or ultrasound is placed, focused or directed at or to a single position, or focused on a single position or site. The hyperthermia or ultrasound may be applied to, or focused on, only a single position. It may thus be focused on, or directed at or to, one site for most or all of the time, in particular for each application of hyperthermia or ultrasound. This is in contrast, for example, to rastered or electrically steered beams, where the ultrasound is applied to multiple different sites. For larger sites the ultrasound may be rastered, where the ultrasound focus is moved in a logical and systematic sequence from one part of the tissue to an adjacent or neighbouring part of the tissue, perhaps in line or to cover an area or volume.

Continuous (or High Frequency or Intensity) US

The ultrasound used is preferably applied in burst(s). Earlier techniques have tended to use a pulsed delivery, in particular in 10 Hz cycles (e.g. where 10 ms ultrasound is applied, i.e. "on", and then 90 ms off). In contrast, in the invention, suitably the ultrasound is usually applied continuously (non-pulsed, the terms are used interchangeably), so it is "on" or applied for at least 1 second, and usually for at least 10, 20 or 30 seconds, preferably at least a minute. The ultrasound is therefore provided in short bursts, sessions or in periods. The duration of the burst when the ultrasound is "on" is therefore at least one second. Preferably ultrasound is applied for up to (is 'on' for) 5, 6, 7 or 8 minutes, such as up to 10 minutes. Prolonged or longer application may cause too great a temperature increase above 42° C.

There are usually at least two phases, cycles or periods of ultrasound, so at least two bursts, interspersed by one (or more) intervals. Each period of application of ultrasound, or burst, is normally continuous and is often much longer than (10 ms) advocated in the prior art.

Frequency

Preferably the frequency is at least 10 Hz, 100 Hz or 1,000 Hz, preferably at least 10 kHz. The frequency may thus be at least 10 kHz, 100 kHz or even 1,000 kHz. The maximum frequency may be up to 1,000 kHz (1 MHz), 10 MHz or 100 MHz. Preferably the frequency is from 400, 600 or 800 kHz and/or up to 1.2, 1.4, 1.6, 1.8 or 2 MHz (e.g. about 1 to 1.4 MHz).

Duty Cycle

Preferably the cycle duty is at least 10%, 20%, 30%, 40% or 50%. The duty cycle may be at least 70%, 80% or even 90%. Optimally the cycle duty is at least 95%, 98% or even 99%. The duty may be even as high as (about) 99.9% or higher.

Suitably the FUS source is located, or placed, at a distance from the body part or site of interest by from 5 to 20 cm.

Equipment

The FUS may be suitably delivered using a Philips US machine or an Insightec US machine. Preferably the US is applied not with an imaging machine but one intended for (e.g. thermal) ablation. Other suitable machines are made by Insightec or Sonalleve, or e.g. HAIFU, Theraclion, Sonacare and others.

Power/Energy Levels

One can use higher power levels but for shorter periods of time. However, suitably the power levels are at least 5, 10 or 12 Watts and/or up to 15, 20, 30 or 40 Watts. In particular the acoustic power may be in the range 100-1000 W/cm$^2$.

Preferably the intensity at the focus is less than 1000, 800, 600 or 400 W/cm2, e.g. to control the temperature at the desired value at any point selected at the site of the body.

Drug or API

Suitably the hyperthermia or ultrasound is applied after the drug (or API, which may be a macromolecule such as a protein, for example a (labelled) antibody) and/or their drug delivery system has been administered (to the subject). Preferably the timing is such that the drug has reached, or is present in, near or at the site of interest, or the part of the body to be imaged or subjected to hyperthermia.

Hyperthermia or ultrasound can be applied prior to administration of the drug or API, in order to make the tissue more "leaky". However, preferably the hyperthermia is intended to warm the tissue where the drug or API is already near or present and/or e.g. increase (in this way) the blood supply and/or the distribution or accumulation of the drug at the site of interest. In other words one can apply US, or induce hyperthermia, at a body site which contains or has an effective amount of the drug. In particular the drug may comprise liposomes, e.g. lipid and/or nano-particles, in particular thermosensitive ones, and when US is applied these may already be in the body, suitably at, near or in the site of interest. The particles or liposomes are thus preferably at, or near, a site or part of the body that is to be imaged and/or where an API is present, or due to be released, suitably as a result of the hyperthermia or FUS. The application of ultrasound, or the increase in temperature, therefore preferably releases a drug or API from the (lipid or nano-) particles or may enhance its diffusion or accumulation within the site of the body targeted. The hyperthermia protocol can therefore heat the tissue or site of interest, and so can heat the thermosensitive e.g. liposome) particles drug delivery systems, to cause the release of the drug and/or API at or near that site.

Gradual Heating

The hyperthermia or ultrasound is usually applied so that there can be a controlled and/or gradual increase in temperature of the site (or body part) of interest. This is preferable to a particularly high or sharp increase in temperature. Preferably the (gradual temperature increase or phase of the) ultrasound is from 10 to 120 seconds (in some embodiments such as from 30 to 90 seconds, optimally from 40 to 80 seconds), e.g. at each point in the site of the body.

There then may follow a plateau and/or maintenance of the temperature, whereby the hyperthermia or ultrasound results in the temperature of the part of the body of interest being maintained at a relatively steady state, such as substantially at the same temperature, e.g. at about 41° C., preferably 40-41° C.

Unlike the prior art, the present invention is to be used on live humans and/or animals. The human or animal will be awake or conscious, rather than being anaesthetised.

The ultrasound (probe) will usually be directly applied on the body, for example on the skin (although gel may need to be applied first to the skin). The ultrasound is therefore direct application, focused in the body site of interest rather than using a water bath that may induce general hyperthermia. The subject will usually be a live (and conscious or awake) human. The hyperthermia (ultrasound) will usually be focused, so as to position the focal point of the US at or near the site of interest in the body. In contrast, prior art techniques have an animal placed in a water bath.

Imaging

The invention can implement image assisted or image guided hyperthermia. This may be a process for inducing hyperthermia (or heating a tissue or part of the body of interest, in a subject) while (e.g. simultaneously) imaging the subject. Imaging may be based on ultrasound and/or magnetic resonance (e.g. MRI) or on ionising radiation (CT or PET/SPECT) or combination MRI/PET and/or fluorescence (e.g. NIRF). Imaging can also be done using novel techniques (e.g. RAMAN and or Microwave). Imaging therefore may be in real time.

One may therefore image the tissue and/or part of the body of interest while the hyperthermia or ultrasound is being applied (to that body part), or during an interval between period(s) of application of hyperthermia or ultrasound. Real time imaging can therefore assist, influence or guide the hyperthermia (such as the hyperthermia protocol). The imaging can therefore assist in the hyperthermia applied, and in particular one or more parameters of the ultrasound, for example the location or focus of the ultrasound, the power (energy) or intensity settings, length of time of the application of the burst of ultrasound, in particular they may influence $t_h$, $t_m$, $t_c$ and/or $t_i$. The temperature of the heated tissue can be assessed using imaging techniques. MRI thermometry provides a feedback to the hyperthermia system allowing absolute control of the temperature at the site or tissue of interest. Near IR cameras can also provide information regarding the affected tissue temperature.

The method may thus involve simultaneous hyperthermia and (e.g. NIRF and/or MRI) imaging.

The API and/or the delivery system (particles) thus preferably comprise a label, or an imaging and/or contrast agent. This may allow them to be detected and hence imaged. The tissue or part of the body and/or the subject can therefore be subject to imaging, and an image of the body part of interest obtained. That may then dictate one or more of the parameters of the application of ultrasound. This technique therefore allows a person to decide on the application or variables of the ultrasound as a result of the imaging, assisted by the label(s) present in the nanoparticles.

Discussion

FUS is a non-invasive method that can be used to induce deep and localised hyperthermia in a controlled manner (12). Lipid nanoparticles (LNPs) of the present invention designed for heat triggered local controlled drug release in target tumours, that are also equipped with imaging probes for the real time/diagnostic imaging of drug delivery from point of administration to target, are described as a type of theranostic nanoparticle (TNP) (16). The potential benefits of such systems are several. Nanoparticle biodistribution and drug pharmacokinetic behaviour can be visualized in real time, so too can local drug delivery (16). Such characteristics might be considered sufficient to suggest that once such TNP systems can be optimized for drug delivery, then these could be ideal platform technologies for the personalized therapy of cancers. For this reason, the present inventors investigated the design and creation of a novel TNP formulation by combining features of thermosensitive liposome (TSL) systems with features of two novel imaging lipid-based nanoparticle systems (imaging LNPs). These two imaging LNPs (folate-receptor targeted and non-targeted; both prepared with Gd.DOTA.DSA) were prepared with the dual intention of demonstrating proof of concept for the imaging of tumour cells in vivo by MRI plus fluorescence imaging. More recent studies with near infra red fluoresent (NIRF) labelled TSLs loaded with topotecan further demonstrated proof of concept for imaging the accumulation of LNP systems into tumours in vivo using NIRF probes. These studies together also confirmed appropriate nanoparticle properties for accumulation into tumours post i.v.-administration (17-23). Both imaging LNPs and the NIRF-labelled TSL system were observed to undergo exceptional accumulation into tumour volumes (as visualized by MRI and fluorescence optical imaging). Specifically, non receptor targeted imaging LNPs accumulated in tumour by the enhanced permeability and retention (EPR) mechanism ("passive" targeting) and labeled cells for MRI over a period of 24 h. These imaging LNPs were seen to access the entire hyperpermeable, living volume of the tumour while being excluded from the necrotic regions. By contrast, the folate receptor (FR)-targeted imaging LNPs accumulated in the tumour and labeled cells for MRI from 2 h onwards. Post EPR-mediated uptake, these imaging LNPs appeared to undergo substantial FR-mediated cell entry leading to local accumulation in more perivascular and macrophage-rich locations. The NIRF-labelled TSL system was also observed to enter tumour volumes by EPR effect mechanisms over a period of approx 2 h post administration, and thereafter NIRF signals persisted in tumours for at least 20 days.

In seeking to combine features of known TSL systems with those of the novel imaging LNPs described above, a key decision was to introduce near infrared fluorescence (NIRF) optical imaging because of the excellent tissue penetration of NIR (700-900 nm) radiation. Accordingly, we now describe the formulation and applications of MRI and optical image guided theranostic nanoparticles for cancer treatment. These IgFUS-TNPs are shown to have an unparalleled synergy with short moderate intensity FUS induced bursts of hyperthermia (3-5 mins) that were employed in place of HIFU treatment (>30 min). This synergy appears to enable a substantial approx $10^2$-fold increase in drug concentration in hyperthermia treated tumours compared with controls. The implications of these data for clinical chemotherapy are also discussed.

The development of image guided advanced therapeutics using LNP systems is a potentially powerful technology for the personalized medicine of tomorrow. Currently there is a growing interest in the use of clinically applicable imaging tools to study nanoparticle biodistribution with time, and non-invasive physical triggers that promote controlled, zonal drug release (22,24).

IgFUS-TNPs were found to demonstrate physical properties that appear to synergize with short moderate intensity FUS induced hyperthermia treatments, leading to substantial partition of nanoparticles from blood pool to FUS treated tumours in combination with hyperthermia-mediated controlled release of drug into the treated tumour volumes. Should such data be reproduced in a clinical trial then this combination could have a transformational impact upon chemotherapy and the standard of care for cancer disease management. Both NIRF and MRI are clinically appropriate imaging techniques.

For more than five decades, hyperthermia has already shown synergistic effects with neo-adjuvant chemotherapy and radiotherapy in clinic, improving existing treatments. Various methods have been used to induce hyperthermia such as lasers, hot water baths, microwave and radiofrequency applicators (3). As a clear demonstration of the importance of mild hyperthermia, Li et al. (25) have shown significant effects from water bath hearing on anti-tumour effects of their formulations. Since every tumour is believed to have a significantly different interstitial fluid flow and/or matrix density, a big challenge remains in the vascular permeation of the tumour in order to improve the drug delivery. Local hyperthermia appears to increase pore sizes in tumour vasculature, decrease steric and hydrodynamic hindrances, thereby elevating intratumoral interstitial fluid flow and pressure in a manner that might facilitate nanoparticle (~125 nm in diameter) extravasation. Hyperthermia may also increase local blood perfusion in order to modify the pharmacokinetics of an API in the heated volume (26). Indeed such potential hyperthermia effects in tumours were reported by Kong et al. (27). Indeed mild hyperthermia (41° C. for 1 h) has been reported to generate gaps in the endothelial lining of up to 10 μm (25), for at least 8 h. These data supported similar observations by Kong et al. in a previous study (28). In our studies here, we would suggest that the observed synergism between short moderate intensity FUS pulse applications and IgFUS-TNP mediated controlled drug released in tumours may well be down to some of the hyperthermia-induced physical changes in tissue described above. However, we cannot rule out that other more selective mechanisms are also involved given the magnitudes of the effects and synergies that we have observed and describe above. Our first, short moderate intensity FUS pulse was timed to take place post IgFUS-TNP administration when nanoparticle recruitment to the FUS treated tumour is already partially underway but approximately half of the nanoparticle remains in the blood pool. FUS induced EPR effects and concurrent FUS triggered drug release do not appear to be saturated events, allowing the opportunity for repeat EPR effect mediated tumour uptake and intra-tumoural drug release events with additional short moderate intensity FUS cycle(s).

Figure 11:
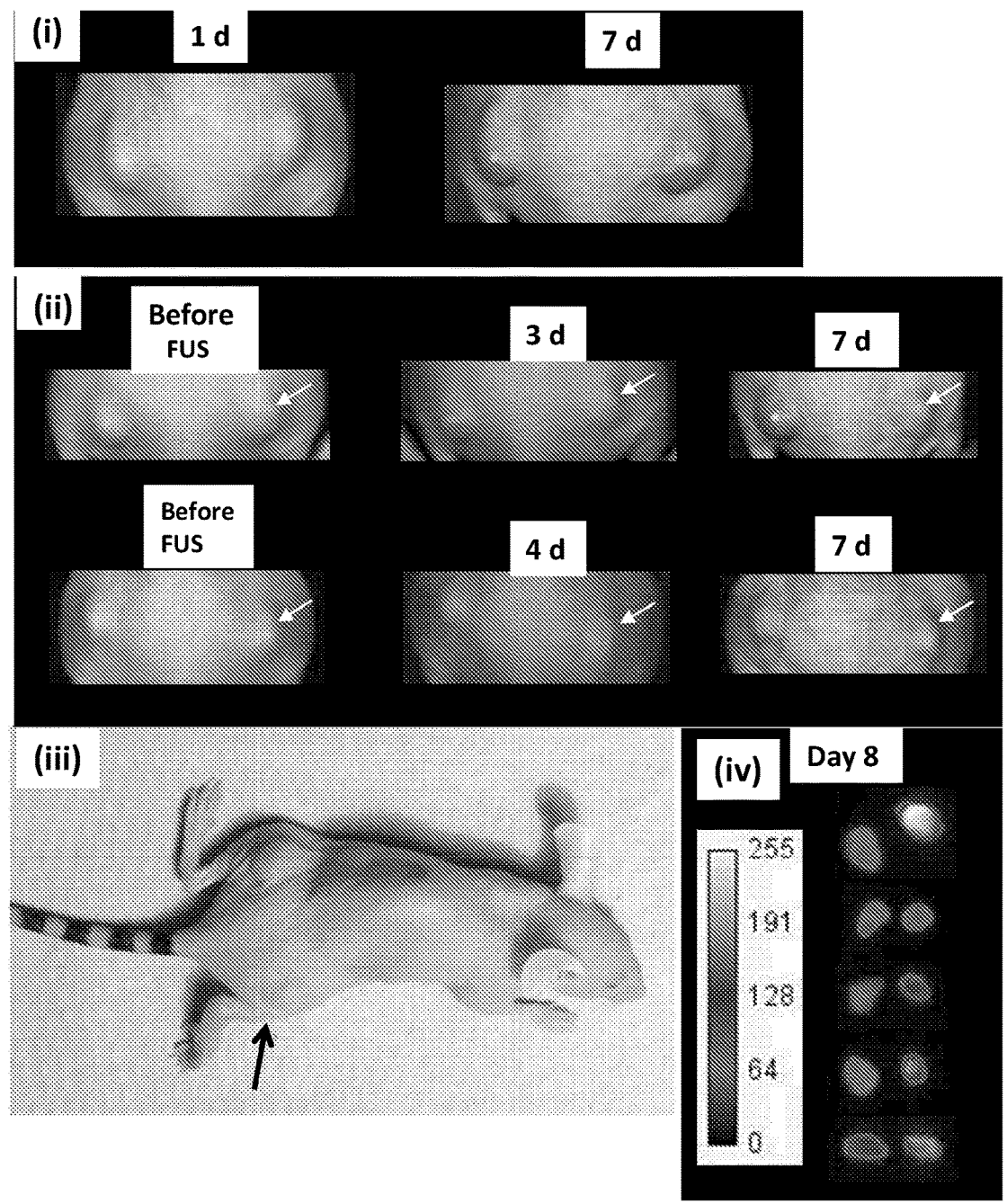
FIG. 11: Effect of thermosensitive liposome (TNP) encapsulating doxorubicin on the right tumour (FUS treated) of a xenograft-bearing mouse. Doxorubicin dosages were matched to those used with Thermodox®. i) Control mice receiving saline; ii) A pair of representative mice receiving doxorubicin-encapsulating thermosensitive liposomes combined with singleFUS treatments (5 min) to the right tumour (imaging at day 0 to day 7); iii) An alternative picture of a representative mouse with an arrow showing the tumour that has been FUS treated' iv) NIRF imaging of excised tumours from mice (N=5), left column is the non-FUS treated tumour, right column is the FUS treated tumour.
Figure 12:
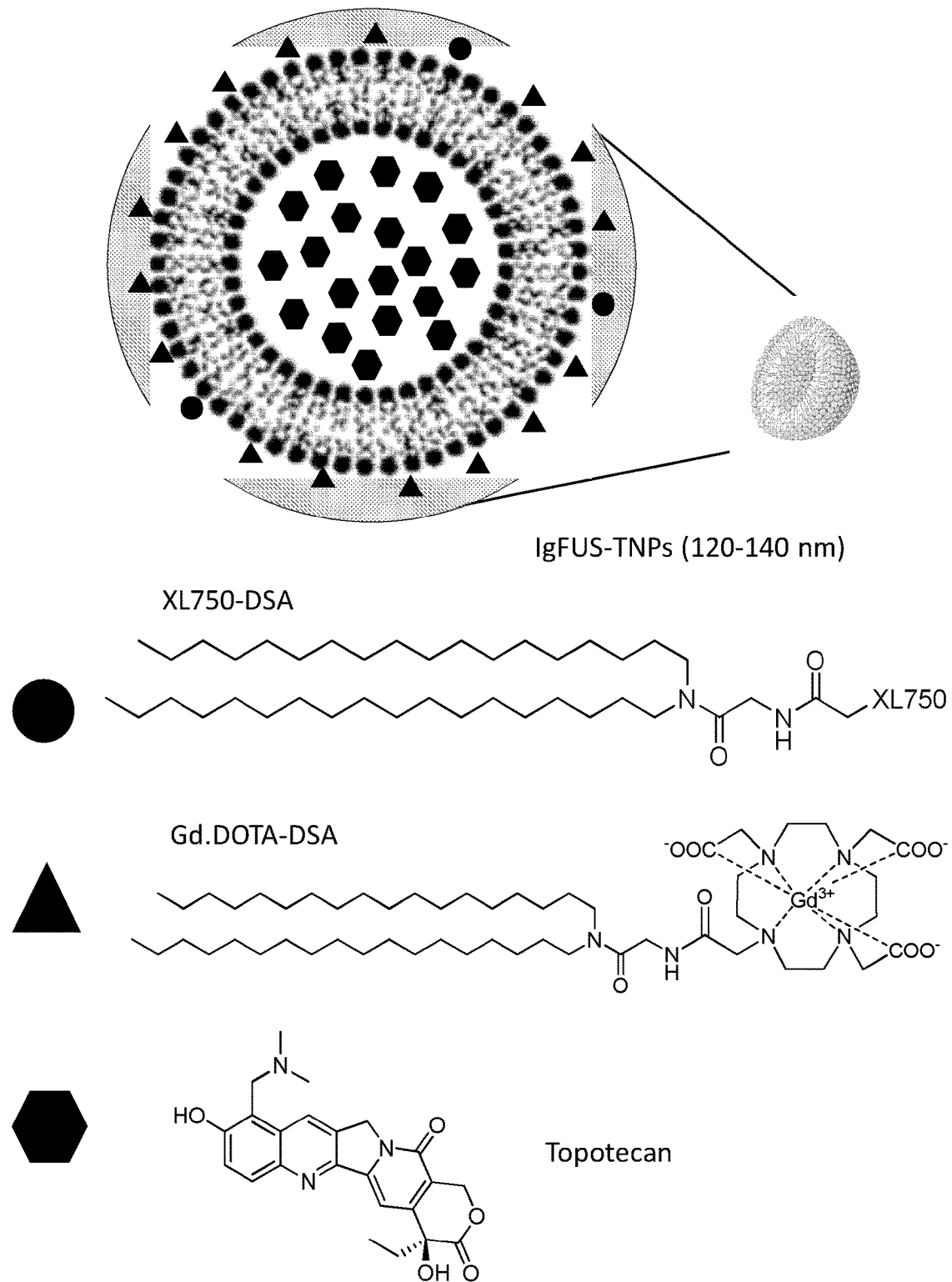
FIG. 12: Structural schematics of the thermosensitive liposomes (TNPs) comprising imaging agents (XL750-DSA and Gd.DOTA-DSA) and active pharmaceutical ingredient (Topotecan).
Figure 13:
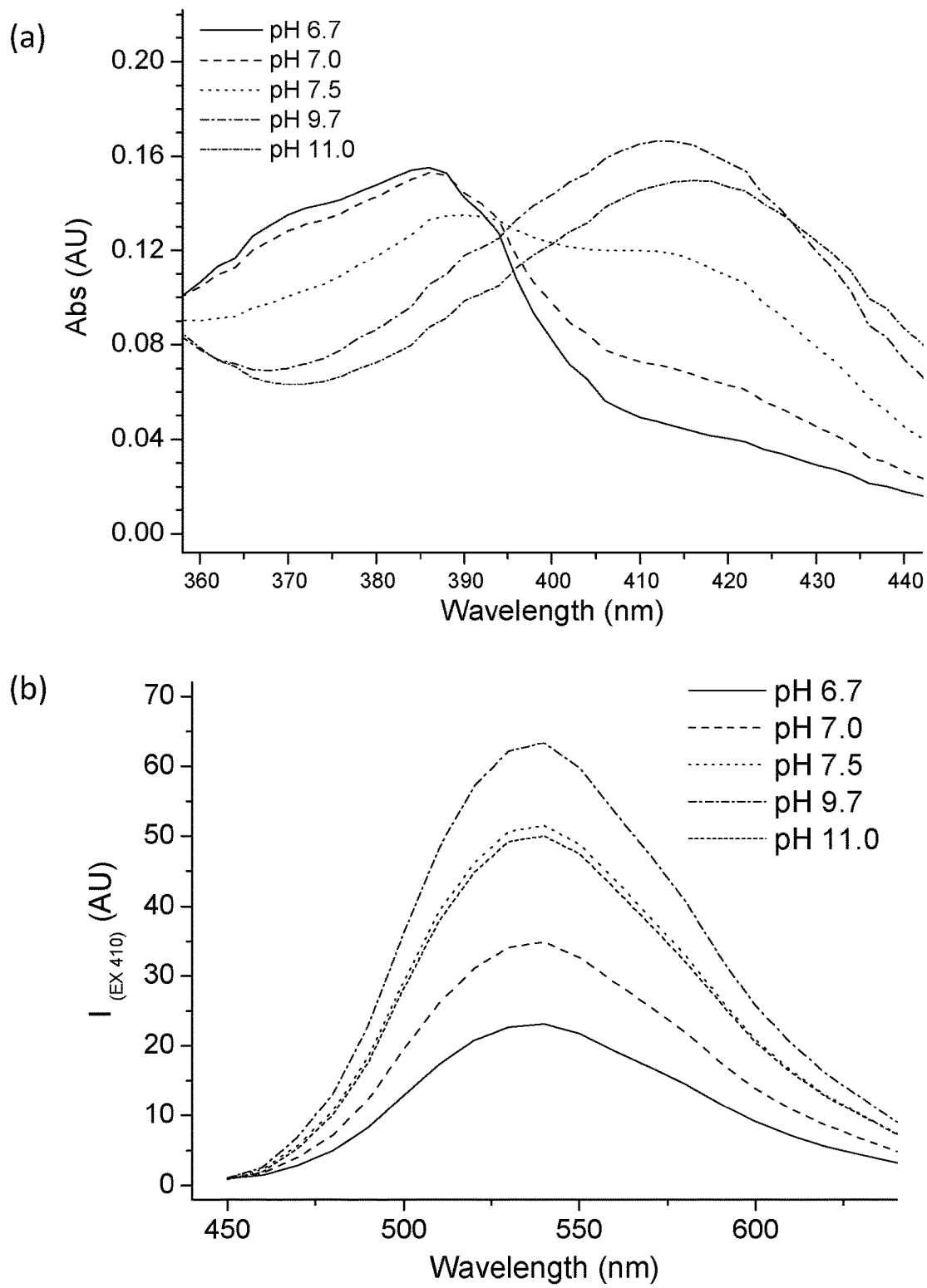
FIG. 13: Spectral properties of aq. topotecan and variance by pH; (a) Absorbance in the visible region is directly affected by buffer pH, with a maximum at ~415 nm shifting to ~385 nm under mild acid or strong basic conditions; (b) This shift strongly influences the intensity of topotecan's intrinsic fluorescence on excitation at 410 nm or (c) 380 nm. Since the 410 nm excitation gives a strong 2-state change as the pH varies from an acidic liposome (IgFUS-TNP) core to the neutral external buffer, this is used to assay topotecan release from liposomes since the resulting fluorescence increase is more easily detected than that of (d) the relatively mild self-quenching effect.
Figure 13:
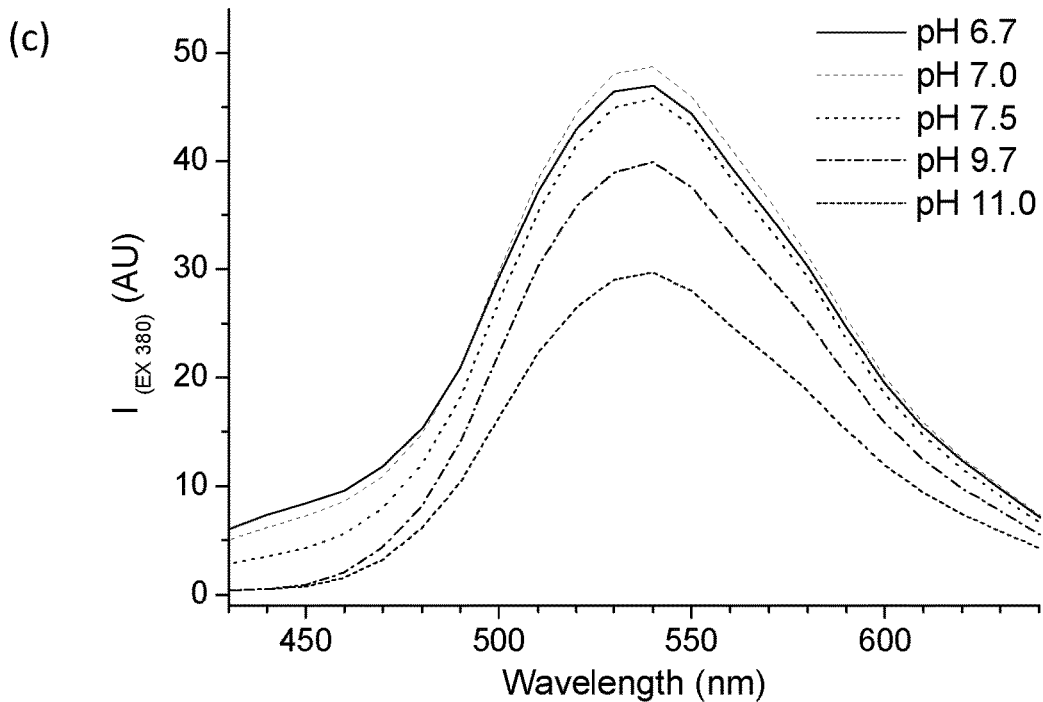
Figure 13:
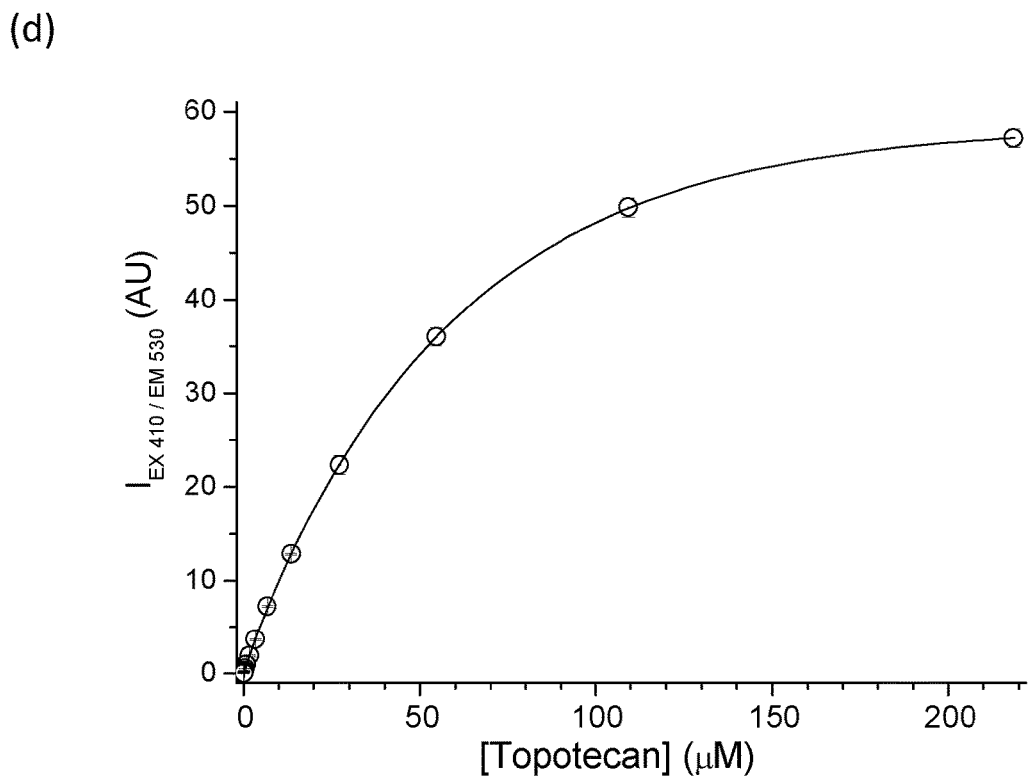

Finally, the primary choice of topotecan in our studies here was for reasons of drug-related fluorescence detection in vivo. This drug binds to topoisomerase I-DNA complex and prevents re-ligation of single strand breaks. Since FDA approved, this with its unique mechanism of action makes it a valuable tool in many treatment regimens. Nevertheless, as we observed in the blood clearance, the free drug is rapidly cleared in the body so ensuring that IgFUS-TNP encapsulation is important (29). However any number of other drugs and/or drug combinations could be encapsulated by IgFUS-TNPs. Of these, doxorubicin is particularly favoured as a potent anti-cancer agent with a reasonably generic use profile (FIG. 11).

In a preferred embodiment, the present invention provides novel TNPs (namely IgFUS-TNPs) that enable real time/diagnostic imaging of nanoparticle mediated delivery of an encapsulated drug, making use of clinically relevant imaging modalities (NIRF and MRI). Image-guidance in turn enables the application of short, moderate intensity FUS pulses that synergize with the IgFUS-TNPs in the blood pool to promote massively FUS treated tumour entry by an EPR effect mechanism and set up the possibility for substantial FUS triggered controlled drug release within the FUS treated tumour volume. Should these effects be translated to the clinic, then there is every reason to believe that the synergistic combination of IgFUS-TNPs and short, moderate intensity FUS pulses could result in substantial benefits to chemotherapy patients and substantially improve the standard of care associated with the chemotherapy of many cancers, both primary and metastatic.

All publications and patent applications mentioned in this specification are indicative of the level of those skilled in the art to which this invention pertains. All publications and patent applications are herein incorporated by reference to the same extent as if each individual publication or patent application was specifically and individually to be incorporated by reference.

Although the foregoing invention has been described in some detail by way of illustration and example for purposes of understanding, it will be clear to those skilled in the art that certain changes and modifications may be practiced within the scope of the appended claims.

The following Examples illustrate the invention:

EXAMPLES

Example 1

Gd.DOTA.DSA-Containing Lipid Nanoparticles

Materials and Methods
General Methods
1,2-Dipalmitoyl-sn-glycero-3-phosphocholine (DPPC; 16:0 PC), 1,2-distearoyl-sn-glycero-3-phosphocholine (DSPC; 18:0 PC), 1-stearoyl-sn-glycero-3-phosphocholine (MSPC; 18:0 Lyso PC) and (ω-methoxy-polyethylene glycol 2000)-N-carboxy-1,2-distearoyl-sn-glycero-3-phosphoethanolamine (PEG$^{2000}$-DSPE) were purchased from Sigma Aldrich (St. Louis, Mo., USA) or Avanti Polar Lipids (Alabaster, Ala., USA). DOTA-NHS-ester was purchased from Macrocyclics (Dallas, Tex., USA) and XenoLight750-NHS-ester from Perkin Elmer (Waltham, Mass., USA). Cell media were from Life Technologies (Carlsbad, Calif., U.S.) while other materials were from Sigma-Aldrich and were of analytical grade. Other lipids were synthesised as described below. $^1$H (400 MHz) and $^{13}$C (100 MHz) NMR spectra were recorded on a Bruker Advance 400 spectrometer using residual chloroform or dichloromethane as internal standards. Results are reported as chemical shifts in ppm from TMS, with peaks described as s=singlet, br=broad singlet, d=doublet, t=triplet, q=quartet, m=multiplet, and coupling constants J given in hertz (Hz). Mass spectroscopy was carried out on a Thermo LCQ DECA XP or Agilent HP1100 MSD spectrometers depending on availability. Analytical HPLC was carried out using an Agilent 1100 series instrument equipped with a multi-wavelength diode array detector, a 1260 Infinity fluorescence detector, a Polymer Laboratories PL-ELS-2100 evaporative light scattering detector, and a 5 cm Hypersil C18 5 µm reverse-phase column. Synthesised lipids were analysed using gradient: 0 min, 100% water, 2.5 mL/min; 1 min, 100% water; 11 min, 100% MeCN; 11 min, 100% MeCN; 23 min, 100% methanol; 25 min, 100% methanol; 27 min, 100% water, 1.8 mL/min; 30 min, 100% water, 2.5 mL/min and showed purity at least 95%. Thin Layer Chromatography (TLC) was carried out on F254 silica gel 60 plates, with spots visualised by UV illumination or vanillin/ninhydrin staining and developed with a heat gun. Flash column chromatography was performed on 40-63 µm silica gel.

Synthesis of Lipids
N,N-Distearylamidomethylamine (DSA) was synthesised according to Kamaly et al. (400 MHz; CD$_2$Cl$_2$; 296 K) δ 3.84 (s, 2H, OCC$\underline{H}_2$NH$_2$), 3.29 (t, J=8.0 Hz, 2H, OCNCH$_2$), 3.11 (t, J=7.8 Hz, 2H, OCNCH$_2$), 1.50 (m, 4H, OCNCH$_2$C$\underline{H}_2$), 1.25 (s, 60H, alky chain CH$_2$), 0.88 (t, J=6.3 Hz, 6H, CH$_3$); $^{13}$C (100 MHz; CD$_2$Cl$_2$; 296 K) δ 166.6 (OCN) 48.8 & 48.1 (OCN$\underline{C}$H$_2$), 41.6 (OC$\underline{C}$H$_2$NH$_2$), 31.1 (CH$_3$CH$_2$$\underline{C}$H$_2$), 30.9-30.8 (alkyl chain CH$_2$), 29.9 (OCNCH$_2$CH$_2$$\underline{C}$H$_2$), 28.8-28.3 (OCNCH$_2$$\underline{C}$H$_2$CH$_2$), 24.2 (CH$_3$$\underline{C}$H$_2$), 15.4 (CH$_3$). TLC (15% MeOH in CH$_2$Cl$_2$ with 0.5% NH$_3$) gave R$_f$ 0.55 with the DSA spot showing red after sequential vanillin and ninhydrin stains. HPLC t$_R$=13.3 min; ESI-MS [M+H]$^+$ 579.7 m/z (expect 578.6 m/z for C$_{38}$H$_{78}$N$_2$O).

N'-XenoLight750-N,N-distearylamidomethylamine (XL750.DSA). DSA (4.2 mg; 7.3 µmol; 1) was dissolved under nitrogen in dry DCM (0.2 mL) with distilled triethylamine (20 µL, 0.14 mmol). XenoLight750-NHS (1 µmol) dissolved in dry DMSO (100 µL; requires vigorous vortexing) was added, the flask protected from light and gently stirred. TLC (15% methanol in CH$_2$Cl$_2$ with 0.5% NH$_3$) showed conversion of separate DSA (R$_f$ 0.55) and XenoLight750-NHS (R$_f$ 0.10) spots to a streak (R$_f$ 0.40-0.65) over 5 hours. The reaction was then stopped and dried in vacuo before purification by flash column chromatography (2 mL) loaded in CH$_2$Cl$_2$ and eluted with 5% (DSA; colourless); 15-20% (conjugate; blue; R$_f$ 0.65); then 30% (side product; colourless; R$_f$ 0.45-0.55) MeOH with unconjugated dye retained on the column. The XL750-DSA fractions were combined and dried in vacuo to give a dark-blue solid with an estimated 70% yield. This was dissolving to 1 mg/mL in chloroform and then stored at −20° C. (400 MHz; CD$_2$Cl$_2$/CD$_3$OD; 296 K) δ 7.62 (m, 3H, dye), 7.48 (m, 3H, dye), 4.11 (m, 5H, dye), 3.85 (m, 2H, OCC$\underline{H}_2$NH$_2$), 3.33 (s, 2H, OCNCH$_2$), 3.26 (s, 3H, dye), 3.12 (s, 2H, OCNCH$_2$), 3.00 (q, 4H, dye), 2.04 (s, 3H, dye), 1.59 (m, 4H, OCNCH$_2$C$\underline{H}_2$), 1.27-1.18 (m, 60H, alkyl chain CH$_2$), 0.82 (t, J=7.5 Hz, 6H, CH$_3$); $^{13}$C (100 MHz; CD$_2$Cl$_2$; 296 K) δ 131.3 (dye), 129.1 (dye), 70.8 (dye), 68.4 (dye), 46.4 (OCNCH$_2$), 39.2 (OC CH$_2$NH$_2$), 34.7 (dye), 30.7-29.3 (alky chain CH$_2$), 24.1 (dye), 23.4 (CH$_3$CH$_2$), 14.2 (CH$_3$), 11.1 (dye), 8.8 (dye). The structure of the XenoLight750 dye is unavailable so assignment information is limited. HPLC t$_R$=26.7 min; λ$_{abs}$/λ$_{em}$ (CHCl$_3$) 755/775 nm.

Gadolinium (III) 2-(4,7-Bis-carboxymethyl-10-[(N,N-distearylamidomethyl-N'-amidomethyl]-1,4,7,10-tetraaza-cyclododec-1-yl) acetic acid (Gd.DOTA.DSA) was synthesised by adaption of the protocol of Kamaly et al. (17). In brief, DOTA-NHS-ester (100 mg, 0.120 mmol) and DSA (80.2 mg, 0.139 mmol) were dissolved in dry CH$_2$Cl$_2$ (40 mL). Distilled Et$_3$N (67 μL, 0.48 mmol) was added and the mixture stirred under N$_2$ for 12 h at 35° C. The solution was dried in vacuo and purified by flash chromatography loaded in 10% CH$_2$Cl$_2$:MeOH:NH$_2$ (34.5:9:1) mixture in CH$_2$Cl$_2$ and eluted with increasing concentration to 100% of the solvent mixture. Fractions containing the target were identified by HPLC, combined and dried to give white hydroscopic solid (57.0 mg; 49%). $^1$H (400 MHz; CD$_2$Cl$_2$/CD$_3$OD) δ 3.45 (br, 2H, NCH$_2$CONH), 3.10 (br, 6H, NC H$_2$COOH), 3.00 (br, 2H, OCNCH$_2$), 2.80 (br, 16H, NCH$_2$C H$_2$N), 2.28 (br, 2H, OCNCH$_2$), 2.16 (br, 2H, OCCH$_2$NH), 1.44 (m, 4H, OCNCH$_2$CH$_2$), 1.18 (s, 60H, alky chain CH$_2$), 0.80 (t, J=6.6 Hz, 6H, CH$_3$). $^{13}$C (100 MHz; CD$_2$Cl$_2$/CD$_3$OD; 296 K) δ 47.0 (OCNCH$_2$), 41.5-38.5 (NCH$_2$CH$_2$N & NCH$_2$COOH), 32.3 (CH$_3$CH$_2$CH$_2$), 31.5-28.5 (alkyl chain CH$_2$), 22.9 (CH$_3$CH$_2$), 14.1 (CH$_3$); others could not be distinguished. HPLC t$_R$=21.2 min; ESI-MS [M+H]$^+$ gave 965.7 m/z (expected 964.8 for C$_{54}$H$_{104}$N$_6$O$_8$) with major fragments seen at 579.6, 522.3, 444.1 and 387.1 m/z corresponding to DSA 1, (C$_{18}$)$_2$NH, DOTA-glycine and DOTA respectively. Gadolinium complexation was effected by suspension of DOTA-DSA (25.2 mg, 0.026 mmol) in a vigorously stirred aqueous solution (5 mL) of gadolinium (III) chloride hexahydrate (11.2 mg, 0.03 mmol) heated at 90° C. for 12 h under N$_2$. After settling, the excess water was removed and minimal CH$_2$Cl$_2$ added to dissolve the lipid complex. After vigorous mixing with equal amounts of deionised water, the emulsion was separated by centrifugation and the CH$_2$Cl$_2$ layer collected and dried in vacuo to give a white power (27 mg; 95%). HPLC t$_R$=21.4 min; ESI-MS [M+H]$^+$ gave 1120.6 m/z or [M-H]$^-$ 1118.7 m/z (expected 1119.7 for C$_{54}$H$_{101}$GdN$_6$O$_8$) with major fragments seen at 1076.5, 1032.5, 1005.7, and 988.8 m/z (all+p ESI) corresponding to loss of COO, 2× COO, 2× CH$_2$COO, and 3× COO respectively.

Preparation of Topotecan-Encapsulating IgFUS-TNPs

All lipids were stored in aliquots (10 mg/mL) in either CHCl$_3$, MeOH/CHCl$_3$ 50:50 (v/v) or MeOH. IgFUS-TNPs were prepared with the following lipid formation; Gd.DOTA.DSA/DPPC/DSPC/MSPC/PEG$^{2000}$-DSPE/XL750.DSA, 30:54:5:5:6:0.05 (m/m/m/m/m/m). Lipid stocks were combined in a round bottom flask in proportion to their respective mol % values (total mass of lipid 30-40 mg, as appropriate). The solvent was slowly evaporated in vacuo to ensure a thin and even film formation. This was hydrated in 300 mM ammonium sulphate, pH 4.0 (1 mL) and XL750.DSA freeze/thaw (×5) by alternately plunging into liquid nitrogen and then hot water to fragment the film. The resulting suspension was sonicated at 60° C. for just long enough to form a homogeneous, milky blue/white liquid. This was then extruded through a 100 nm polycarbonate membrane using a Northern Lipids (Burnaby, Canada) LIPEX extruder heated to 55° C. and pressurised to about 10-20 bar. The external buffer was exchanged to sterile 20 mM HEPES pH 7.4 with 5% glucose (w/v) using a PD10 size exclusion column (Amersham, Buckinghamshire, UK). The resulting, slightly cloudy, blue suspension was sized using a Nanoseries Nano ZS (Malvern Instruments, Worcestershire, UK) before incubation with topotecan hydrochloride (1 mg/mL aq.) at 38.0° C. for 2 h. This drug-loading step was performed using a Thermocycler (Mastercycler Personal, Eppendorf, Stevenage, UK) in order to provide accurate temperature control. Excess, non-encapsulated drug was removed using a PD10 column loaded with HEPES buffer, giving a clear, yellow/green suspension. The size of the topotecan-encapsulated IgFUS-TNPs was recorded using a sample (100 μL) that was then employed to quantify the lipid and topotecan concentrations while the remainder was stored at 4° C. Lipid concentrations were determined using a modified version of the Stewart assay. In brief, IgFUS-TNP samples (50 μL) were mixed with water (150 μL) and MeOH:CHCl$_3$, 1:1 (v/v) (200 μL) then vortex mixed with vigour giving an emulsion. The sample was centrifuged (4000 g; 2 min) to separate fully organic and aqueous layers. Thereafter, an aliquot (70 μL) of the organic layer was combined with Stewart reagent (5 μL, FeCl$_3$/NH$_4$SCN aq.), and the combination vortex mixed again then centrifuged. Finally, an aliquot (50 μL) was then transferred to a glass 96-well plate (Cayman Chemical, Ann Arbor Mich., USA) and A$_{455}$ value measured on a plate reader (Infinite 200 Pro, Tecan, Mannedorf, Switzerland) for comparison with known standards. The topotecan concentration was measured by HPLC using the method described below.

Triggered Drug Release In Vitro

Triggered drug release from topotecan-encapsulated IgFUS-TNPs was assessed by fluorescence. Topotecan has a UV/visible absorbance profile that is pH-sensitive and undergoes a red shift from an A$_{max}$ value of 385 nm at pH~6.5 to a value of 414 nm at pH>7.5. In a similar way topotecan solutions that are acidic are colourless, and those that are neutral/basic are coloured yellow. Since the central cavity of IgFUS-TNPs is maintained at pH 6.5. The intrinsic drug-fluorescence emission maximum, I$_{max}$, also undergoes an increase in quantum yield post transfer from an acidic to neutral/basic pH environment. Accordingly, topotecan drug release from IgFUS-TNPs (internal cavity pH~6.5) into neutral/basic solution is similarly accompanied by a corresponding increase in fluorescence quantum yield. Hence, by measuring changes in fluorescence intensity as a function of time upon incubation of IgFUS-TNP preparations at various temperatures, extent of drug release could be observed in real time. Studies were carried out with separate samples (50 μL) of IgFUS-TNPs diluted 1:20 (v/v) then incubated in a Thermocycler (37-41° C.; 0-15 min) before being cooled to ambient temperature. After transfer to a 96-well plate, the absorbance (414 nm; b.w. 9 nm) and fluorescence (Ex 414 nm b.w. 9 nm; Em 530 nm b.w. 20 nm) emanating from individual samples were measured using a Tecan plate reader.

Pharmacokinetics of Topotecan Quantification by HPLC

Balb C Mice were injected with IgFUS-TNPs encapsulating topotecan (8 mg/kg per mouse body weight) and drug pharmacokinetics monitored by blood sample analyses. Blood samples (50-100 μL) were collected at time intervals (2 min-4 h) and transferred into pre-weighed plastic vials containing heparin (5 uL). Cold methanol (100 μL) was added to each and the mixed samples stored over dry ice or at −20° C. until required. After thawing, each vial was weighed again and the difference used to estimate then original sample volume. The mixtures were centrifuged (3000 g; 4 min) to precipitate cells and a sample of the resulting plasma (50 μL) transferred to a 0.22 μm centrifuge tube filter (Spin-X; Nylon) with deionised water (450 μL). These tubes were centrifuged again and the filtrate transferred to covered HPLC vials. Batches of 5 samples were analysed three times using an Agilent 1100 HPLC equipped with a cooled sample chamber (8-12° C.), a guarded Thermo Hypersil 30×4.6 mm, 5 μm C18 column, a Diode Array Detector (UV/vis absorbance) and an Agilent 1260 Infinity fluorescence detector. Samples were loaded in deionised water containing 0.1% trifluroacetic acid and eluted with acetonitrile using the gradient: 0 min 0%, 1.5 min 0%, 5 min 50%, 6 min 50%, 7 min 0%, 8.5 min 0% and a flow rate of 3.5 mL/min. Detection was by absorbance (210/254/280 nm for proteins and other biologicals; 380 nm for topotecan; all using a bandwidth of 8 nm c.p. reference at 700 nm) and fluorescence (Ex 400 nm; Em 545 nm; PMT-gain 18). Injections were 5-20 μL depending on the sample concentrations and quantifications were calculated from the fluorescence peak areas after calibration (the detector response was effectively linear over the sensitive range). Topotecan could be reliably identified even at extremely low concentrations (10-20 ng/mL) by its intrinsic fluorescence and retention time (3.33±0.03 min; N=45). Final blood concentrations of topotecan are given after correction for dilution effects during sample preparation but not for the loss due to protein binding. Previous results from 'spiked' blood samples suggestions this loss is around 15-20%.

Cell Culture and Tumor Generation

IGROV-1 (ovarian cancer) cells were routinely cultured in RPMI-1640 medium supplemented with Fetal calf serum (FCS) 10% v/v. When cells reached 80-90% confluence, they were harvested and prepared for implantation in mice. Post harvesting, cells were washed in saline and counted using a haemocytometer. Accordingly with the cell counting an equal volume of saline containing the cells was mixed with matrigel (Geltrex, Gibco). For the tumor generation, 5×$10^6$ cells contained in 50% matrigel mixture were inoculated subcutaneously on both flanks of 8 weeks old SHO mice (Charles River, Germany). After 2 weeks, the formed tumours on each flank had reached an average diameter of 5-6 mm.

Moderate FUS Cycling with TIPS

Accordingly to the different FUS treatment protocols, mice were prepared to receive defined FUS bursts by TIPS (Phillips, Netherlands). First, tissue temperature was monitored by 3 thermocouples placed around the tumour. Thereafter, the target tumour was covered by ultrasound gel and the TIPS placed at a distance of 88 mm from the target. Each FUS cycle was delivered at a frequency of 1 MHz 99.9% cycle duty and 10 to 20 W of acoustic power depending on the local temperature variation required (monitored live). Each moderate FUS cycle was seen to increase target tumour tissue temperatures up to a maximum of 41° C. that was then maintained for a further 3-5 min, the duration of each moderate FUS burst.

Nanoparticles Biodistribution and Drug Release In Vivo

The tumor bearing mice were injected intravenously with IgFUS-TNPs encapsulating topotecan (8 mg/kg per mouse body weight) in an aliquot (200 μL) of sterile 20 mM HEPES pH 7.4 with 5% glucose (w/v). The injections were performed with anaesthetized mice using a syringe driver holding the syringe connected to a cannula inserted in the tail vein of each mouse. The injection rate used was 400 μl/min. Immediately post injection, each anaesthetised animal was placed into the Maestro EX (Caliper US) for imaging. The Maestro settings were adjusted to record topotecan (540 nm) or Xenolight (780 nm) signal. Finally, the images were unmixed (multispectral analysis) using the maestro 3.00 software.

Results

In Vitro Characterisation of Topotecan IgFUS-TNPs

IgFUS-TNPs containing topotecan were prepared using the lipid film technique followed by sequential extrusion though filters. Their average hydrodynamic radius was 143 nm with a polydispersity index of 0.208. The final concentration of encapsulated topotecan was 280 μg/mL per batch corresponding to an average encapsulation efficacy of approximately 30%. Topotecan release from IgFUS-TNPs was monitored In vitro by changes in intrinsic fluorescence (Ex 410 nm, Em 540 nm) of topotecan; the fluorescence quantum yield surges when topotecan is released from low-pH conditions (during encapsulation within nanoparticles) to neutral buffer conditions post release from encapsulation (FIG. 1). Images of IgFUS-TNPs are shown pre- and post-thermally assisted drug release using the MaestroEX bioimager (FIG. 1a). As expected, the Xenolight NIRF signal remains constant pre- and post-drug release, whereas drug fluorescence is quenched from sight pre-drug release but clearly visible post-thermally assisted drug release. Drug release as a function of temperature was followed by also monitoring changes in drug fluorescence over time at different external temperatures (FIG. 1b). In this instance, no change in fluorescence was observed over a 10 min period at 37° C. consistent with nanoparticle stability and stable drug encapsulation. By contrast, changes in drug fluorescence with time were clearly consistent with quantitative drug release over a 5 min period at 41° C. Using this data set, the thermal $T_m$ of our IgFUS-TNPs was estimated as 40° C. (FIG. 1b). Drug release characteristics from our IgFUS-TNPs appear to be sharp and therefore cooperative. Mechanistically speaking, drug release may well be caused by pore formation resulting from thermally induced fluid mesophase transitions in IgFUS-TNP lipid bilayers within which drug is encapsulated (30).

In Vivo Pharmacokinetics of Topotecan and Clearance from Blood

Figure 2:
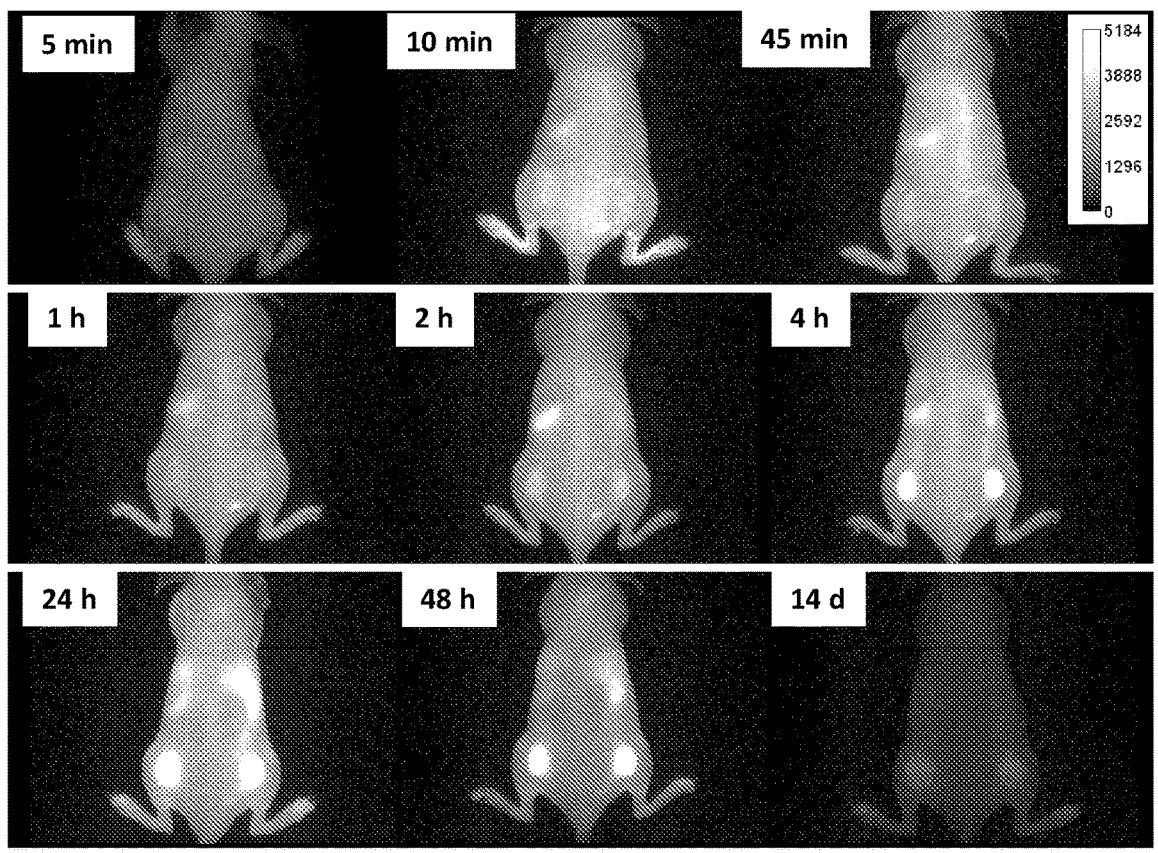
FIG. 2: Pharmacokinetics from thermosensitive liposomes (TNPs) in the absence of FUS treatment. The time points are measured from injection (200 μL; tail i.v.) of thermosensitive liposomes to a xenografted mouse with tumours on each haunch. The mouse was imaged under anaesthetic using a Maestro EX multispectral analyser, with fluorescence excitation at 704 nm and emission collected in 10 nm steps over 740-950 nm. After unmixing of the XL750 signal (in comparison to a sample of IgFUS-TNPs in buffer) the images were stacked, contrast balanced and false coloured using ImageJ.

For the first in vivo experiments, control experiments were performed using IgFUS-TNPs that were administered by i.v.-injection in order to use the Maestro EX to monitor nanoparticle biodistribution as a function of intrinsic NIRF signal intensity over a period of two weeks post injection (FIG. 2). Initially, the biodistribution of IgFUS-TNP associated NIRF signal was found all body, consistent with vascular distribution (blood pool). Subsequently, 1-4 h post injection, the biodistribution began to narrow to liver and tumours. After 24 h, residual nanoparticle biodistribution was entirely localized to tumours and liver only with the blood pool empty. Following this, NIRF signal was followed successfully for a further 2 weeks, allowing us to monitor IgFUS-TNP clearance from both liver and tumour target sites. These observations are broadly supported by the data of other researchers reported in their experiments using Cy5.5 labelled lipid nanoparticles (31), indocyanine green (ICG) chemically modified lipid nanoparticles (32) and PET/fluorescent labelled TSLs (33).

Figure 3:
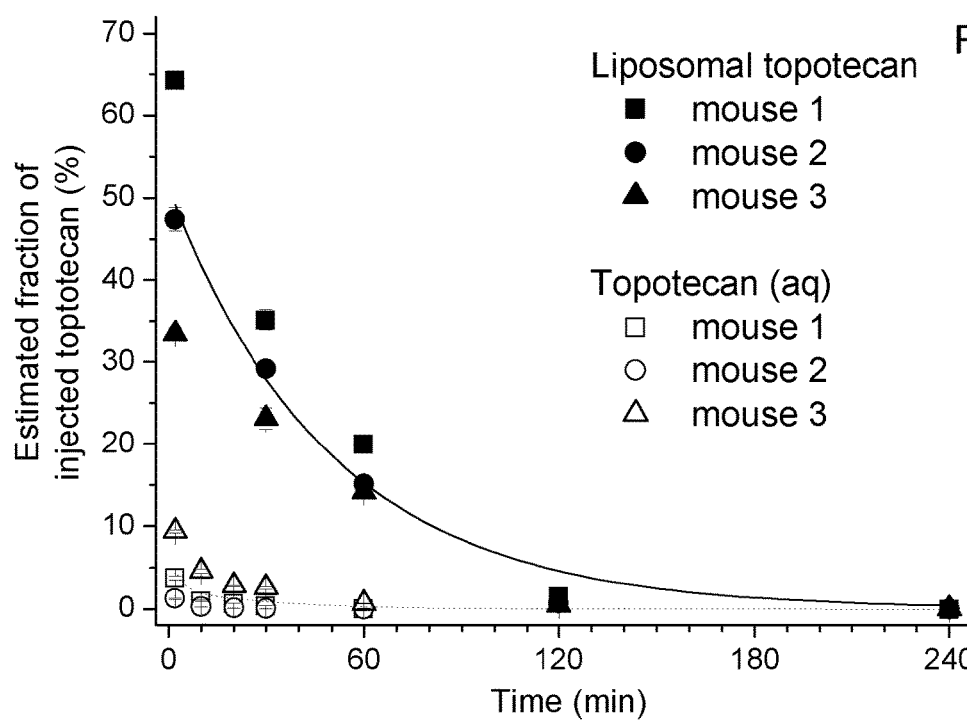
FIG. 3: Drug clearance from the blood, measured by HPLC; Groups of mice (N=3) were injected (i.v. tail) with either topotecan encapsulated in thermosensitive liposomes (IgFUS-TNPs) or a matched concentration of free topotecan in the same buffer. Small (~50 μL) blood samples were then collected over the following 4 hours, before analysis by HPLC (reverse phase C18 column; UV and fluorescence detection).

Topotecan drug pharmacokinetic control experiments were then carried out as follows. Balb C mice were injected (i.v. tail vein) with either IgFUS-TNPs (with encapsulated topotecan) or a concentration matched internal control of free topotecan in the same buffer at equivalent concentration. Drug kinetics were monitored by fluorescence as a function of time (FIG. 3), clearly demonstrating that free drug is cleared from the blood pool in mins, while topotecan encapsulated in IgFUS-TNPs was maintained in the blood pool for several hours. Once again, these observations are broadly supported by the data of other researchers this time using topotecan encapsulated in standard TSLs (34).

Therapy Imaging Probe System (TIPS) and Mild FUS Treatment Regimes

Figure 4:
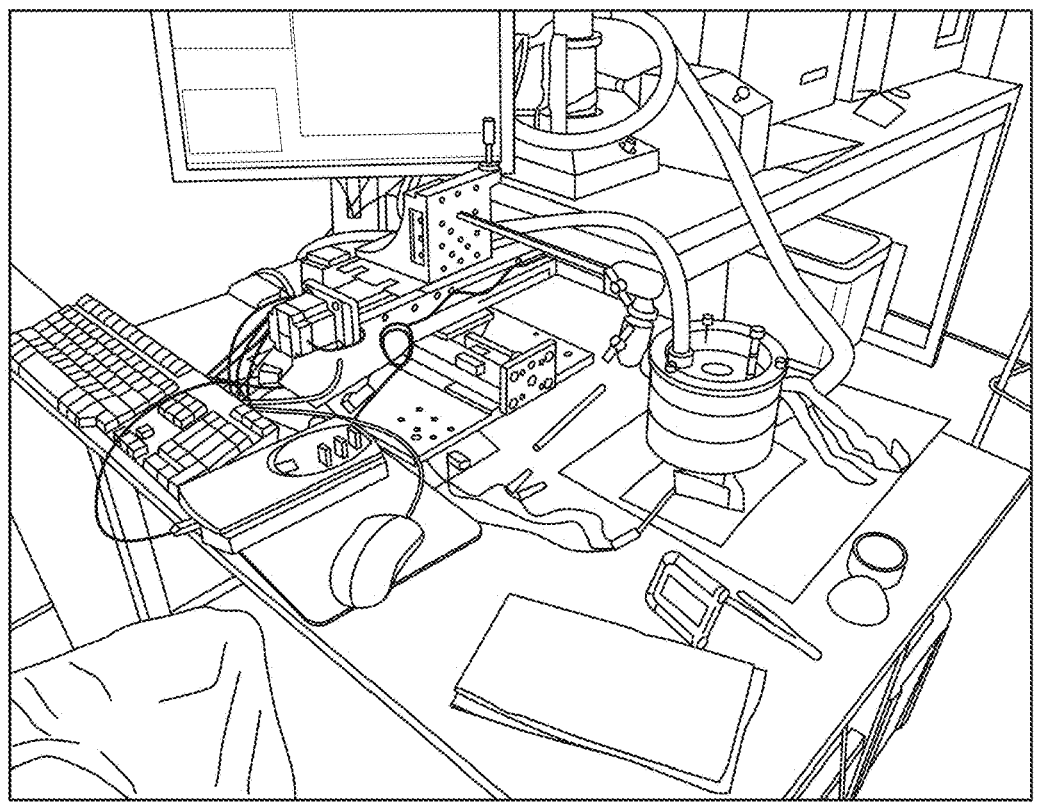
FIG. 4: TIPS focused ultrasound (FUS); (i) overview of the equipment showing the water-filled transducer chamber, the thermocouple interface, and the control PC; (ii) schematic of the in vivo configuration with the transducer (a) raised such that the ultrasound biconic (b) focuses just above the skin surface over the tumour (c). The mouse is surrounded with warmed, degassed ultrasound gel (d) and placed on an ultrasound-absorbing mat (e) to prevent reflections off the table. Temperature monitoring is via three fine-wire thermocouples (f) implanted around the tumour.
Figure 4:
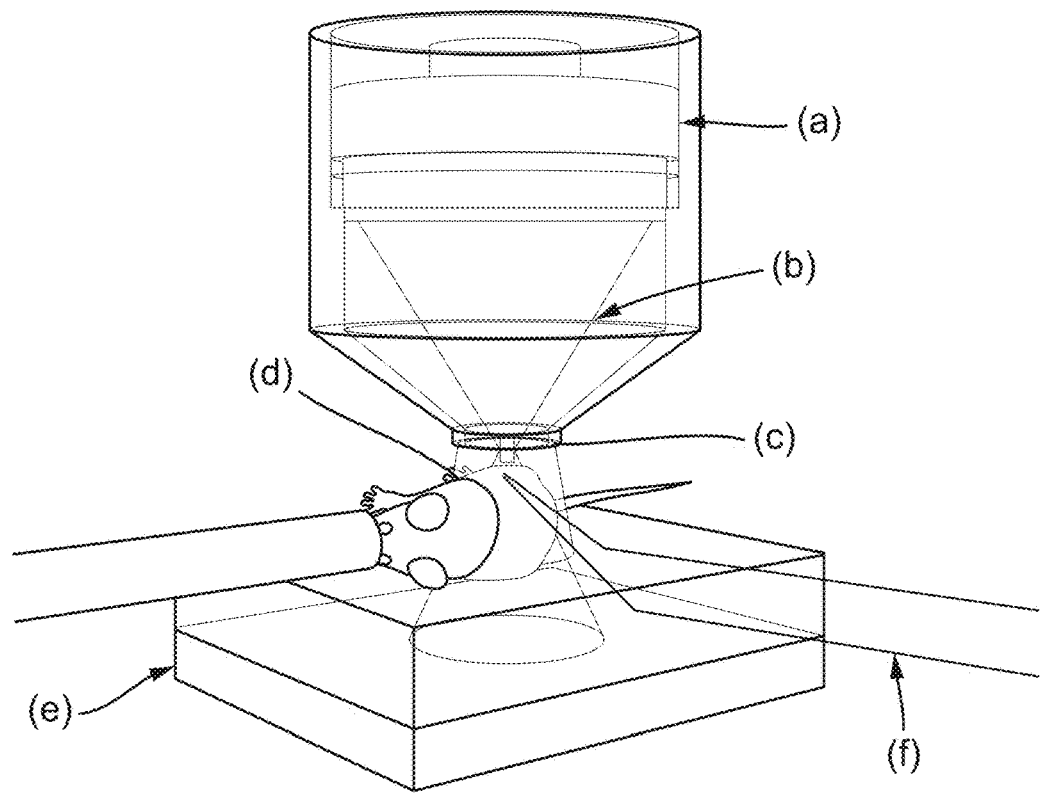
Figure 5:
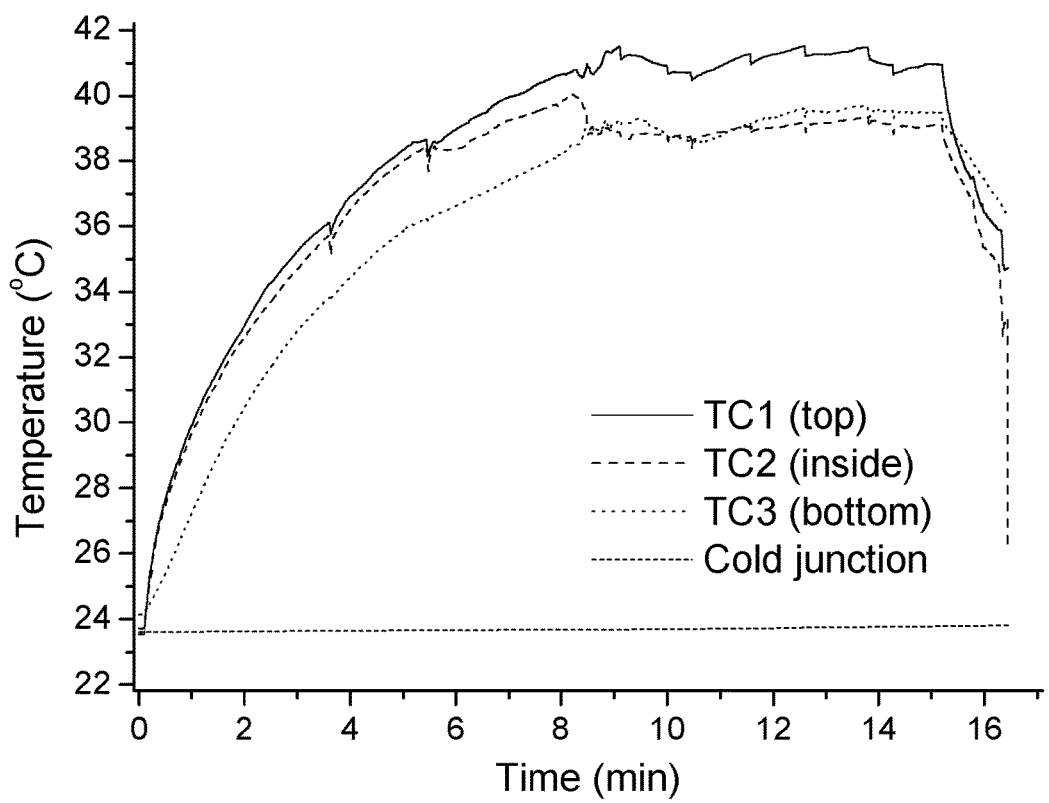
FIG. 5: Temperature data from FUS treatment of right-side tumour. Three thin-wire thermocouples are placed; TC1 is below the skin at the top of the tumour, closest to the transducer face (near field); TC2 is between the tumour body and the underlying muscle; TC3 is at the bottom of the tumour (far field). The cold junction is the temperature of the TC logging unit (~3-4° C. above r.t.). Target is for a tumour average temperature of 39-41° C. for 5 min.

Having confirmed the basic premise that IgFUS-TNPs (with encapsulated topotecan) will adopt a liver and tumour biodistribution with time (post i.v.-injection), and that free topotecan has a limited half life in the blood pool without nanoparticle encapsulation, our approach was then to make use of imaging and controlled application (time, intensity and duration) of FUS in order to improve upon fundamental nanoparticle biodistribution and drug pharmacokinetic behaviour. In order to provide FUS in vivo, we developed a preclinical FUS equipment set up with water-filled transducer chamber and thermocouple interface, all under computer control (FIG. 4). As shown (FIG. 4, right panel), individual mice for FUS treatment were located under a therapy imaging probe system (TIPS) and 3 thermocouples (TC1, TC2 and TC3) were placed around a tumour of interest to closely monitor changes in tissue temperature as a function of the application of short moderate intensity FUS bursts. Each such FUS cycle (3-5 mins) results in local hyperthermia (39-41° C.) in and around the tumour for 5 min post FUS application and with good temperature distribution (FIG. 5). From this data set, we deduced that a preclinical FUS regime is a reliable, controllable and efficient manner to induce tissue hyperthermia.

Single FUS Cycle Protocol and its Effect on IgFUS-TNP Pharmacokinetics

Figure 6:
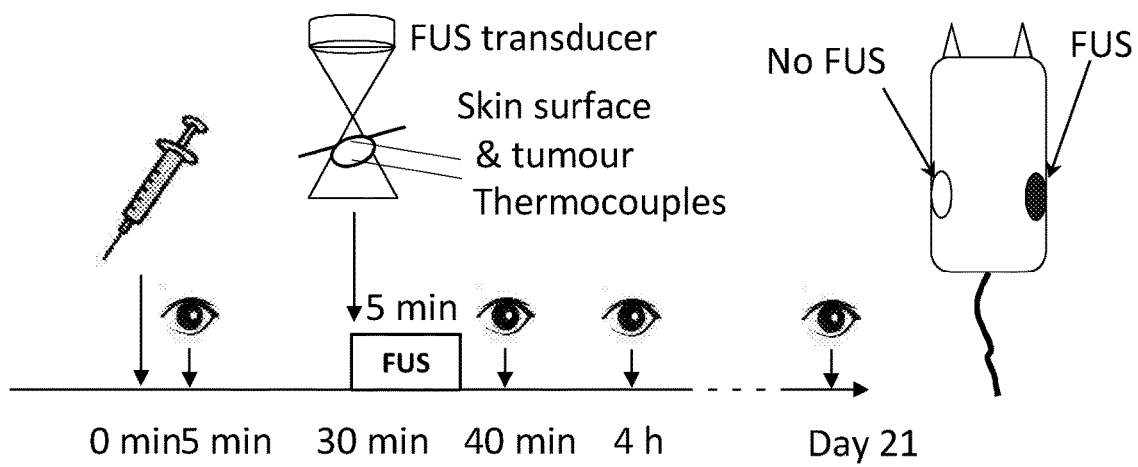
FIG. 6: Schematic of a single, short period, moderate intensity FUS treatment (5 min; <42° C.) to the right-hand-tumour. Time points are given after injection, fluorescence image stacks are collected at intervals up to 21 days.
Figure 7:
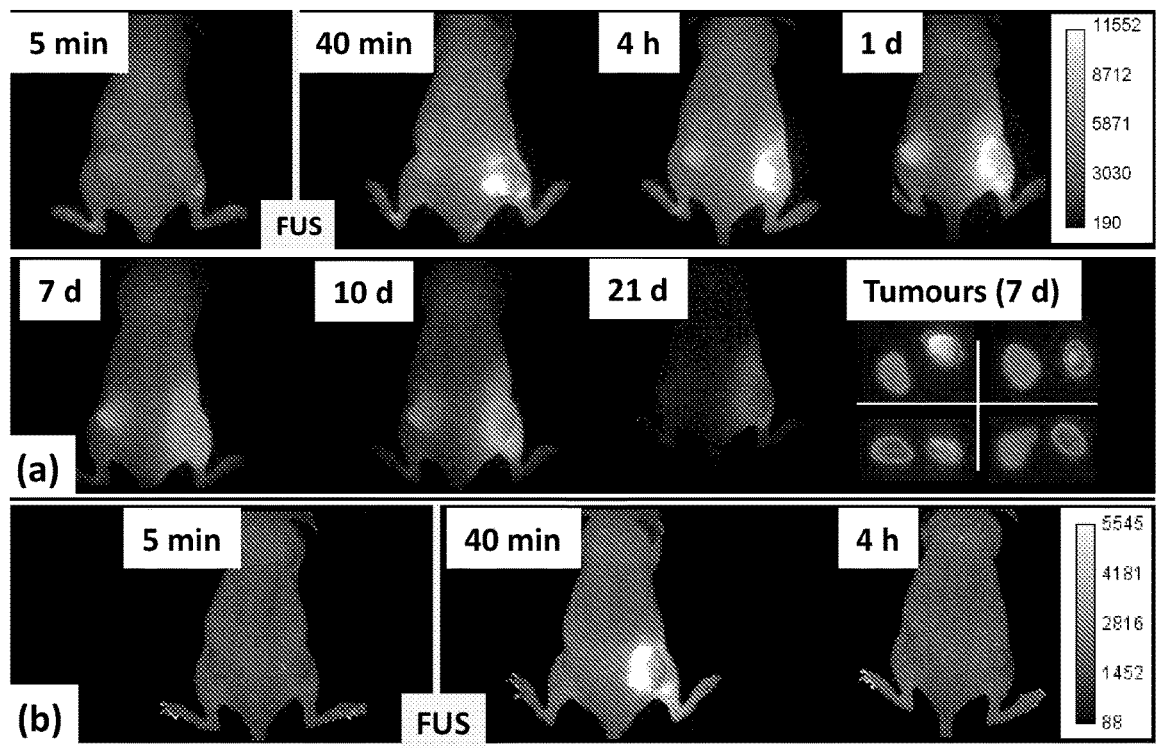
FIG. 7: Changes in thermosensitive liposome (TNP) pharmacokinetics on FUS treatment to the tumour on the right haunch, 30 min after injection (200 μL; tail i.v.). Imaging was carried out as before for XL750 and by monitoring intrinsic topotecan fluorescence by excitation at 455 nm and emission collected in 10 nm steps over 500-720 nm. After unmixing of the XL750 and topotecan signals (in comparison to samples of the IgFUS-TNPs and free drug in buffer) the images were processed as before; (a) full body XL750 images are from one mouse followed for 3 weeks, 4 others were sacrificed after 1 week and the tumours (left and right) excised and imaged for XL750 fluorescence; (b) FUS-induced release of topotecan can be seen as suddenly increased intrinsic fluorescence immediately after treatment. This signal is transient and lost within 4 h.

According to this protocol (FIG. 6), a single, short moderate intensity FUS burst was applied (5 min at 41° C.) 30 min post i.v.-administration of IgFUS-TNPs to one of two flank tumours (the other tumour representing a non-FUS control). Thereafter we observed a very significant increase in NIRF signal intensity in the FUS treated area just 10 min after FUS burst application. This increase in NIRF signal sensitivity then continued for at least 4 h more (FIG. 7). Following these full body images showing NIRF signal intensity increases with time, FUS treated tumours were excised at day 7 and compared with corresponding non-FUS control tumours. These data emphasised the vast difference in NIRF signal between FUS treated tumours and non-FUS control tumours. Our IgFUS-TNPs are charge neutral lipid-based nanoparticles formulated with 6 mol % PEG. Therefore, can be expected to be stable for at least several hours in serum and other biological fluids. Hence, the inescapable conclusion is that a single FUS pulse was sufficient to encourage substantial and selective partition of IgFUS-TNPs from the blood pool into FUS treated tumours. Moreover, the tissue persistence of the NIRF signal in vivo post FUS pulse treatment was found to extend out to at least 3 weeks.

In parallel, changes in topotecan-related fluorescence (Ex 455 nm, Em<600 nm) were monitored in order to determine time and location of drug release from circulating IgFUS-TNPs. In spite of the difficulties in imaging at sub-600 nm wavelengths, substantial topotecan-related fluorescence was observed consistent with substantial drug release from nanoparticle encapsulation immediately within FUS treated tumours, following application of the single FUS pulse. In this instance, drug-related fluorescence did not persist beyond 1 h post FUS burst probably as a result of either drug elimination, drug metabolism or DNA target site intercalation (topotecan is a topoisomerase I inhibitor) (34).

Double FUS Cycle Protocol and the Effect on Drug Delivery

Figure 8:
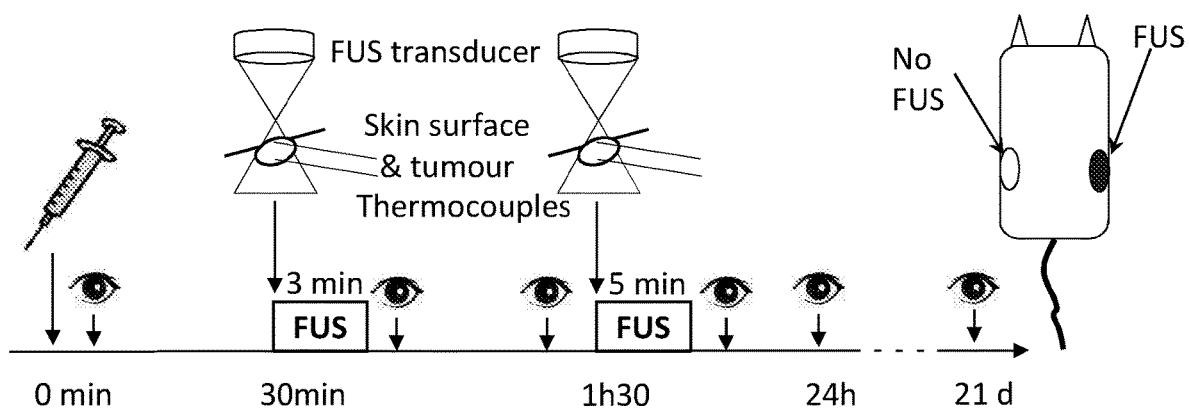
FIG. 8: Schematic of application of two, short period, moderate intensity FUS treatments to the right-hand tumour. This combines an initial treatment (3 min; ~41° C.) at 30 min with a slightly stronger one (5 min; ~42° C.) one hour after. As before, image stacks are collected at time points up to 21 days.
Figure 9:
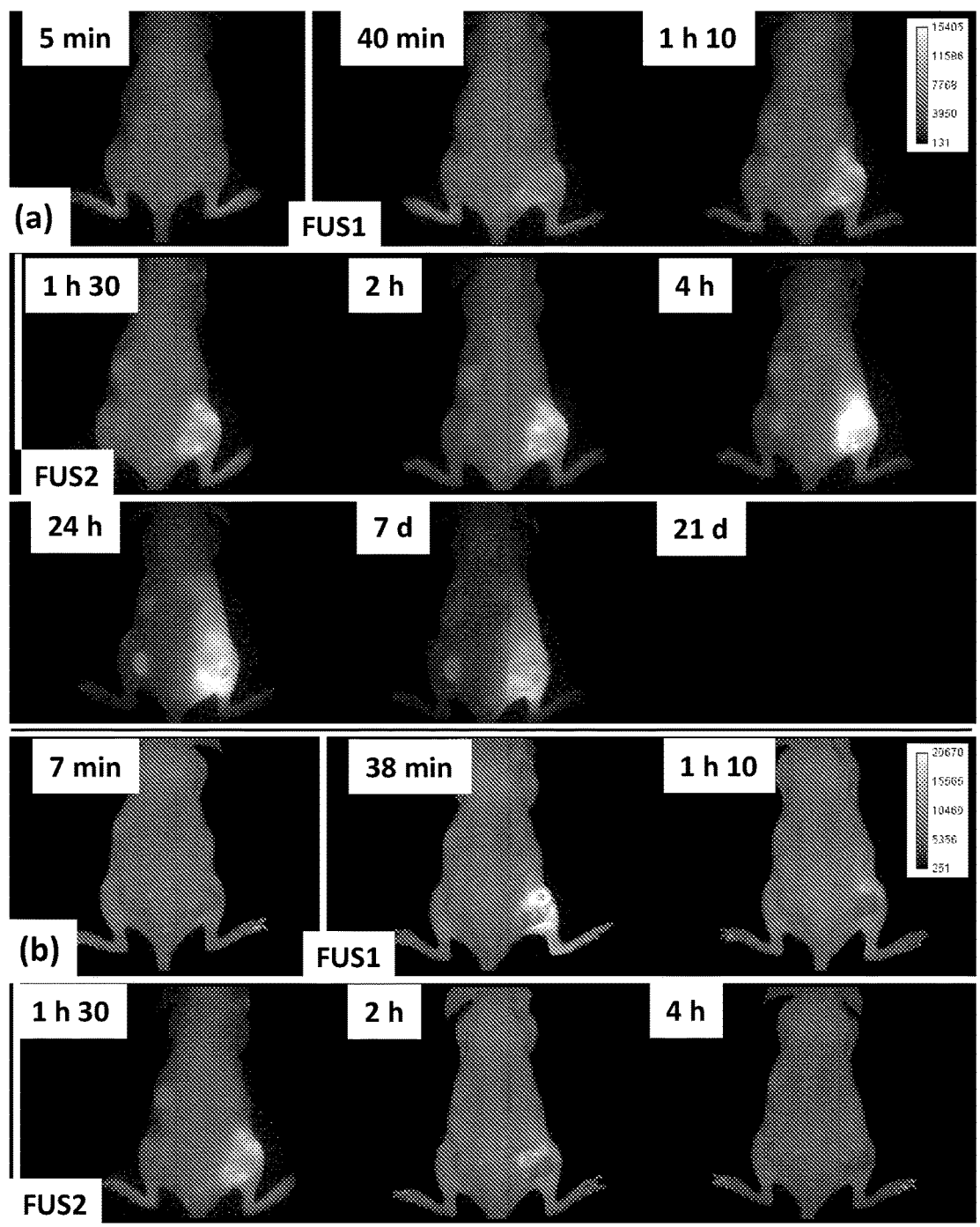
FIG. 9: Two, short period, moderate intensity FUS treatments significantly increase thermosensitive liposome (TNP) uptake and drug release. The protocol used is the same as previously described but with two rounds of FUS at 30 min and 1 h 30. (a) XL750 imaging shows increased thermosensitive liposome uptake after treatment. (b) Intrinsic topotecan fluorescence in also seen to transiently increase after each FUS. Results are from a single representative mouse (N=3).

In order to investigate the consequences of repeat short moderate intensity FUS applications, a double FUS burst protocol was developed (FIG. 8) wherein two such short FUS bursts were applied (3 min then 5 min at 41° C.) 30 and 90 mins post i.v.-administration of IgFUS-TNPs to one of two flank tumours (the other tumour representing a non-FUS control). Prior to the second burst, a substantial build up of IgFUS-TNPs was already observed in the FUS treated tumour, this build up continued apace following application of the second burst (FIG. 9). FUS treatment in this manner is apparently enhancing the enhanced permeability and retention (EPR) mechanism to such an extent that we have induced hyperpermeability and retention (HPR) in effect.

Furthermore, when changes in topotecan-related fluorescence (Ex 455 nm, Em<600 nm) were monitored in the tumour with time, substantial topotecan-related fluorescence was observed post both first and second FUS pulses consistent with substantial FUS induced drug release following both bursts. The implication is that IgFUS-TNPs are recruited from the blood pool to the tumour volume and then act as "storage vesicles" awaiting the opportunity for FUS triggered controlled release of drug in the tumour volume.

Figure 10:
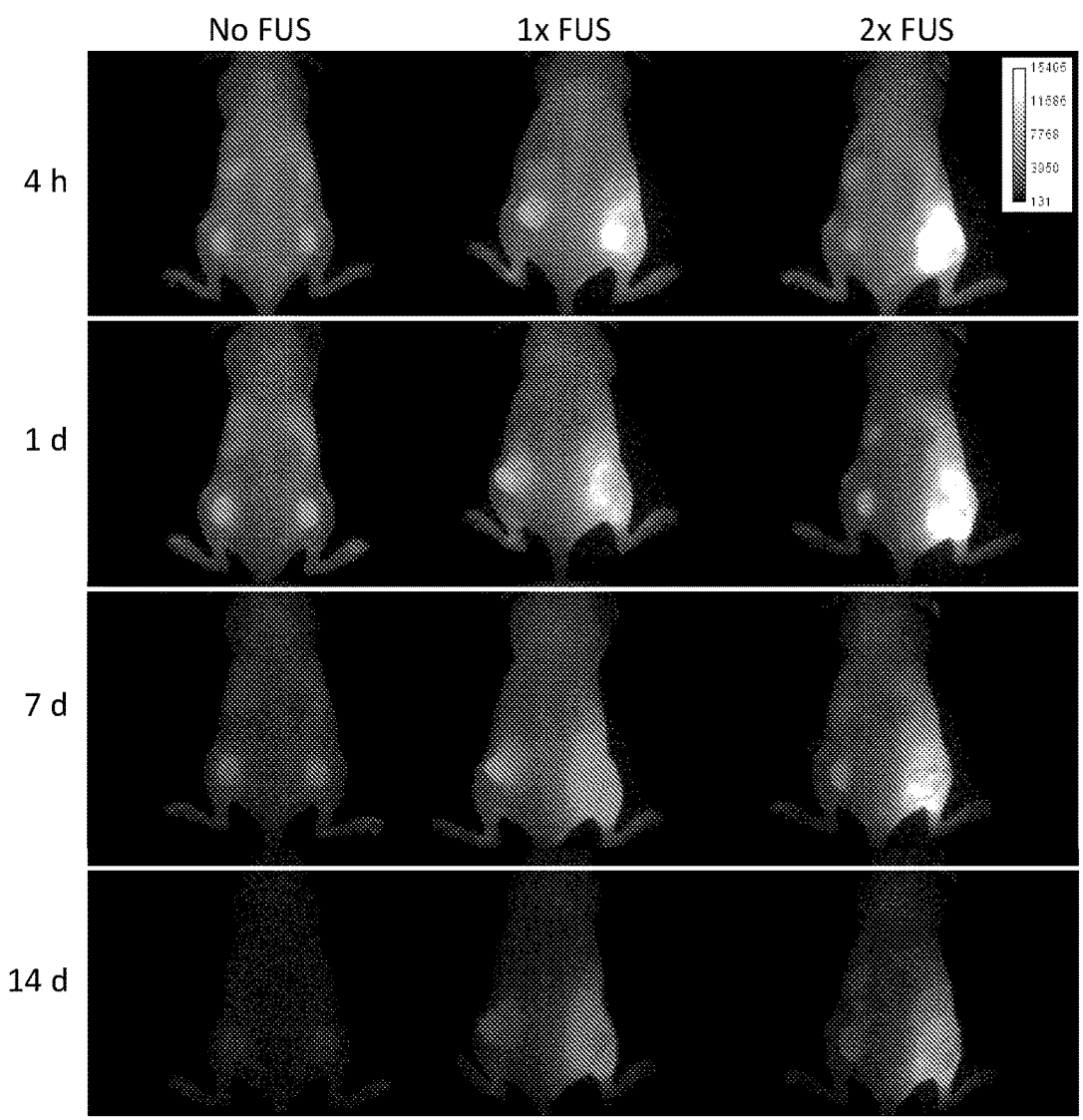
FIG. 10: Comparison of absolute XL750 fluorescence signal intensities at the same time points from mice that underwent none, one or two, FUS treatments.

Overall, the ability of the short moderate intensity FUS cycle regime to encourage IgFUS-TNPs accumulation in tumours was also observed to correlate with enhanced persistence of NIRF signal in the tumour over time (FIG. 10) lasting for at least 7 days before clearance in >two weeks. At this stage, we would suggest that the FUS triggered controlled release of drug in the tumour volume is associated with thermally induced fluid mesophase transitions in IgFUS-TNP lipid bilayers within which drug is encapsulated (as mentioned above). These mesophase transitions could then enable fusion events with cancer cell plasma membranes thereby causing labelling of tumour cell membranes with XL750.DSA lipid, such that these cells are "painted" with NIRF signal for an extended period. The same would be true of Gd.DOTA.DSA lipid, such that cells should also be "painted" with positive contrast agent thereby enabling the visualization of these cells as bright field regions in MRI scans as well (17-23).

Example 2

Chain-Extended Lipids

Synthesis of [Gd]DOTA.AOC.DSA
Scheme 1 Below Shows the Steps used to Obtain [Gd]DOTA.AOC.DSA.

Scheme 1: Synthesis of [Gd]DOTA.AOC.DSA

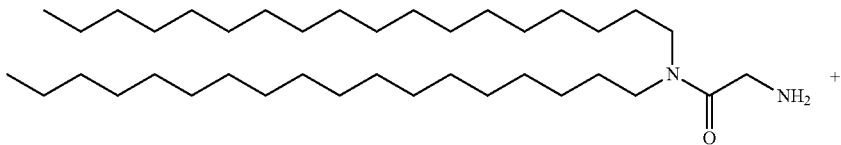

1.

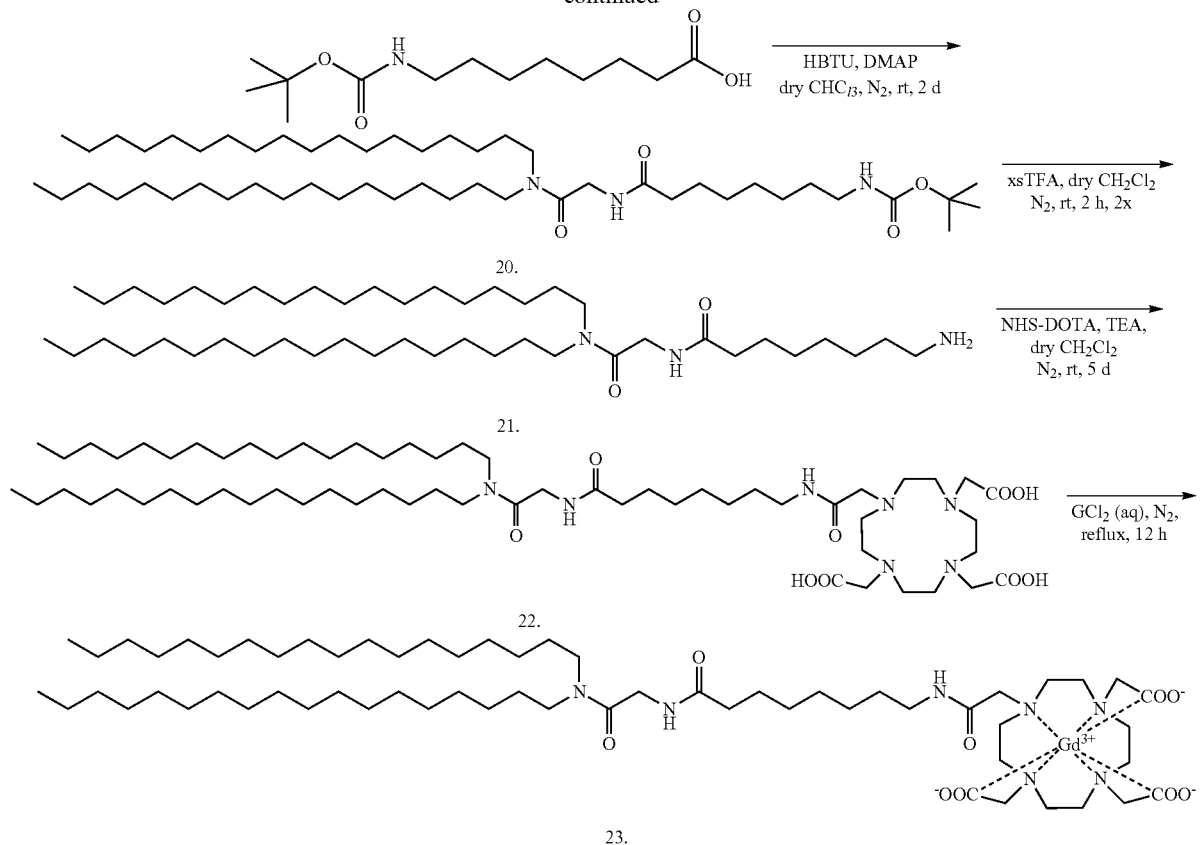

General Methods. DOTA-NHS-ester was purchased from Macrocyclics (Dallas, Tex., USA) and other materials from Sigma Aldrich (St. Louis, Mo., USA) unless otherwise stated. $^1$H (400 MHz) and $^{13}$C (100 MHz) NMR spectra were recorded on a Bruker Advance 400 spectrometer using residual chloroform or dichloromethane as internal standards. Results are reported as chemical shifts in ppm from TMS, with peaks described as s=singlet, br=broad singlet, d=doublet, t=triplet, q=quartet, m=multiplet, and coupling constants J given in hertz (Hz). Mass spectroscopy was carried out on a Thermo LCQ DECA XP or Agilent HP1100 MSD spectrometers depending on availability. Analytical HPLC was carried out using an Agilent 1100 series instrument equipped with a multi-wavelength diode array detector, a 1260 Infinity fluorescence detector, a Polymer Laboratories PL-ELS-2100 evaporative light scattering detector, and a 250×4.6 mm BDS Hypersil Cyano 5 µm column run in normal phase mode. Lipid mixtures were analysed using gradient: 0 min, 100% chloroform, 3 mL/min; 4 min, 100% chloroform; 19 min, 100% methanol; 21 min, 100% methanol; 23 min, 100% chloroform; 27 min, 100% methanol. Thin Layer Chromatography (TLC) was carried out on F254 silica gel 60 plates, with spots visualised by UV illumination and iodine staining. Flash column chromatography was performed on 40-63 µm silica gel with fraction analysis by HPLC and TLC. Reaction glassware was dried at 100° C. under vacuum for at least 30 min before use.

DSA (1) was synthesised according to Kamaly et al. (400 MHz; CD$_2$Cl$_2$; 296 K) δ 3.84 (s, 2H, OCC$\underline{H}_2$NH$_2$), 3.29 (t, J=8.0 Hz, 2H, OCNC$\underline{H}_2$), 3.11 (t, J=7.8 Hz, 2H, OCNC$\underline{H}_2$), 1.50 (m, 4H, OCNCH$_2$C$\underline{H}_2$), 1.25 (s, 60H, alky chain CH$_2$), 0.88 (t, J=6.3 Hz, 6H, CH$_3$); $^{13}$C (100 MHz; CD$_2$Cl$_2$; 296 K) δ 166.6 (OCN) 48.8 & 48.1 (OCNC$\underline{H}_2$), 41.6 (OCC$\underline{H}_2$NH$_2$), 31.1 (CH$_3$CH$_2$C$\underline{H}_2$), 30.9-30.8 (alkyl chain CH$_2$), 29.9 (OCNCH$_2$CH$_2$CH$_2$C$\underline{H}_2$), 28.8-28.3 (OCNCH$_2$C$\underline{H}_2$CH$_2$), 24.2 (CH$_3$C$\underline{H}_2$), 15.4 (CH$_3$). TLC (10% methanol in dichloromethane [DCM] with 0.5% NH$_3$) gave R$_f$ 0.75 with the DSA spot showing red/brown after iodine staining. HPLC t$_R$=8.0 min; ESI-MS [M+H]$^+$ 579.7 m/z (expect 578.6 m/z for C$_{38}$H$_{78}$N$_2$O).

AOC.DSA (21) was synthesised by N,N,N',N'-tetramethyl-O-(1H-benzotriazol-1-yl)uronium hexafluorophosphate/4-(dimethylamino)pyridine (HBTU/DMAP) activated attachment of 8-(BOC-amino)octanoic acid (BOC-AOC-OH), followed by removal of the BOC protecting group with trifluoroacetic acid (TFA). In brief, DSA (1, 1000 mg), BOC-AOC-OH (495 mg), HBTU (800 mg), and DMAP (645 mg) were combined in anhydrous chloroform (50 mL) and stirred under nitrogen at r.t. for 2 days. The resulting suspension was filtered and the brown supernatant dried in vacuo, dissolved in minimal DCM, then water washed and ether extracted/acid & saline washed as for DSA above. The resulting light brown oil gave TLC (10% methanol in DCM with 0.5% NH$_3$) of R$_f$ 0.85 and HPLC t$_R$=2.5 min. The protecting group was removed by a dual treatment with 40 v % TFA in DCM under nitrogen at r.t., for 2 h each. Repeated drying in vacuo and solubilisation into anhydrous DCM (3-4 times) was used to remove the remaining TFA and the product dried to a light brown/orange waxy solid. TLC (10% methanol in DCM with 0.5% NH$_3$) of R$_f$ 0.7 with ~5% trace DSA; HPLC t$_R$=7.7 min; ESI-MS [M+H]$^+$ 720.6 m/z (expect 719.7 m/z for C$_{46}$H$_{93}$N$_3$O$_2$).

DOTA.AOC.DSA (22) was synthesised by base-catalysed reaction with DOTA-NHS-ester. AOC.DSA (21, 1.55 g, without further purification) was dissolved into anhydrous DCM (350 mL) with triethylamine (2 mL) to give a pale yellow/orange solution. DOTA-NHS-ester (1.64 g) was added and the suspension stirred udner nitrogen at ~30° C. for 5 days. The resulting near-clear solution gave HPLC $t_R$=9.5 min with approx. 80% completion. The solvent was removed in vacuo and repeatedly dried from anhydrous DCM to remove the remaining TEA. The resulting tan, waxy, solid gave HPLC $t_R$=11 min (broad) with ~20% side product at $t_R$=7 min (probably 21). Purification was by flash column chromatography eluted with [DCM:methanol:ammonia 34.5:9:1]: DCM 1:9→9:1, v/v, followed by extensive washing at 25-30 v % methanol:DCM with ammonia. The dried product fractions showed HPLC $t_R$=11-12 min and were combined, then dried to give a white/tan, waxy powder. ESI-MS $[M-H]^-$ 1105.0 m/z (expect 1105.9 m/z for $C_{62}H_{119}N_7O_9$).

[Gd].DOTA.AOC.DSA (23) gadolinium complexation was effected by suspension of 22 (25 mg) in a vigorously stirred aqueous solution (5 mL) of gadolinium (III) chloride hexahydrate (11 mg) heated at ~90° C. for 12 h under nitrogen. After settling, the excess water was removed and minimal DCM added to dissolve the lipid complex. After vigorous mixing with equal amounts of deionised water, the emulsion was separated by centrifugation and the DCM layer collected and dried in vacuo to give a white power (27 mg; 9

ESI-MS Results

Figure 15:
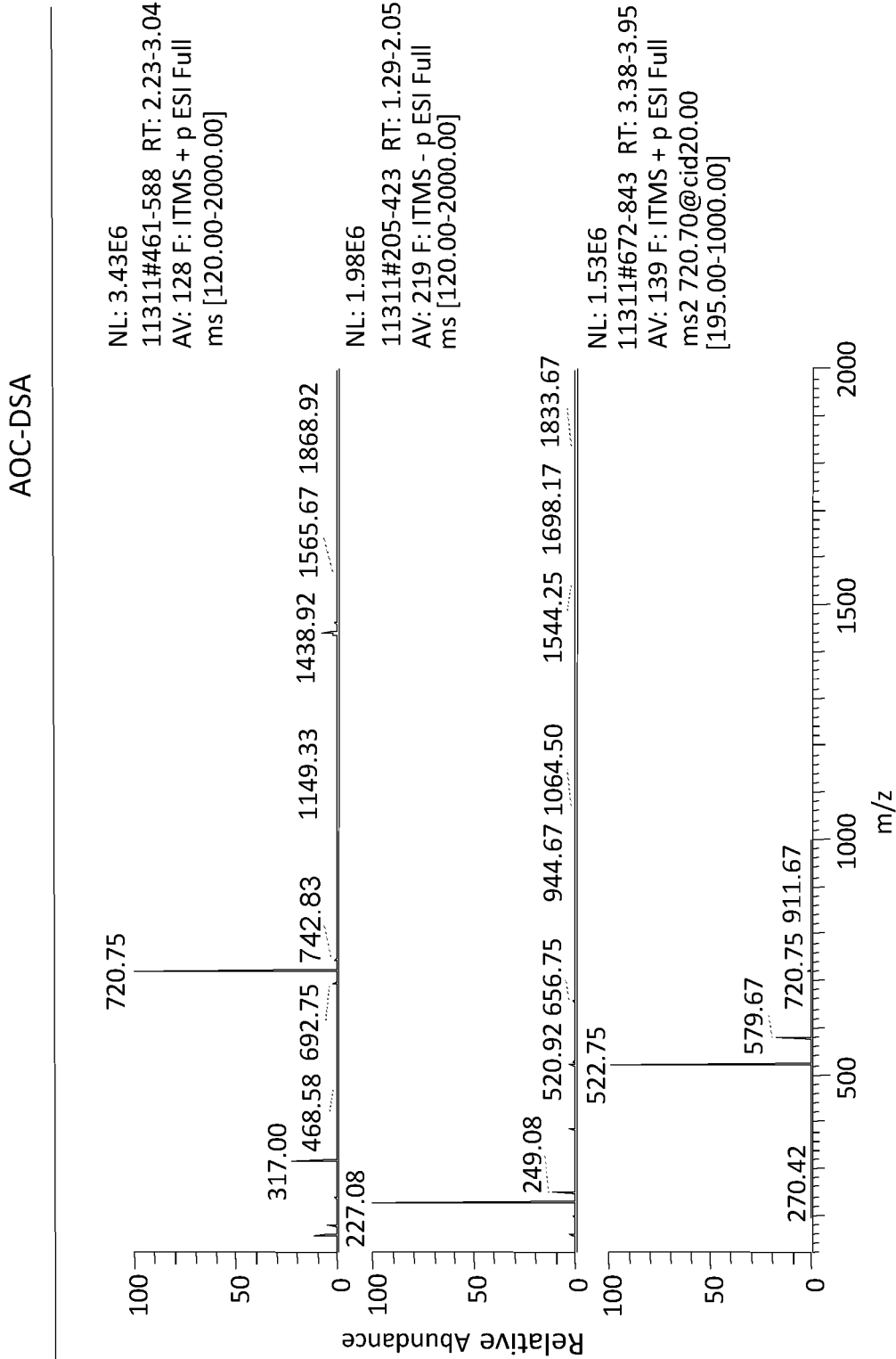
FIG. 15: ESI-MS Spectrum of AOC.DSA.

AOC.DSA: $[M+H]^+$ is 720.8 m/z (expect 720.3), while 522.8 m/z is the amine tail (expect 523.0 for $(CH_3(CH_2)_{17})_2NH_2^+$), 579.7 m/z is the DSA tail (expect 579.6 for $(CH_3(CH_2)_{17})_2NCOCH_2NH_2^+$), see FIG. 15.

DOTA.AOC.DSA: $[M-H]^-$ is 1105.0 m/z (expect 1105.7) with following +Mg, +TEA and +TFA satellites, see FIG. 16.

AHX.DSA: $[M+H]^+$ is 692.8 m/z (expect 693.2), while the tails are as AOC.DSA, see FIG. 17.

DOTA.AHX.DSA: $[M-H]^-$ is 1076.9 m/z (expect 1077.6) with following +Mg, +TEA, +TFA and perhaps +Na satellites, see FIG. 18.

Ala.Ala.DSA: $[M+H]^+$ is 721.6 m/z (expect 722.2) with a 1441.3 m/z doublet; 579.67 m/z is the DSA tail, see FIG. 19.

Figure 20:
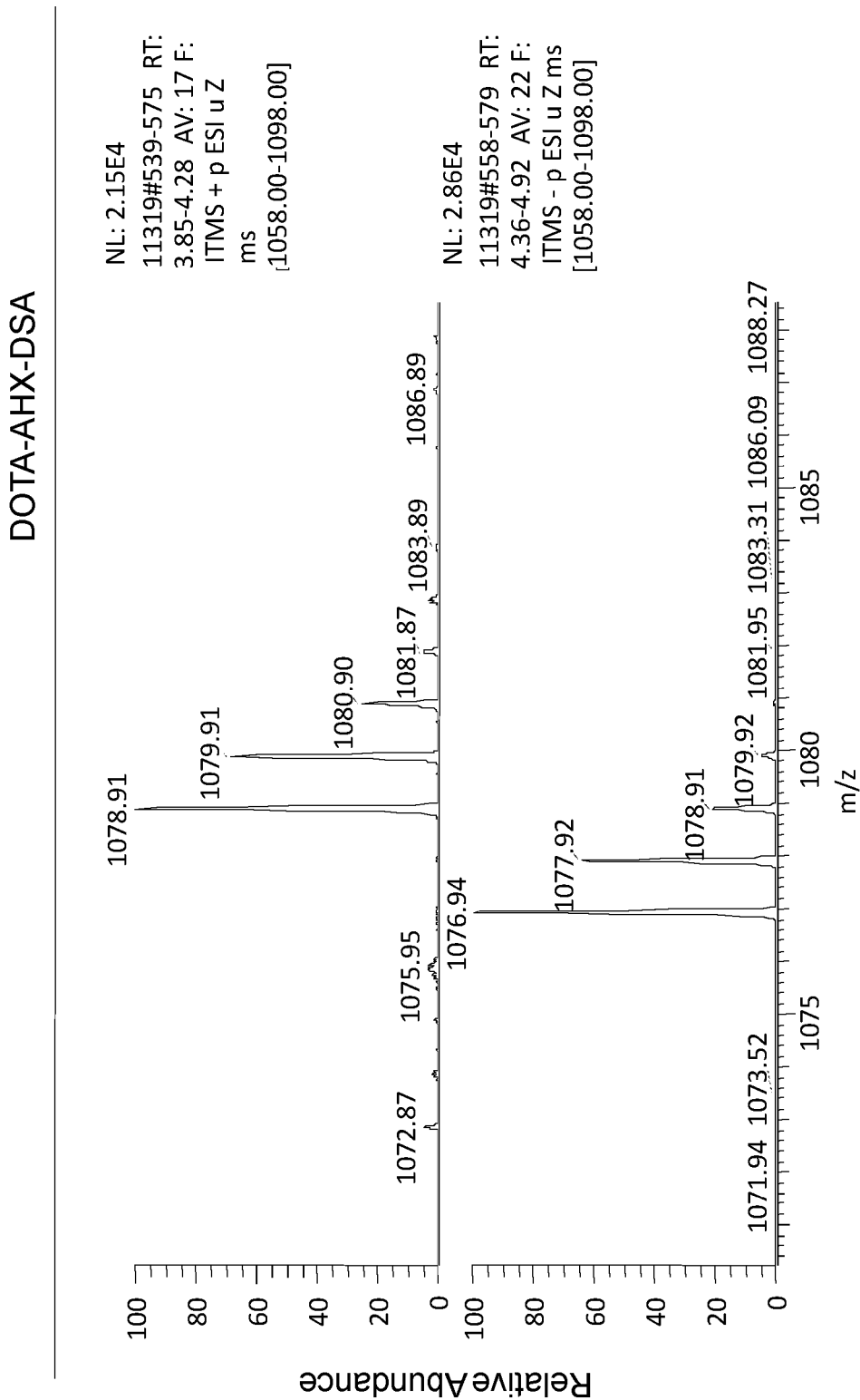
FIG. 20: ESI-MS Spectrum of DOTA.Ala.Ala.DSA.

DOTA.Ala.Ala.DSA: $[M-H]^-$ is 1105.9 m/z (expect 1106.3) with following +Mg, +TEA and +TFA satellites; fragment 1061.8 m/z is probably loss of a —COOH while 1017.9 is loss of two, see FIG. 20.

NMR Results

DSA $^1$H (400 MHz; CD$_3$Cl; 296 K) δ 3.828 (s, 2H, OCCH$_2$NH$_2$), 3.304 (t, J=7.4 Hz, 2H, OCNCH$_2$), 3.116 (t, J=7.4 Hz, 2H, OCNCH$_2$), 1.511 (m, 4H, OCNCH$_2$CH$_2$), 1.254 (s, 60H, alkyl chain CH$_2$), 0.879 (t, J=6.8 Hz, 6H, CH$_3$).

$^{13}$C (100 MHz; CD$_3$Cl; 296 K) δ 32.28 (CH$_3$CH$_2$CH$_2$), 31.33 (alkyl chain CH$_2$), 30.38 (OCNCH$_2$CH$_2$CH$_2$CH$_2$), 24.28 (CH$_3$CH$_2$).

DOTA-Ahx-DSA $^1$H (400 MHz; CD$_3$Cl; 296 K) δ 4.018 (s, 2H, OCCH$_2$NH), 3.292 (br. s, 4H, OCN(CH$_2$)$_2$), 3.140 (m, 8H, NCH$_2$COOH & NHCH$_2$CH$_2$), 3.014 (br. s, 2H, NHOCCH2N), 2.300 (v. br. s, NCH$_2$CH$_2$N?), 1.499 (m, 6H, OCN(CH$_2$CH$_2$)$_2$ & OCNHCH$_2$CH$_2$), 1.348 (m, 6H, linker alkyl chain), 1.311 (s, 60H, tail alkyl chain), 0.879 (t, J=6.8 Hz, 6H, CH$_3$).

DOTA-Aoc-DSA $^1$H (400 MHz; CD$_3$Cl; 296 K) δ 4.024 (s, 2H, OCCH$_2$NH), 3.313 (br. s, 4H, OCN(CH$_2$)$_2$), 3.144 (m, 8H, NCH$_2$COOH & NHCH$_2$CH$_2$), 2.952 (br. s, 2H, NHOCCH2N), 2.235 (v. br. s, NCH$_2$CH$_2$N?), 1.522 (m, 6H, OCN(CH$_2$CH$_2$)$_2$ & OCNHCH$_2$CH$_2$), 1.330 (m, linker alkyl chain), 1.255 (s, 60H, tail alkyl chain), 0.878 (t, J=6.8 Hz, 6H, CH$_3$).

Liposome Production

All lipids were stored in aliquots (10-20 mg/mL) in either CHCl$_3$ or MeOH/CHCl$_3$. Liposomes were prepared with the following lipid formation; [Gd]DOTA.X.DSA/DPPC/DSPC/MSPC/PEG$^{2000}$-DSPE/XL750.DSA, 30:54:5:5:6:0.05 (molar %) where X=nothing, Aoc or Ahx. Lipid stocks were combined in a round bottom flask in proportion to their respective mol % values (total mass of lipid 30-40 mg, as appropriate). The solvent was slowly evaporated in vacuo to ensure a thin and even film formation. This was hydrated in 300 mM ammonium sulphate, pH 4.0 (1 mL) and XL750.DSA freeze/thaw (×5) by alternately plunging into liquid nitrogen and then hot water to fragment the film. The resulting suspension was sonicated at 60° C. for just long enough to form a homogeneous, milky blue/white liquid. This was then extruded through a 100 nm polycarbonate membrane using a Northern Lipids (Burnaby, Canada) LIPEX extruder heated to 55° C. and pressurised to about 10-20 bar. The external buffer was exchanged to sterile 20 mM HEPES pH 7.4 with 5% glucose (w/v) using a PD10 size exclusion column (Amersham, Buckinghamshire, UK). The resulting, slightly cloudy, blue suspension was sized using a Nanoseries Nano ZS (Malvern Instruments, Worcestershire, UK) before incubation with doxorubicin hydrochloride (1.5 mg/mL aq.) at 38.0° C. for 1.5 h. This drug-loading step was performed using a Thermocycler (Mastercycler Personal, Eppendorf, Stevenage, UK) in order to provide accurate temperature control. Excess, non-encapsulated drug was removed using a PD10 column loaded with HEPES buffer, giving a cloudy deep red suspension. Liposome production was been carried out using [Gd]DOTA.Ahx.DSA and [Gd]DOTA.Aoc.DSA in direct comparison to the [Gd]DOTA.DSA formulation. In both cases, liposome formation and extrusion were more difficult and required higher temperatures and pressures. Sizing was a little large (Aoc: Zavg 158 nm diameter, PDI 0.36; Ahx: Zavg 160 nm diameter, PDI 0.367) suggesting that that production conditions need to be optimised for these new lipids. Colloidal stability on storage at 4° C. was good. Doxorubicin loading for [Gd]DOTA.Ahx.DSA liposomes was ~30% normal and [Gd]DOTA.Aoc.DSA was ~50%. It is expected that the thermosensivity $T_m$ will have been modified by the addition of the linker and hence loading conditions will need to be reoptimised.

7T MRI and ICP-MS

A series of MRI T1/T2 assessment studies have been carried out using a 7 T pre clinical MRI scanner, with the assistance of Dr Po-Wah So (James Black Centre, KCL). The focus here has been to derive reliable r1/r2 relaxivities per molar Gd(III) for liposome produced using the [Gd]DOTA.DSA, [Gd]DOTA.Ahx.DSA and [Gd]DOTA.Aoc.DSA. This is reliant on both accurate measurements of the T1/T2 effects and also the exact gadolinium concentration in the prepared liposome suspensions. The extrusion and gel filtration processes make this latter hard to estimate, so Inductively Coupled Plasma Mass Spectrometry (ICP-MS) quantification is being assessed. This is turn required testing of suitable acid digestion conditions since the lipid-chelates may not be analysed directly. For both MRI and ICP-MS, commercial Gadovist is being used a positive control contrast agent of known Gd content. Assessment of temperature, buffer salt and liposome size effects on T1/T2 are also underway.

Figure 21:
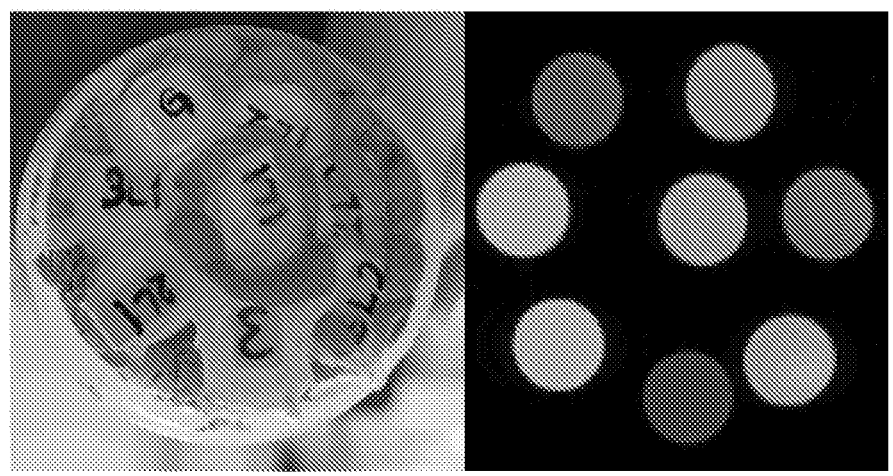
FIG. 21—Buffer, Gadovist and liposome samples contained in vials (left) and MRI with T1 weighting (right)

FIG. 21 shows Buffer, Gadovist and liposome samples contained in vials (left) and MRI with T1 weighting (right).

Figure 22B:
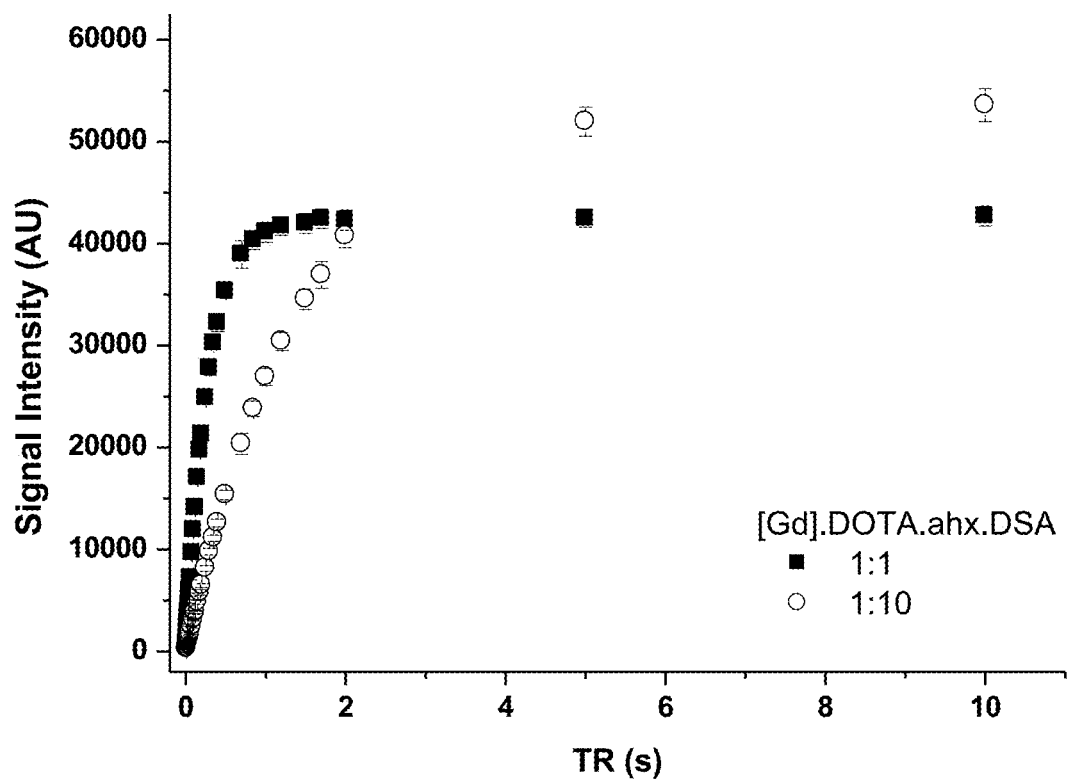
Figure 22B:
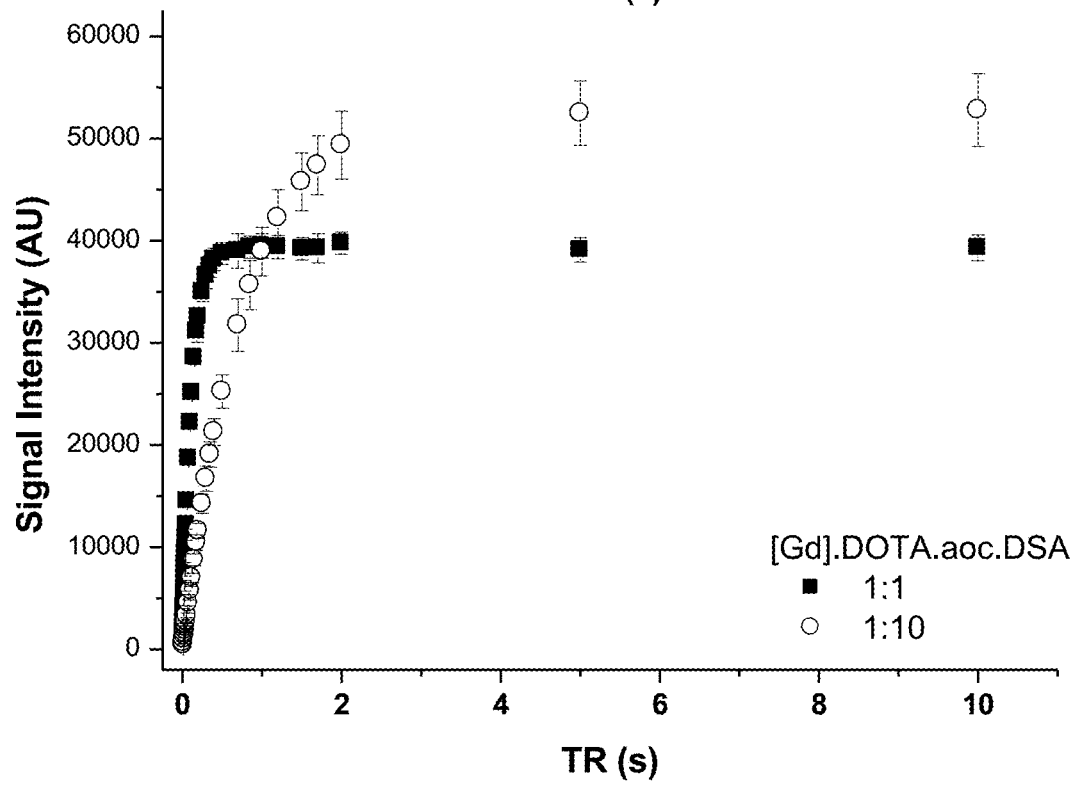
Figure 23A:
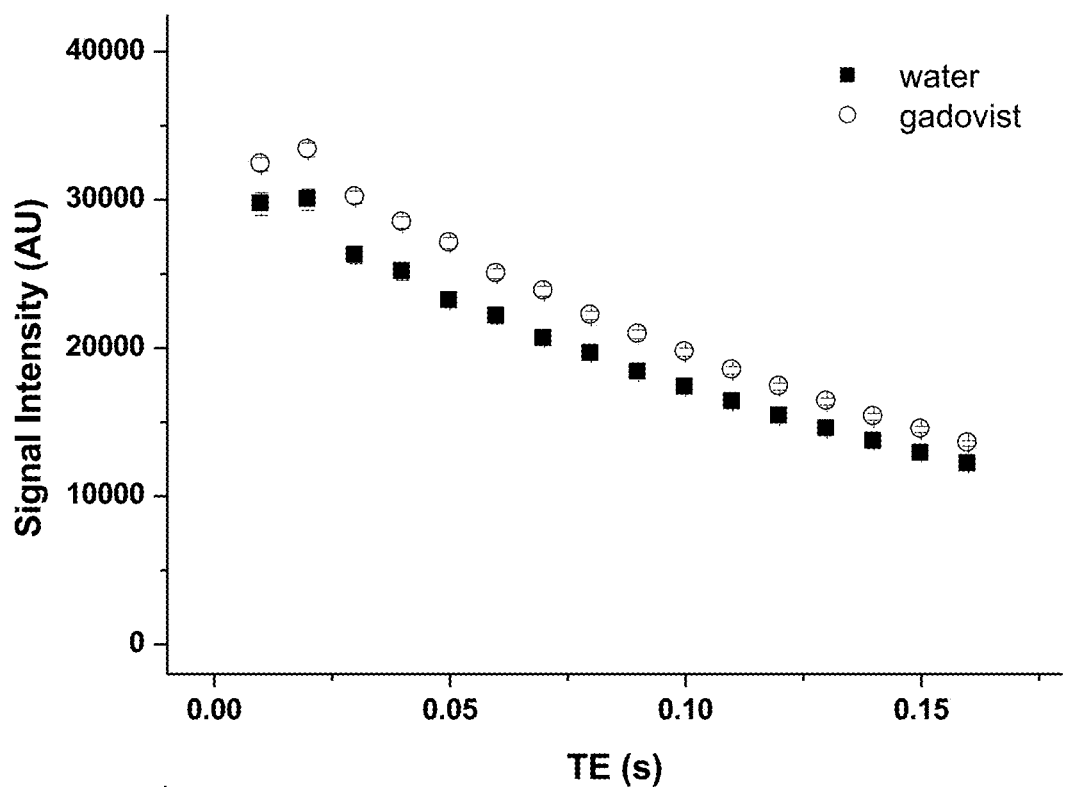
Figure 23A:
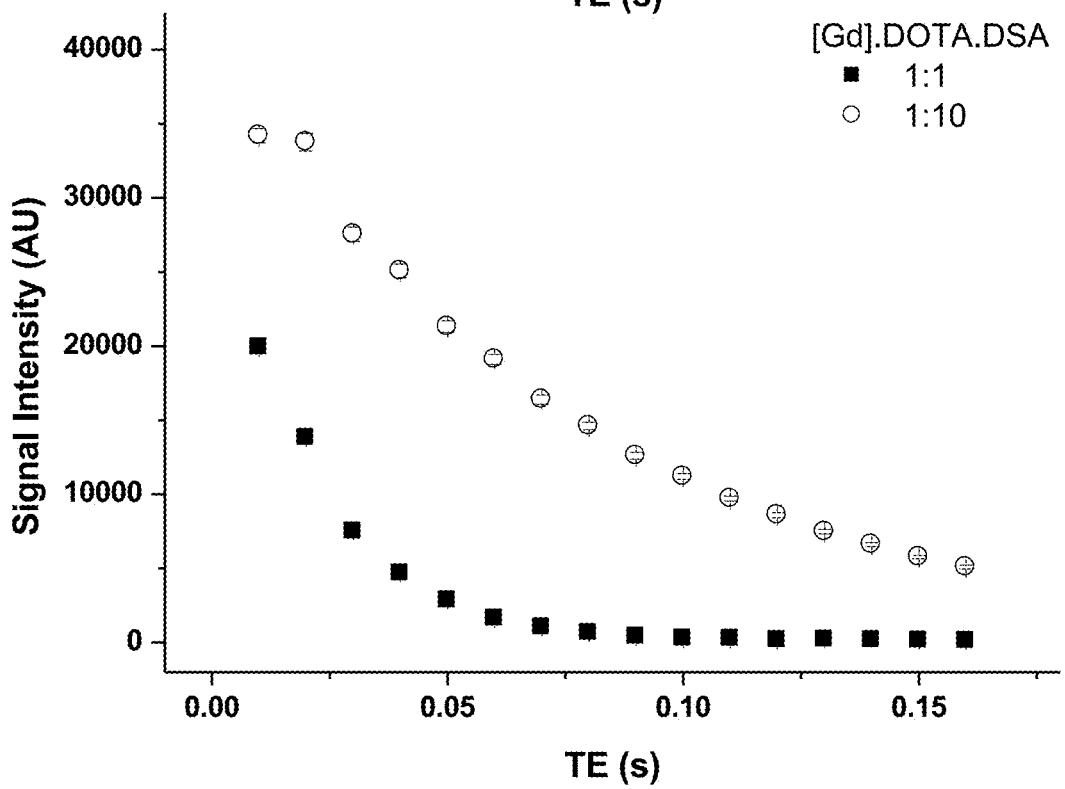
Figure 23B:
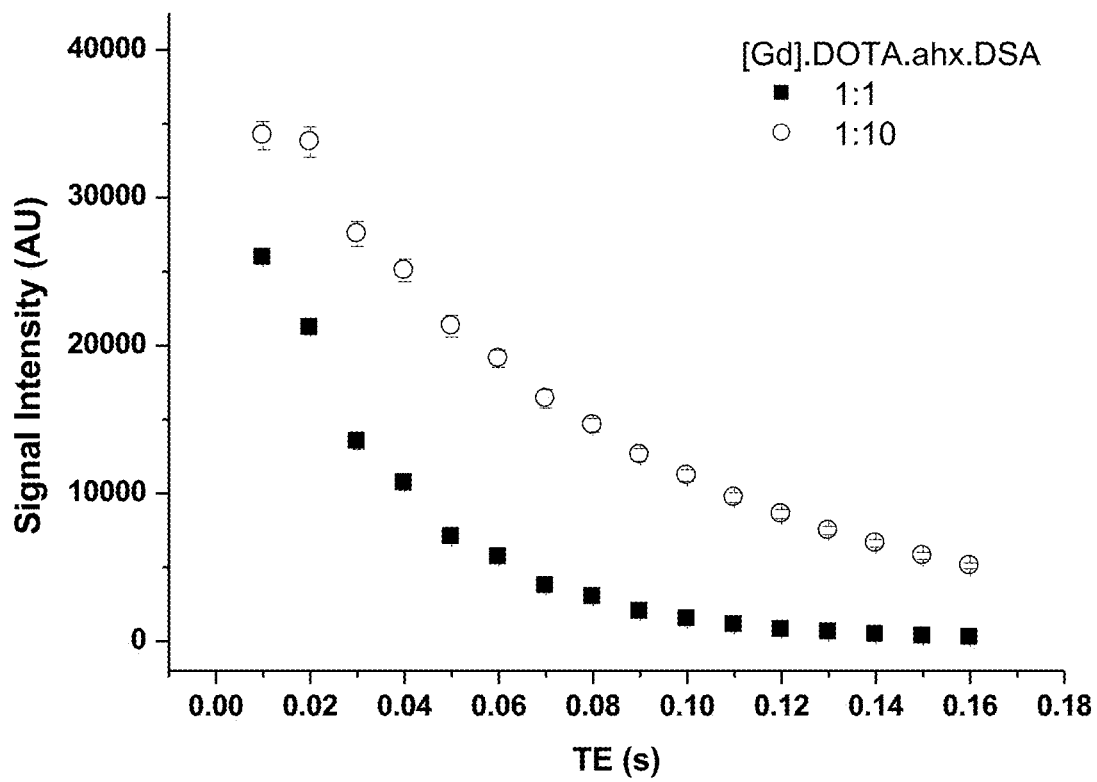
Figure 23B:
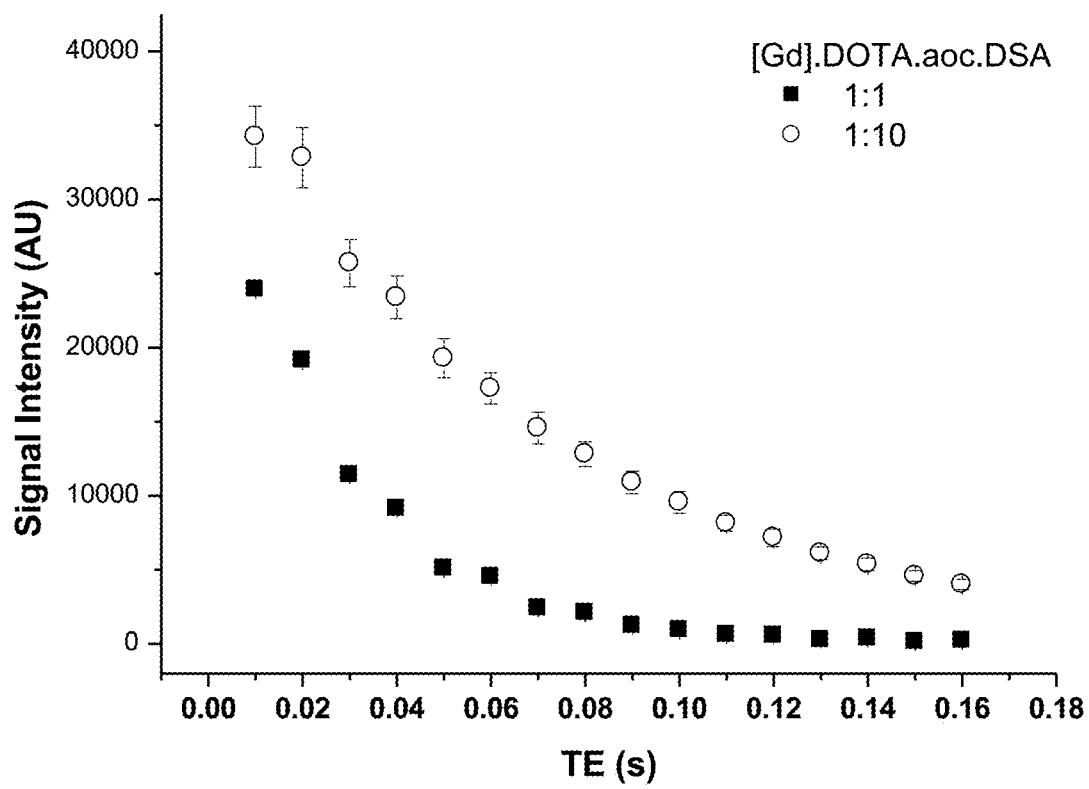
Figure 24:
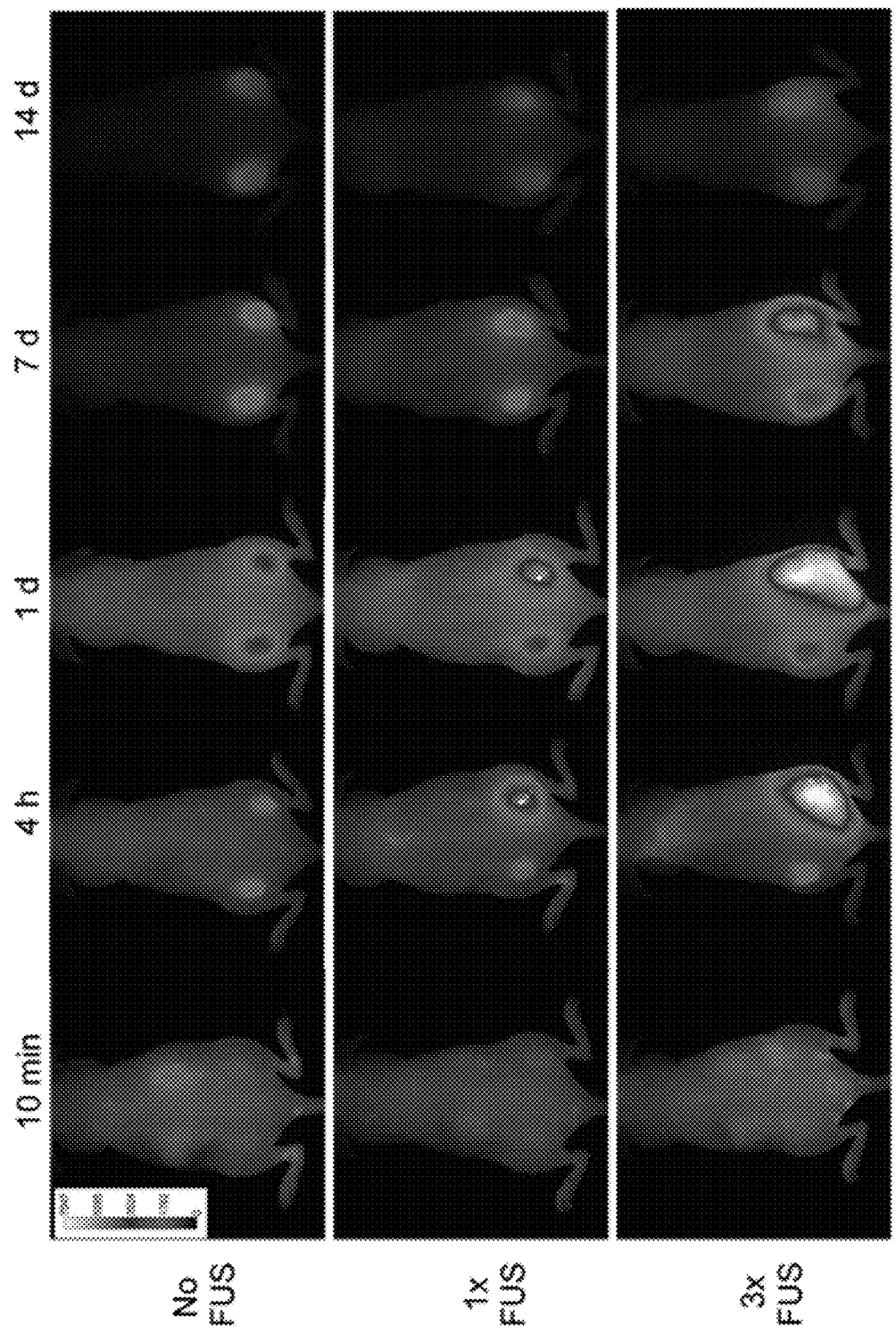
FIG. 24: NIRF in vivo imaging of mice with bilateral implanted tumours (IGROV-1) at time point post-injection of X1750-herceptin (~8 mg/kg). FUS induced hypothermia treatment was either omitted (top) or applied at 1 h (middle) or 1 h, 2 h, and 3 h 30 (bottom) on the right tumour. The difference in labelled antibody uptake is clear and lasts for more than a week.
Figure 25:
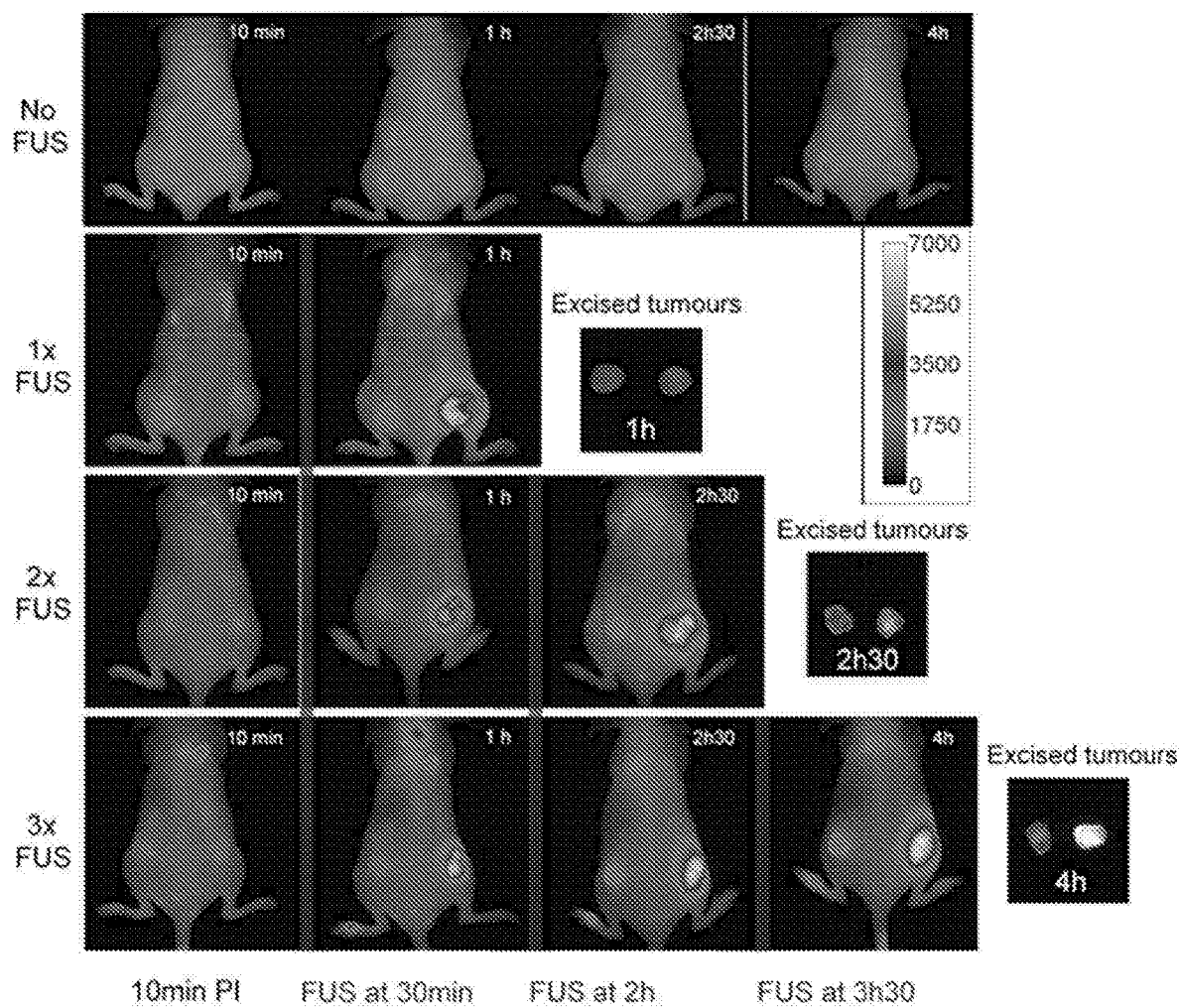
FIG. 25: Comparisons of in vivo and excised IGROV-1 tumours labeled XL750-herceptin NIRF from mice treated with no, 1, 2, or 3 rounds of FUS hyperthermia to the right hand tumour. The animals were sacrificed at 1 h, 2 h 30 min, and 4 h post injection.
Figure 26:
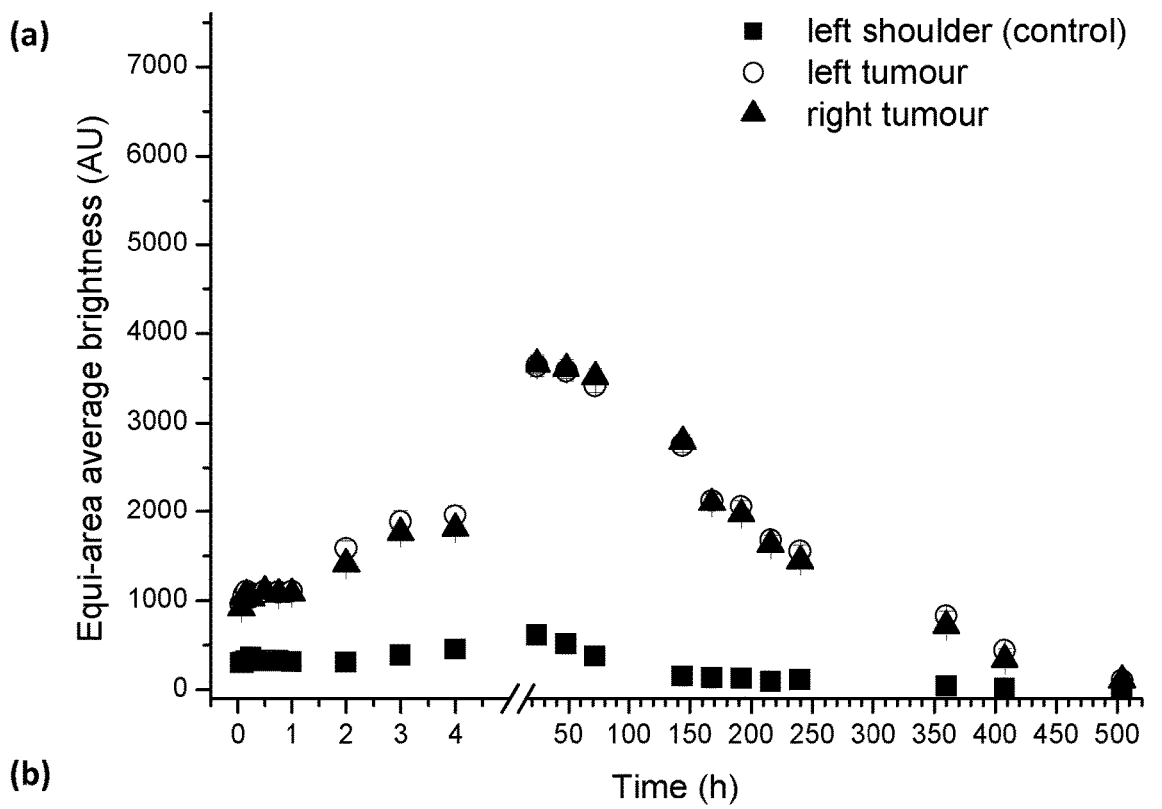
FIG. 26: Assessed brightness from area matched regions of left and right hand tumours, compared to a muscle control for mice undergoing either (a) no FUS treatment; (b) 1 round of FUS treatment at 30 min or (c) 3 rounds of FUS treatment at 30 min, 2 h, and 3 h 30; all post injection of XL750-herceptin (~8 mg/kg). (d) is an example of the areas of interest selected. (n=3 animals+/−S.D.)
Figure 26:
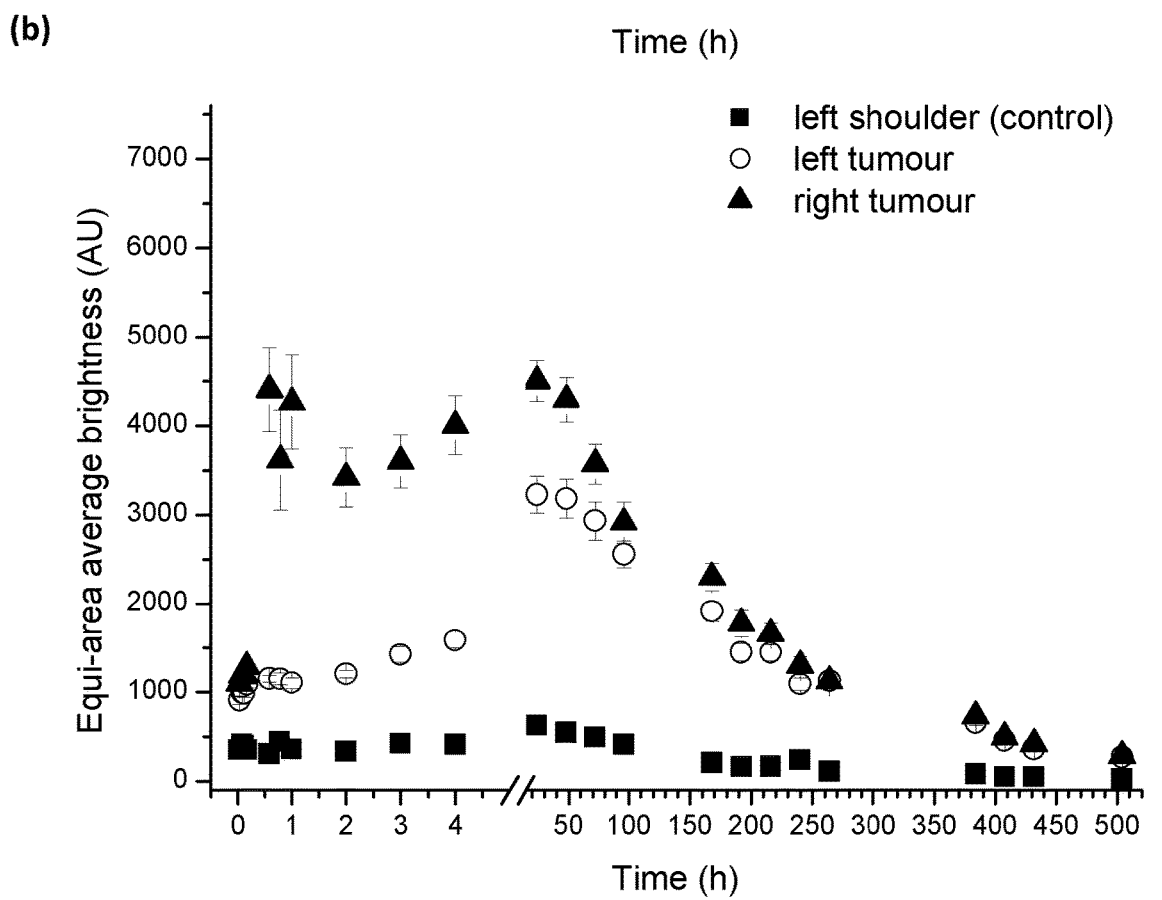
Figure 26:
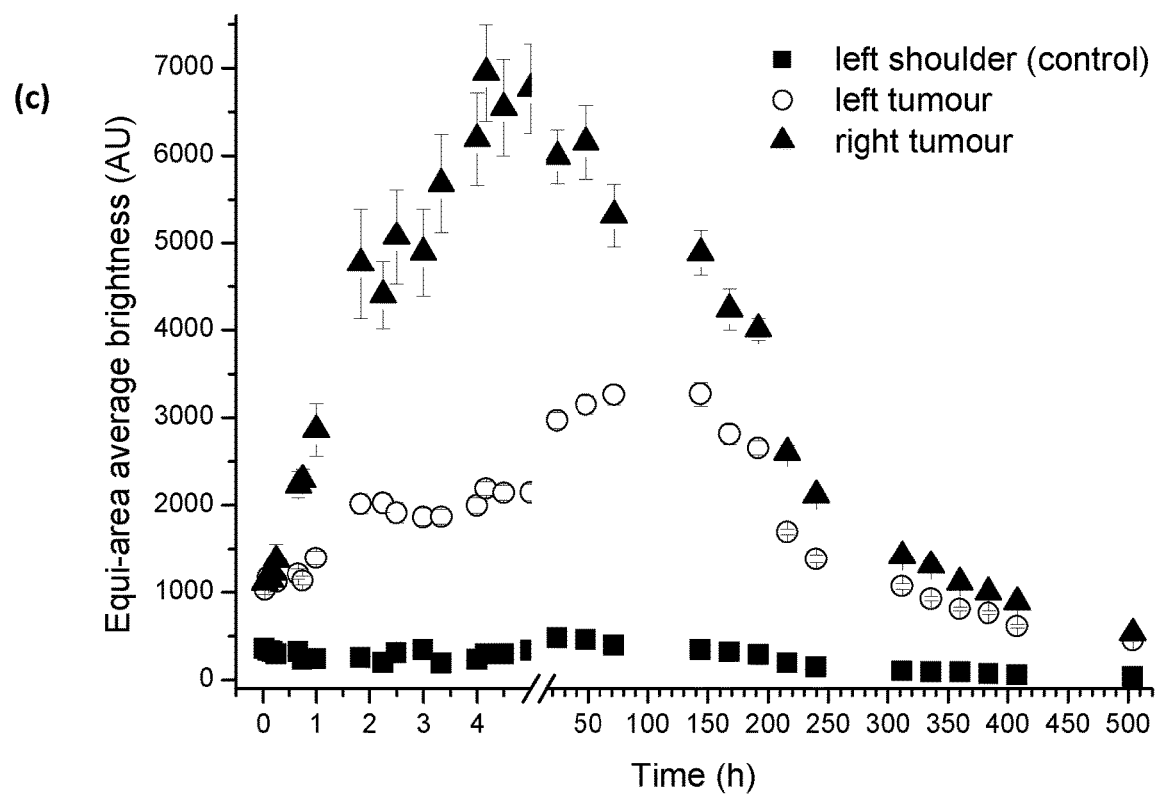
Figure 26:
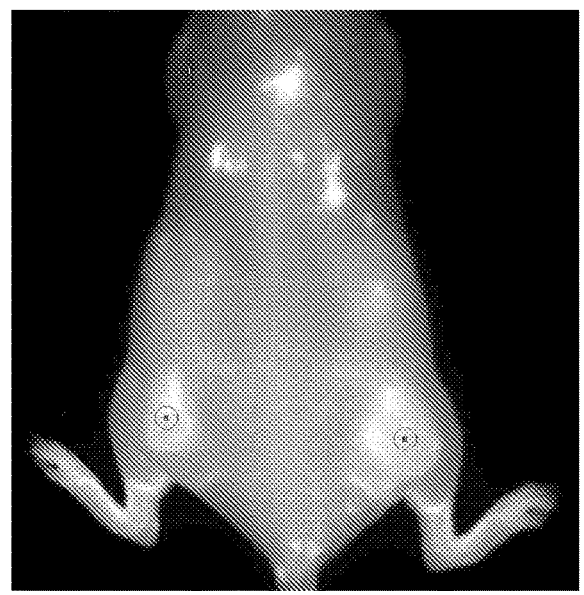
Figure 27:
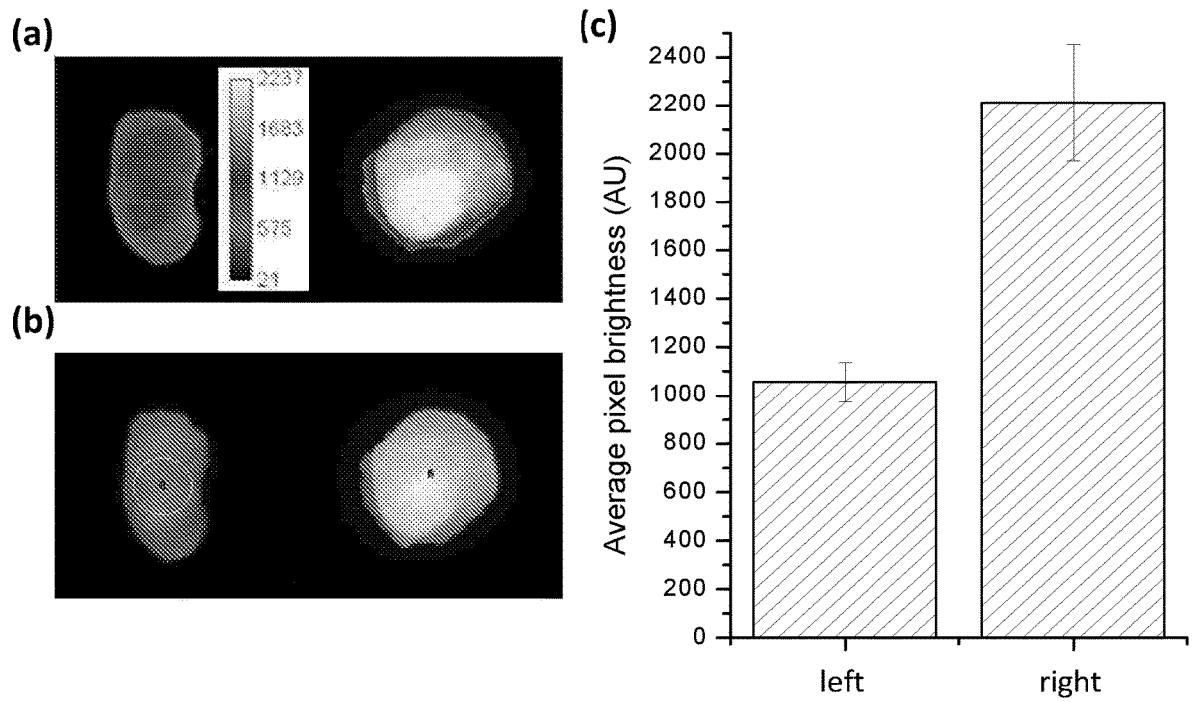
FIG. 27: NIRF imaging of representative left (no FUS) and right (3× FUS) sacrificed 5 h post injection of X1750-herceptin. (a) false colour and (b) greyscale images taken from the excised tumours, with the latter showing the matched area regions used to calculate (c) mean and 1 SD pixel brightness (n=3).
Figure 28:
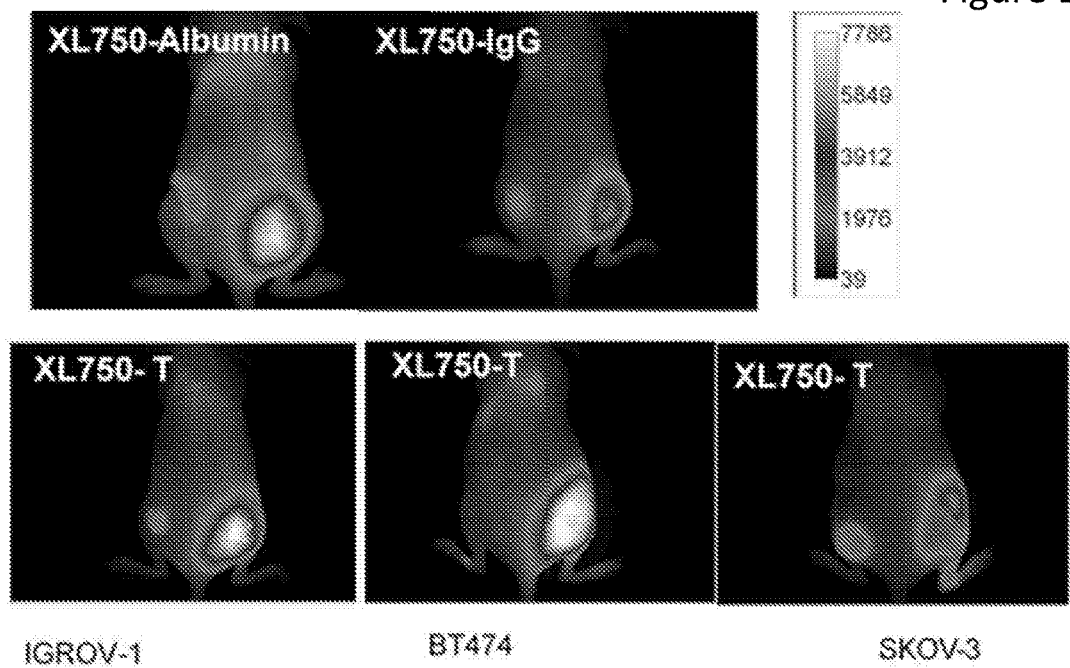
FIG. 28: Upper panel: Uptake of XL750-Albumin and XL750-IgG in IGROV-1 tumours after 3× FUS treatments. Lower Panel Comparison 3× FUS treatments on XL750-trastuzumab (XL750-T) uptake into IGROV-1, SKOV-3 and BT474 cell line tumours. NIRF in vivo imaging of mice at t=4 h post-injection of X1750-herceptin (~8 mg/kg). FUS induced hypothermia treatment was carried out at 1 h, 2 h, and 3 h30.

FIGS. 22 and 23 show Example T1 and T2 brightness traces for controls and liposome samples. Curve fitting from this data to gives the T1 or T2 values for these samples.

Sample digestion was by heating 100 µL of sample with con. $HNO_3$ (200 µL) and $H_2O_2$ (30%, 110 µL) overnight at 95° C. in sealed vial. These samples were then diluted to 2.5 mL with RO water for storage and further diluted 10-100 fold before ICP-MS analysis. Lipid digestion via this approach appears to be complete but quantified Gd concentrations from both controls and liposome samples remains somewhat higher than expected, suggesting a calibration issue. This is being investigated.

MRI data (T1, T2 lower is brighter) is shown Table 1:

Summary of Relaxometry Values

Comparison of liposomes containing different lipids as measured at 7T Magnet*.

| Sample | $r_1$ ($mM^{-1}ms^{-1}$) |
|---|---|
| GdDOTA. DSA Liposomes | 4.7 |
| Gd DOTA. Ahx. DSA Liposomes | 10.5 |
| Gd DOTA. Aoc. DSA Liposomes | 12.1 |
| Gadovist | 4.8 |

*Assessment of liposomes in 3T magnet provided similar differences.

All publications mentioned in the above specification are herein incorporated by reference. Various modifications and variations of the described methods and systems of the

| | Temp | | conc | | | T1 (s) | | | T2 (s) | | |
|---|---|---|---|---|---|---|---|---|---|---|---|
| | ° C. | Sample | mM | mg/mL | dil | Image J | 1 param | 3 param | Image J | 1 param | 3 param |
| G | 19.6 | Gadovist | 3.1 | | 1 | 0.084 | 0.072 | 0.084 | 0.042 | 0.0431 | 0.0422 |
| G | 19.6 | Gadovist | 3.1 | | 1 | 0.084 | 0.072 | 0.084 | 0.042 | 0.0426 | 0.0419 |
| L1 | 19.6 | F5 normal dox | | 20 | 1 | 0.158 | 0.144 | 0.158 | 0.026 | 0.0267 | 0.026 |
| L2 | 19.6 | F5 normal dox | | 20 | 10 | 0.954 | 0.93 | 0.954 | 0.067 | 0.071 | 0.0002 |
| L2 | 19.6 | F5 normal dox | | 20 | 10 | 0.987 | 0.957 | 0.987 | 0.068 | 0.0742 | 0.0002 |
| L3 | 19.6 | F5 normal dox | | 20 | 50 | 1.929 | 1.89 | 1.929 | 0.08 | 0.0852 | 0.0001 |
| L4 | 19.6 | F5 normal dox | | 20 | 100 | 2.152 | 2.114 | 2.152 | 0.084 | 0.0931 | 0.0001 |
| HL1 | 19.6 | heated, F5 normal dox | | 20 | 1 | 0.15 | 0.151 | 0.15 | 0.025 | 0.0255 | 0.0252 |
| HL2 | 19.6 | heated, F5 normal dox | | 20 | 10 | 0.902 | 0.879 | 0.902 | 0.064 | 0.0621 | 0.0002 |
| HL3 | 19.6 | heated, F5 normal dox | | 20 | 50 | 1.893 | 1.861 | 1.893 | 0.074 | 0.0679 | 0.0002 |
| HL4 | 19.6 | heated, F5 normal dox | | 20 | 100 | 2.275 | 2.229 | 2.273 | 0.082 | 0.0883 | 0.0001 |
| HL4 | 19.6 | heated, F5 normal dox | | 20 | 100 | 2.313 | 2.265 | 2.312 | 0.083 | 0.0908 | 0.0001 |
| W | 19.6 | RO water | | | | 2.747 | 2.696 | 2.746 | 0.1 | 0.265 | nc |
| W | 19.6 | RO water | | | | 2.806 | 2.755 | 2.805 | 0.1 | 0.2679 | nc |
| H | 19.6 | 20 mM HEPES, 5 w % glucose, pH 7.4 | 20 | | | 2.704 | 2.622 | 2.704 | 0.084 | 0.0897 | 0.0001 |
| W | 19.6 | RO water | | | | 2.884 | 2.861 | 2.883 | 0.1 | 0.139 | nc |
| W | 35.5 | RO water | | | | 4.237 | 4.211 | 4.248 | 0.1 | 0.1071 | nc |
| G | 19.6 | Gadovist | >0.3 | | | 2.061 | 2.033 | 2.061 | 0.1 | 0.206 | nc |
| G | 35.5 | Gadovist | >0.3 | | | 2.606 | 2.602 | 2.617 | 0.1 | 0.153 | nc |
| F5 | 19.6 | F5 normal nodox | | 20 | 1 | 0.15 | 0.1348 | 0.1502 | 0.021 | 0.021 | 0.021 |
| F5 | 35.5 | F5 normal nodox | | 20 | 1 | 0.124 | 0.1247 | 0.1403 | 0.018 | 0.018 | 0.018 |
| F5.2 | 19.6 | F5 normal nodox | | 20 | 10 | 0.897 | 0.8702 | 0.897 | 0.066 | 0.083 | nc |
| F5.2 | 35.5 | F5 normal nodox | | 20 | 10 | 0.931 | 0.9241 | 0.9429 | 0.045 | 0.047 | 0.045 |
| ahx | 19.6 | F5 [Gd].DOTA.ahx.DSA | | 20 | 1 | 0.294 | 0.2758 | 0.2936 | 0.032 | 0.032 | 0.032 |
| ahx | 35.5 | F5 [Gd].DOTA.ahx.DSA | | 20 | 1 | 0.264 | 0.2609 | 0.2804 | 0.029 | 0.029 | 0.029 |
| ahx.2 | 19.6 | F5 [Gd].DOTA.ahx.DSA | | 20 | 10 | 1.471 | 1.44 | 1.471 | 0.077 | 0.083 | nc |
| ahx.2 | 35.5 | F5 [Gd].DOTA.ahx.DSA | | 20 | 10 | 1.643 | 1.622 | 1.652 | 0.052 | 0.054 | 0.054 |
| aoc | 19.6 | F5 [Gd].DOTA.aoc.DSA | | 20 | 1 | 0.126 | 0.111 | 0.1261 | 0.028 | 0.029 | 0.028 |
| aoc | 35.5 | F5 [Gd].DOTA.aoc.DSA | | 20 | 1 | 0.109 | 0.1086 | 0.1241 | 0.023 | 0.023 | 0.023 |
| aoc.2 | 19.6 | F5 [Gd].DOTA.aoc.DSA | | 20 | 10 | 0.784 | 0.7556 | 0.7837 | 0.068 | 0.069 | 0.068 |
| aoc.2 | 35.5 | F5 [Gd].DOTA.aoc.DSA | | 20 | 10 | 0.825 | 0.812 | 0.8378 | 0.041 | 0.041 | 0.041 |
| W | | RO water | | | | 2.686 | 2.686 | 2.666 | 0.1 | nc | 0.1378 |
| A2 | 19.6 | Gadovist | 3 | | 1 | 0.092 | 0.09174 | 0.07712 | 0.047 | 0.04691 | 0.0488 |
| B1 | 19.6 | [Gd].DOTA.DSA | 6.2 | 20 | 1 | 0.065 | 0.06472 | 0.0536 | 0.009 | 0.008877 | 0.008501 |
| B2 | 19.6 | [Gd].DOTA.DSA | 6.2 | 20 | 10 | 0.515 | 0.5148 | 0.4935 | 0.044 | 0.04448 | 0.04591 |
| C1 | 19.6 | [Gd].DOTA.ahx.DSA | 6.2 | 20 | 1 | 0.015 | 0.0152 | 0.01052 | 0.019 | 0.01816 | 0.00777 |
| C2 | 19.6 | [Gd].DOTA.ahx.DSA | 6.2 | 20 | 10 | 0.157 | 0.1575 | 0.1428 | 0.031 | 0.03118 | 0.03141 |
| D1 | 19.6 | [Gd].DOTA.aoc.DSA | 6.2 | 20 | 1 | 0.018 | 0.01818 | 0.01264 | 0.007 | 0.00727 | 0.006916 |
| D2 | 19.6 | [Gd].DOTA.aoc.DSA | 6.2 | 20 | 10 | 0.184 | 0.184 | 0.1704 | 0.038 | 0.03768 | 0.03885 |
| W | 39.5 | RO water | | | | 4.522 | 4.507 | 4.387 | 0.1 | nc | 0.1155 |
| A1 | 39.5 | Gadovist | 3 | | 1 | 0.13 | 0.1297 | 0.1138 | 0.053 | 0.05335 | 0.05578 |
| B3 | 39.5 | [Gd].DOTA.DSA | | | 1 | 0.135 | 0.135 | 0.1195 | 0.018 | 0.01761 | 0.01755 |
| B4 | 39.5 | [Gd].DOTA.DSA | | | 10 | 0.949 | 0.948 | 0.9219 | 0.049 | 0.04938 | 0.05132 |
| D3 | 39.5 | [Gd].DOTA.ahx.DSA | | | 1 | 0.273 | 0.2729 | 0.2542 | 0.029 | 0.02933 | 0.02991 |
| D4 | 39.5 | [Gd].DOTA.ahx.DSA | | | 10 | 1.684 | 1.683 | 1.66 | 0.06 | 0.05965 | 0.06142 |
| C3 | 39.5 | [Gd].DOTA.aoc.DSA | | | 1 | 0.121 | 0.1212 | 0.1074 | 0.024 | 0.02372 | 0.02385 |
| C4 | 39.5 | [Gd].DOTA.aoc.DSA | | | 10 | 0.812 | 0.8113 | 0.7905 | 0.052 | 0.05162 | 0.05338 | invention will be apparent to those skilled in the art without departing from the scope and the spirit of the invention. Although the invention has been described in connection with specific preferred embodiments, it should not be understood that the invention as claimed should not be unduly limited to such specific embodiments. Indeed, various modifications of the described modes for carrying out the invention which are obvious to those skilled in chemistry, biology or related fields are intended to be within the scope of the following claims.

REFERENCES

1. Eberhard A, Kahlert S, Goede V, Hemmerlein B, Plate K H, Augustin H G. Heterogeneity of angiogenesis and blood vessel maturation in human tumors: implications for antiangiogenic tumor therapies. Cancer Res. 2000; 60(5): 1388-93. Epub Mar. 23, 2000.
2. Horsman M R. Tissue physiology and the response to heat. Int J Hyperthermia. 2006; 22(3):197-203. Epub Jun. 7, 2006.
3. May J P, Li S D. Hyperthermia-induced drug targeting. Expert Opin Drug Deliv. 2013; 10(4):511-27. Epub Jan. 8, 2013.
4. Hauck M L, LaRue S M, Petros W P, Poulson J M, Yu D, Spasojevic I, et al. Phase I trial of doxorubicin-containing low temperature sensitive liposomes in spontaneous canine tumors. Clin Cancer Res. 2006; 12(13):4004-10. Epub Jul. 5, 2006.
5. Needham D, Dewhirst M W. The development and testing of a new temperature-sensitive drug delivery system for the treatment of solid tumors. Adv Drug Deliv Rev. 2001; 53(3):285-305. Epub Dec. 18, 2001.
6. Poon R T, Borys N. Lyso-thermosensitive liposomal doxorubicin: an adjuvant to increase the cure rate of radiofrequency ablation in liver cancer. Future Oncol. 2011; 7(8):937-45. Epub Aug. 10, 2011.
7. Tagami et al, J Control Release. 2011; 154(3):290-7.
8. Park et al, J Control Release. 2013; 170(3):373-9.
9. Dromi S, Frenkel V, Luk A, Traughber B, Angstadt M, Bur M, et al. Pulsed-high intensity focused ultrasound and low temperature-sensitive liposomes for enhanced targeted drug delivery and antitumor effect. Clin Cancer Res. 2007; 13(9):2722-7. Epub May 3, 2007.
10. Frenkel et al, Acad. Radiol. 2006; 469-479, Delivery of Doxil in Breast cancer (investigation Tumour Model by pulsed HIFU).
11. O'Neill & Li, Int. J. Hyperthermia, September 2008, 24(6):506-520 (Augmentation of targeted delivery with pulsed HIFU).
12. Tu J, Ha Hwang J, Chen T, Fan T, Guo X, Crum L A, et al. Controllable in vivo hyperthermia effect induced by pulsed high intensity focused ultrasound with low duty cycles. Appl Phys Lett. 2012; 101(12):124102. Epub Nov. 1, 2012.
13. Ahmed N, Fessi H, Elaissari A. Theranostic applications of nanoparticles in cancer. Drug Discov Today. 2012; 17(17-18):928-34. Epub Apr. 10, 2012.
14. Janib S M, Moses A S, MacKay J A. Imaging and drug delivery using theranostic nanoparticles. Adv Drug Deliv Rev. 2010; 62(11):1052-63. Epub Aug. 17, 2010.
15. Ma X, Zhao Y, Liang X J. Theranostic nanoparticles engineered for clinic and pharmaceutics. Acc Chem Res. 2011; 44(10):1114-22. Epub Jul. 8, 2011.
16. Kenny G D, Kamaly N, Kalber T L, Brody L P, Sahuri M, Shamsaei E, et al. Novel multifunctional nanoparticle mediates siRNA tumour delivery, visualisation and therapeutic tumour reduction in vivo. J Control Release. 2011; 149(2):111-6. Epub Oct. 5, 2010.
17. Kamaly N, Kalber T, Ahmad A, Oliver M H, So P W, Herlihy A H, et al. Bimodal paramagnetic and fluorescent liposomes for cellular and tumor magnetic resonance imaging. Bioconjug Chem. 2008; 19(1):118-29. Epub Nov. 8, 2007.
18. Kamaly N, Kalber T, Kenny G, Bell J, Jorgensen M, Miller A. A novel bimodal lipidic contrast agent for cellular labelling and tumour MRI. Org Biomol Chem. 2010; 8(1): 201-11.
19. Kamaly N, Kalber T, Thanou M, Bell J D, Miller A D. Folate receptor targeted bimodal liposomes for tumor magnetic resonance imaging. Bioconjug Chem. 2009; 20(4): 648-55. Epub Apr. 17, 2009.
20. Song S, Liu D, Peng J, Deng H, Guo Y, Xu L X, et al. Novel peptide ligand directs liposomes toward EGF-R high-expressing cancer cells in vitro and in vivo. Faseb J. 2009; 23(5): 1396-404.
21. Miller A D. Lipid-based nanoparticles in cancer diagnosis and therapy. Journal of drug delivery. 2013; 2013: 165981. Epub Aug. 13, 2013.
22. Miller A D. Delivery of RNAi therapeutics: work in progress. Expert review of medical devices. 2013; 10(6): 781-811. Epub Nov. 8, 2013.
23. Kamaly N, Kalber T, Kenny G D, Thanou M, Miller A D, Bell J D, inventors; Novel liposome nanoparticles for tumour magnetic resonance imaging. 2009.
24. Lanza G M, Moonen C, Baker J R, Jr., Chang E, Cheng Z, Grodzinski P, et al. Assessing the barriers to image-guided drug delivery. Wiley Interdiscip Rev Nanomed Nanobiotechnol. 2014; 6(1):1-14. Epub Dec. 18, 2013.
25. Li L, ten Hagen T L, Hossann M, Suss R, van Rhoon G C, Eggermont A M, et al. Mild hyperthermia triggered doxorubicin release from optimized stealth thermosensitive liposomes improves intratumoral drug delivery and efficacy. J Control Release. 2013; 168(2):142-50. Epub Mar. 26, 2013.
26. Melancon M P, Elliott A M, Shetty A, Huang Q, Stafford R J, Li C. Near-infrared light modulated photothermal effect increases vascular perfusion and enhances polymeric drug delivery. J Control Release. 2011; 156(2):265-72. Epub Jul. 19, 2011.
27. Kong G, Braun R D, Dewhirst M W. Characterization of the effect of hyperthermia on nanoparticle extravasation from tumor vasculature. Cancer Res. 2001; 61(7):3027-32. Epub Apr. 18, 2001.
28. Kong G, Braun R D, Dewhirst M W. Hyperthermia enables tumor-specific nanoparticle delivery: effect of particle size. Cancer Res. 2000; 60(16):4440-5. Epub Sep. 2, 2000.
29. Patankar N A, Waterhouse D, Strutt D, Anantha M, Bally M B. Topophore C: a liposomal nanoparticle formulation of topotecan for treatment of ovarian cancer. Invest New Drugs. 2013; 31(1):46-58. Epub May 23, 2012.
30. Landon C D, Park J Y, Needham D, Dewhirst M W. Nanoscale Drug Delivery and Hyperthermia: The Materials Design and Preclinical and Clinical Testing of Low Temperature-Sensitive Liposomes Used in Combination with Mild Hyperthermia in the Treatment of Local Cancer. Open Nanomed J. 2011; 3:38-64. Epub Jan. 1, 2011.
31. Huang H, Dunne M, Lo J, Jaffray D A, Allen C. Comparison of computed tomography- and optical image-based assessment of liposome distribution. Mol Imaging. 2013; 12(3):148-60. Epub Mar. 16, 2013.
32. Suganami A, Toyota T, Okazaki S, Saito K, Miyamoto K, Akutsu Y, et al. Preparation and characterization of 33. Paoli E E, Kruse D E, Seo J W, Zhang H, Kheirolomoom A, Watson K D, et al. An optical and microPET assessment of thermally-sensitive liposome biodistribution in the Met-1 tumor model: Importance of formulation. J Control Release. 2010; 143(1):13-22. Epub Dec. 17, 2009.

34. Tardi P, Choice E, Masin D, Redelmeier T, Bally M, Madden T D. Liposomal encapsulation of topotecan enhances anticancer efficacy in murine and human xenograft models. Cancer Res. 2000; 60(13):3389-93. Epub Jul. 26, 2000.

35. Mariska de Smet et al, Journal of Controlled Release 169 (2013); 82-90, SPECT/CT Imaging of TSLs for MR-image guided delivery with HIFU.

36. Frenkel et al, Acad. Radiol. 2006; 469-479, Delivery of Doxil in Breast cancer (investigation Tumour Model by pulsed HIFU).

37. O'Neill & Li, Int. J. Hyperthermia, September 2008, 24(6):506-520 (Augmentation of targeted delivery with pulsed HIFU).

38. Novel temperature-triggered liposome with high stability: Formulation, in vitro evaluation, and in vivo study combined with high-intensity focused ultrasound (HIFU) Park, Sun Min; Kim, Min Sang; Park, Sang-Jun; Park, Eun Sung; Choi, Kyu-Sil; Kim, Young-sun; Kim, Hyun Ryoung From Journal of Controlled Release (2013), 170(3), 373-379.

39. SPECT/CT imaging of temperature-sensitive liposomes for MR-image guided drug delivery with high intensity focused ultrasound. de S met, Mariska; Langereis, Sander; van den Bosch, Sandra; Bitter, Katrin; Hijnen, Nicole M.; Heijman, Edwin; Gruell, Holger Journal of Controlled Release (2013), 169(1-2), 82-90.

40. MRI contrast variation of thermosensitive magnetoliposomes triggered by focused ultrasound: a tool for image-guided local drug delivery Lorenzato, Cyril; Cernicanu, Alexandru; Meyre, Marie-Edith; Germain, Matthieu; Pottier, Agnes; Levy, Laurent; de Senneville, Baudouin Denis; Bos, Clemens; Moonen, Chrit; Smirnov, Pierre Contrast Media & Molecular Imaging (2013), 8(2), 185-192.

41. Targeted drug delivery by high intensity focused ultrasound mediated hyperthermia combined with temperature-sensitive liposomes: Computational modelling and preliminary in vivovalidation Gasselhuber, Astrid; Dreher, Matthew R.; Partanen, Ari; Yarmolenko, Pavel S.; Woods, David; Wood, Bradford J.; Haemmerich, DieterInternational Journal of Hyperthermia (2012), 28(4), 337-348.

42. http://ferraralab.bme.ucdavis.edu/research/

43. Image-guided energy deposition for targeted drug delivery US 20110270151 A1/PCT/US2009/056264/WO2010028389A1.

44. Polymeric drug carrier for image-guided delivery EP 2229182 A2 (WO2009072079A2).

Example 3

Image guided drug delivery has gained significant attention during the last few years. Labelling nanoparticles or macromolecules and monitoring their fate in the body provides information that can be used to modulate their biodistribution and improve their pharmacokinetics. In this Example we label antibodies and monitor their distribution in the tumours post intravenous injection. Using Focused Ultrasound (FUS, a non-invasive method of hyperthermia) we increase the tumour temperature to 42° C. for a short period of time (3-5 min) and we observe an increased accumulation of labelled antibody. Repetition of focused ultrasound induced hyperthermic treatment increased still further the accumulation of the antibodies in the tumour. This treatment also augmented the accumulation of other macromolecules non-specific in the tumour, such as IgG and albumin. These effects may be used to enhance the therapeutic efficiency of antibodies.

Abbreviations: DPBS, Dulbecco's Phosphate-Buffered Saline; DMSO, dimethyl sulfoxide; EGFR, Epidermal Growth Factor receptor; FDA, U S Food and Drug Administration; FUS, Focused Ultrasound; HER-2, human epidermal growth factor receptor 2; HIFU, High Intensity Ultrasound; IgG, Immunoglobulin G antibody; MRI, Magnetic Resonance Imaging; NIRF, Near Infrared Fluorescence, PET, Positron Emission Tomography; SDS-PAGE, sodium dodecyl sulfate polyacrylamide gel electrophoresis; SHO, SCID Hairless Outbred; TIPS, Therapy and Imaging Probe System; XL750, XenoLight CF750 dye.

1. Introduction

Theranostic agents are diverse in nature, from single molecules to large complexes and nanoparticles which have the functions of diagnosis and treatment [1]. Theranostic agents are labelled with one or more probes (multimodal imaging), allowing real-time imaging of the therapeutic by a number of imaging modes such as MRI, PET, ultrasound or optical imaging [2-4]. The data derived from imaging using theranostics provide information for a) drug biodistribution, b) drug monitoring, c) interactions of the drug with receptors, d) mechanisms of action, and e) metabolism & clearance. Overall, theranostics provide information how the in vivo biodistribution and clearance of the potential therapeutic agent develop. This in turn allows adjustment of treatment parameters (e.g. dosage, timings) to best enhance the therapeutic effects [5]. Labelled antibodies are an important group of theranostics as they can provide insight on the mechanism of action [6,7]. Labelled antibodies have been suggested for detecting and treating breast cancer [8].

Focused Ultrasound mediated drug delivery has recently raised great interest [9,10]. The method is suited to enhancing the delivery of nanop articles in tumours for triggered release and targeted drug delivery [11]. It also allows for thermally sensitive liposomal drug delivery, enhancing delivery through sonoporation as well as improving drug delivery to the brain [10].

Along with chemotherapy, hyperthermia has experienced the development of techniques as safe and effective to treat certain forms of cancer [12]. In particular, the use of High Intensity Focused Ultrasound (HIFU or FUS) allows the non-invasive heating of internal tissue areas to coagulation temperatures, effectively destroying targeted tumour tissue [13,14]. Lower power settings may also be used to induce sub-lethal (normally <43° C.), highly localised hyperthermia that does not damage tissues directly. There have been a number of recent reports discussing the effects of such mild hyperthermia on blood irrigation and the enhanced uptake of therapeutic agents [15]. The combination of mild hyperthermia and thermoresponsive chemotherapy agents has also emerged as a recent development in Thermodox clinical phase III [16].

The method of focused ultrasound mediated hyperthermia drug delivery has been harnessed for other carriers or macromolecules however to a much lesser extent. In a recent study, it has been used to deliver B3 mAb antibody in axenograft murine cancer model, suggesting that this method could be developed for the delivery of radio-immunotherapy in tumours [17]. Recently cetuximab was also delivered in mice in a similar fashion, showing an improvement on anti-tumour effect [18].

Trastuzumab is a monoclonal antibody that binds to HER2/neu receptors, blocking human epidermal growth factor receptor 2 (HER-2) downstream signalling and inhibiting cancer cells proliferation. The HER2 gene encodes a transmembrane tyrosine kinase receptor that belongs to the Epidermal Growth Factor receptor (EGFR) family. This family of receptors includes four members (EGFR/HER1, HER2, HER3 and HER4) that function by stimulating growth factor signalling pathways [19, 20]. In 1998 Genentech's Herceptin® received FDA approval for the treatment of breast cancer [21]. At the same time FDA approved HercepTest (Dako, Denmark) for diagnosis of HER2 expression [21, 22]. Preclinical and clinical studies have clearly demonstrated that the combination of trastuzumab with small molecule chemotherapeutics (e.g. emtasine Kadcyla®, antibody drug conjugates) significantly prolongs the survival of patients with HER2-positive metastatic breast cancer [23]. In a very recent study lapatinib, a tyrosine kinase inhibitor in clinical development for cancer and a potent dual inhibitor of epidermal growth factor receptor was combined with Trastuzumab® showing impressive effects on the disease free survival parameter of patients that underwent the treatment [24].

Despite being a powerful therapeutic, little work has been done with Trastuzumab in the area of imaging [25]. Dual labelled fluorescence and radio-labeled Trastuzumab® has been tested to diagnose tumours in mice [26]. Labelling of Trastuzumab for MRI has been proved more challenging and more sophisticated approaches have been introduced [27].

We investigated the effect of hyperthermia on antibody biodistribution in the body. In this work, we report on the effects of FUS-induced mild hyperthermia on the uptake of Trastuzumab® to murine xenograft tumours. The localisation of the antibodies (with a covalently attached dye) was tracked using a Near Infrared Fluorescence (NIRF) imaging system.

Materials and Methods

Unless otherwise stated, Trastuzumab/Herceptin was from Genentech (San Francisco Calif., USA), XenoLight CF 750 NIRF dye and electrophoresis reagents from Perkin Elmer (Waltham Mass., USA), buffers and cell reagents from GE Healthcare (UK) while other chemicals were from Sigma Aldrich (St. Louis Mo., USA).

1.1 XL750-Trastuzumab Conjugation

Trastuzumab (0.5 mL, 21 mg/mL) was buffer exchanged using a PD-10 column to Dulbecco's phosphate buffered saline (DPBS) with pH adjusted to 8.3 with redistilled triethylamine. Antibody fractions were identified by absorbance at 280 nm. XenoLight CF 750 NHS (0.5 µmole; 'XL750') previously dissolved in anhydrous DMSO (50 µL) was then slowly added with vigorous vortexing. Then mixture was then left stirring at r.t. for 1 h before re-separating on the PD-10, run in DPBS alone. Conjugation appeared to be almost complete (>90%) with little dye retained on the column. The resulting deep blue solution was split into 200 µL portions for storage at −20° C. Estimated final concentration was 5 mg/mL antibody, 0.24 nmol/mL XL750. Absorbance bands for a diluted sample were 280 nm (0.67 AU; protein) and 750 nm (>2 AU; NIRF dye), fluorescence peaked at 785 nm on excitation at 750 nm. Samples of the labelled antibody were analysed by SDS-PAGE using 4-20% tris-glycine non-reducing gels and highlighting protein bands with silver stain (SilverQuest, Sigma Aldrich). No significant differences were seen before and after incubation for 7 min at 42° C., suggesting that the antibody should be stable to mild hyperthermia.

1.2 Cell Culture and Tumor Generation

IGROV-1 (ovarian cancer low expressing Her-2 receptor), SKOV-3 (ovarian cancer averagely expressing Her-2 receptor) and BT474 (breast cancer highly expressing Her-2 receptor) cells were routinely cultured in medium supplemented with fetal calf serum 10% v/v. When cells reached 80-90% confluence, they were harvested and prepared for implantation in mice. Post harvesting, cells were washed in saline and counted using a haemocytometer. Accordingly with the cell counting an equal volume of saline containing the cells was mixed with matrigel (Geltrex, Gibco). For the tumor generation, $5\times10^6$ cells contained in 50% matrigel mixture were inoculated subcutaneously on both flanks of 8 weeks old SHO mice (Charles River, Germany). After about 2 weeks, the formed tumours on each flank had reached an average diameter of 5-6 mm. All experiments were approved by the Home office UK. Imaging and treatments were performed in n=3 animals per group.

1.3 FUS-Induced Hyperthermia

Mice were treated with FUS-induced hyperthermia using a Therapy and Imaging Probe System (TIPS, Philips Research, Briarcliff N.Y., USA). Under isoflurane anesthesia they were placed on a warmed gel pad over an ultrasound absorbing mat. Two or three fine-wire thermocouples (T-type, 40 ga, Physitemp Instruments Inc, Cifton N.J., USA) were implanted above and below the target tumour and temperatures recorded (0.1° C., 0.1 s resolutions) during the treatment. Thereafter, the target tumour was covered by ultrasound gel and the TIPS placed at a distance of 88 mm from the skin surface of the right-side tumour. Each FUS insonation was delivered at a frequency of 1.0 MHz, 99.9% cycle duty and 12-15 W of acoustic power actively adjusted according to the attained target (42° C.) temperatures. Once this was reached, insonation was continued for 3-5 min without further temperature increase.

1.4 Near Infrared Fluorescence Imaging

The tumour bearing mice were injected intravenously with XL750-trastuzumab (200 µL of 1 mg/mL; ~8 mg/kg mouse body weight) in sterile mM HEPES pH 7.4 with 5% glucose (w/v). The injections were performed with anaesthetized mice using a syringe driver connected to a cannula inserted in the tail vein. The injection rate used was 400 µL/min. immediately post injection, each anaesthetised animal was placed into the Maestro EX (Perkin Elmer) for imaging. The MaestroEX (Perkin Elmer) settings were adjusted to Xenolight750 fluorescence: excitation filter 684-729 nm band-pass, emission filter 745 nm long-pass, and liquid crystal filter 740-950 nm in 10 nm steps. Image stacks were then collected at regular time points during the study. The resulting stacks underwent multispectral analysis compared to previously collected data for XL750-trastuzumab using the supplied software (v. 3.0.1.2). The processed grey scale images where then brightness balanced in groups and false coloured using ImageJ (v. 1.49f http://imagej.nih.gov/ij/, 1997-2015).

2. Results

The combination of a small animal FUS guided by real-time temperature measurements from implanted thermocouples allows the application of localised and repeatable hyperthermia without deviations from the target temperature (see FIG. 4). In turn, NIRF imaging allows us to monitor the resulting changes in distribution and tumour uptake of a labelled material in real-time. Other methods of preclinical imaging such as MRI and PET (SPECT/CT) suffer from significantly longer setup and image acquisition times although resolution is substantially better [28]. The TIPS/NIRF combination we designed in our study allows the imaging of drug biodistribution 1-2 minutes after insonation and repeated imaging at ~2 min intervals following, for periods of several hours because the animal is allowed to regain consciousness [29]. This gives greater confidence in the drug biodistribution behaviours that are imaged.

NIRF optical imaging is non-hazardous (no radioactivity) preclinical and enables the tracking of the NIRF signal to ~1 cm deep inside the mouse body with high sensitivity. The short depth of the signal detection can be circumvented by rotating the mouse from ventral to dorsal position to provide information of the labelled drug accumulation in the RES (reticulo-endothelial system, in particular liver and spleen) organs of the animal [30]. In our study we used NIRF imaging to detect the distribution of labelled Trastuzumab in the tumour (see supplementary video).

Figure 16:
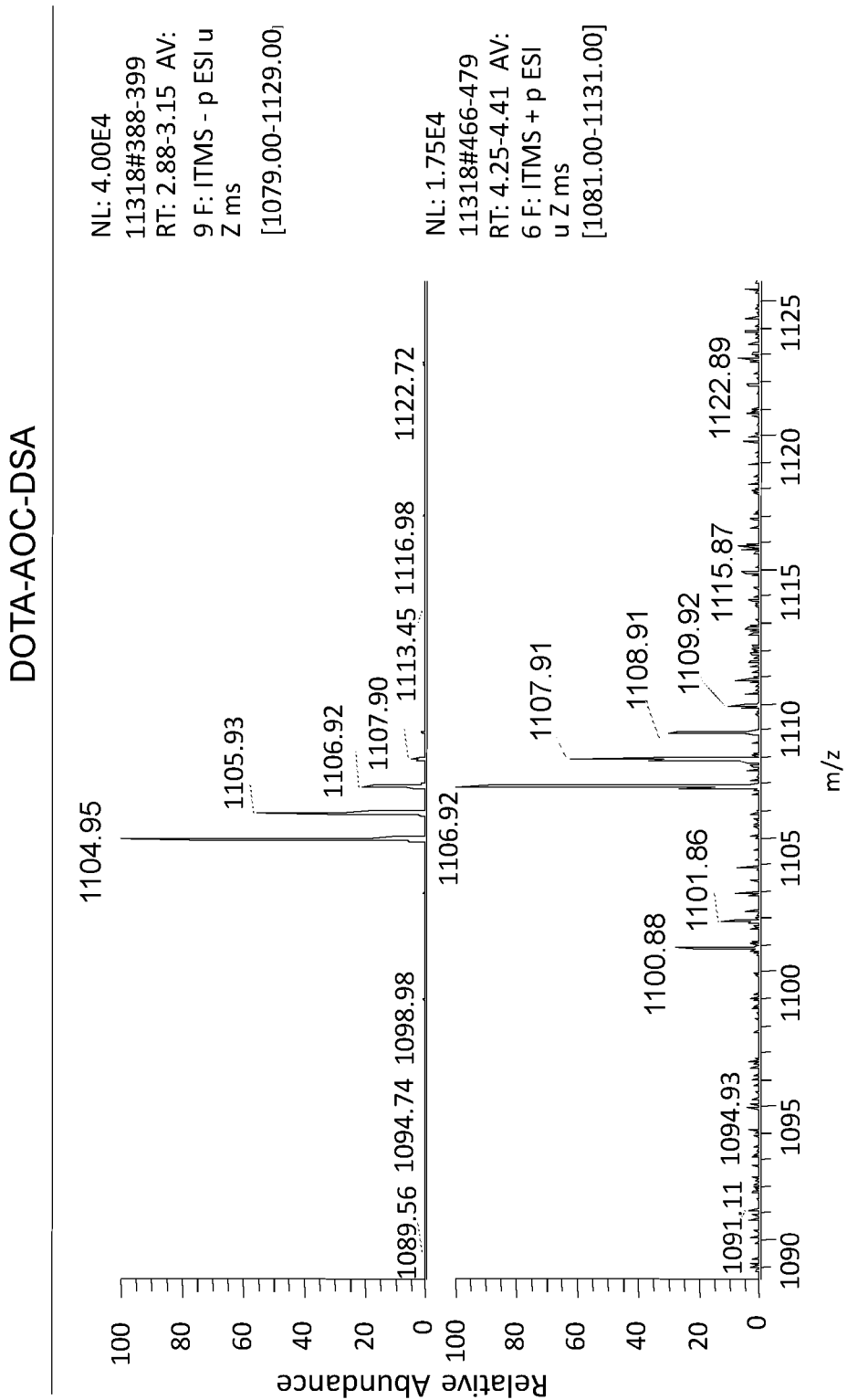
FIG. 16: ESI-MS Spectrum of DOTA.AOC.DSA.

2.1 Effect of Focused Ultrasound Treatment on Labelled Antibody Biodistribution & Tumoral Uptake Trastuzumab biodistribution was first studied without hyperthermia treatment. In FIG. 16, mice were imaged from the dorsal side showing a steady and continuous accumulation in both IGROV-1 tumours, reaching its maximum at 24-48 h (FIG. 16 upper panel) post injection. We also observed during the first hour an accumulation of the NIRF signal in the kidneys which disappeared as soon as the animal urinated. On the ventral side, fluorescence accumulated principally in the liver and the bladder over the same period, as the consequence of kidney clearance previously described.

The effects of the application of FUS-induced mild hyperthermia on tumoral uptake were then examined. The selected hyperthermia regimen was 41° C. for 5 min (this is brief compared to other Focused Ultrasound hyperthermia studies recently reviewed [31]). The change in apparent tumour uptake was noticed within 1 h, with a significant accumulation of NIRF signal in the treated by FUS area. But when the tumour was excised, only a small increase in accumulation was observed. This effect from hyperthermia application was reported by Khaibullina et al. who also described a large accumulation of the antibodies in the surrounding muscle and skin [32].

Figure 17:
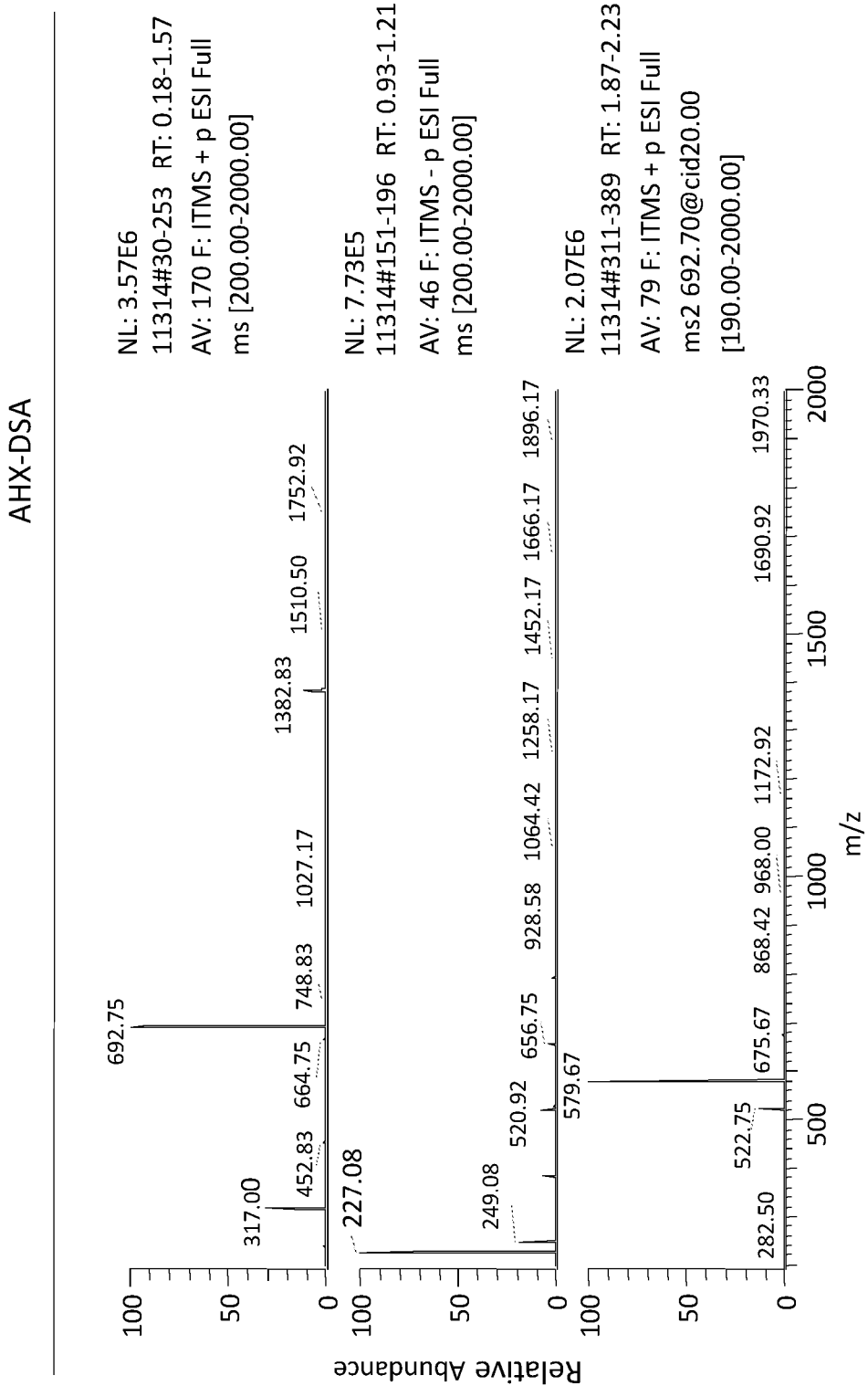
FIG. 17: ESI-MS Spectrum of AHX.DSA.

In order to improve the uptake, we repeated the FUS treatment at different time intervals post injection (see FIGS. 16 and 17). The effect of repetition of FUS induced hyperthermia led to a substantial increase in antibody accumulation in the area of the heated tumour. Excision of the tumour itself was performed at selected time points after the last application of the FUS. After excision, the heated right-hand tumours presented a substantially more NIRF signal compared to the left-hand controls (NO-FUS treatment) but only for these mice that received repetition of the Focused Ultrasound treatments (FIG. 17). This also shows that after one short treatment of hyperthermia there is an apparent increase in the fluorescent signal on the animal but a smaller increase of the concentration of Trastuzumab® in the excised tumour. This might be due to the fact that tumour excision was immediate after application of hyperthermia indicating that the signal coming from the tumour on the living animal is from the blood vessels and tissues surrounding the tumour. However the effect was evident when FUS-induced hyperthermia was repeated twice or thrice at different time points. The benefit of the use of FUS to improve the uptake of therapeutics was already demonstrated but in our study we observed a clear response in the antibody uptake upon repetition of thermal dosing that is dependent on the frequency of FUS applications.

The NIRF signal coming from the label that is attached to trastuzumab appeared to be retained in the tumours for several weeks. This might be coming from trastuzumab as the antibody has a very long half life (28 days) [33]. Whether NIRF dye stays attached to the antibodies or not distributed in the tumours remains to be investigated. It is however likely that the signal comes from the antibody-label conjugate as the small NIRF molecule clears out of the animal. We also observed that the intensity of the signal appeared to be maintained for at least 7 days (see FIGS. 16 and 18). In a recent study the biological properties of trastuzumab were not affected after the application of the effect of hyperthermia [34].

2.2 NIRF Signal Assessment in FUS Treated Tumours Versus Non Treated Tumours

Figure 18:
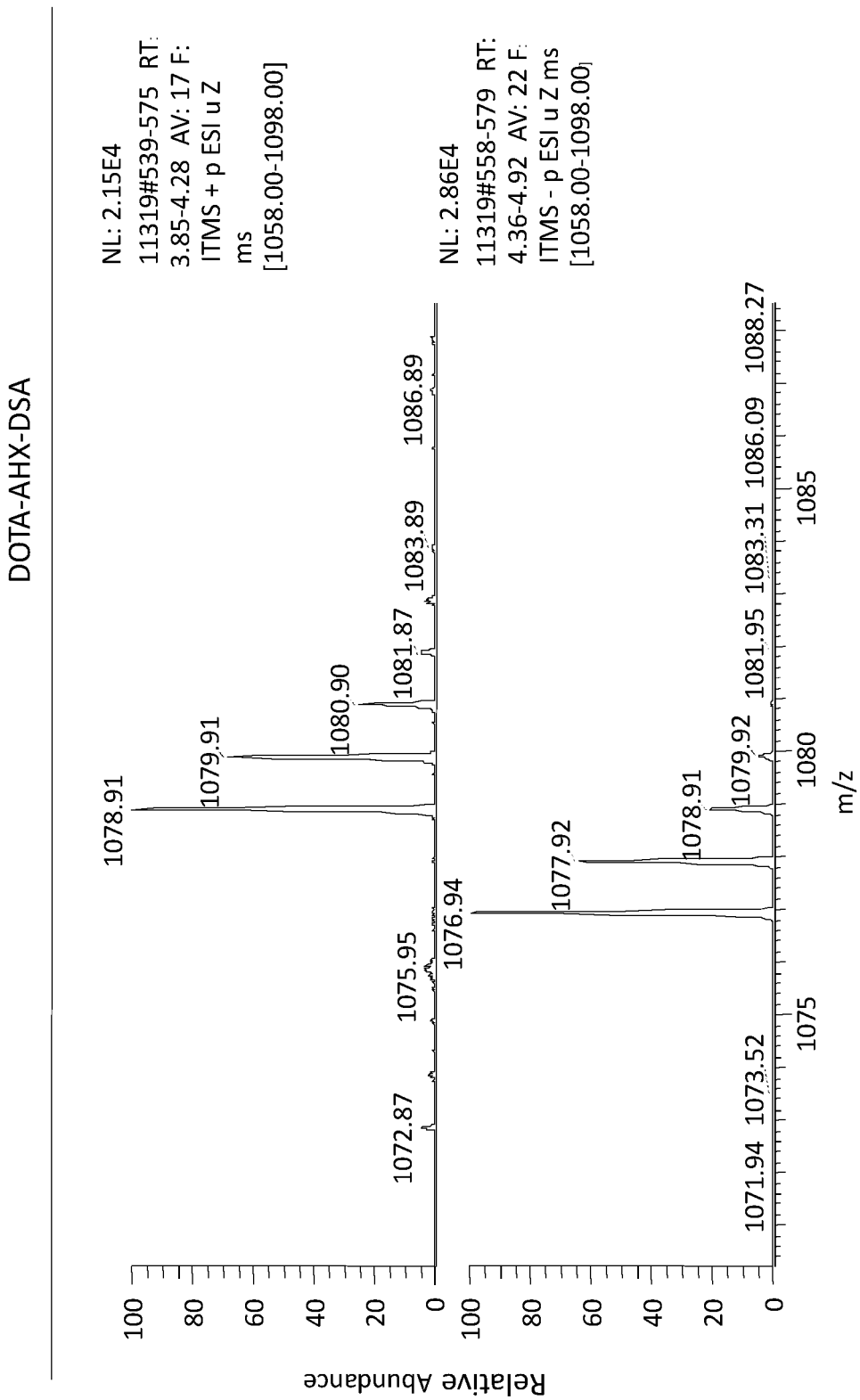
FIG. 18: ESI-MS Spectrum of DOTA.AHX.DSA.

In FIG. 18, we quantify the NIRF brightness from area matched regions (e.g. centre of the tumour) of left and right hand tumours, compared to a shoulder muscle considered as control. Conscientious of the nature of the NIRF signal and the problems that arise from its absolute quantification, we propose it here as relative way to assess the magnitude of the physiological events observed so far.

Without FUS treatment uptake appeared to be the same in both tumours, as expected. Tumours presented similar sizes and development possibly having the same vascularisation. When the fluorescent antibody was injected it was distributed to the two tumours to the same extent (FIG. 18a). After 1 round of FUS treatment the heated tumour presented clearly an increase of 2-3 fold in NIRF signal intensity. After 3 rounds of FUS treatment the gain in NIRF signal was estimated to be 3-4 fold. This method of assessment is considering the intensity of the signal and not the total phenomenon e.g. AUC of signal intensity versus time.

Figure 19:
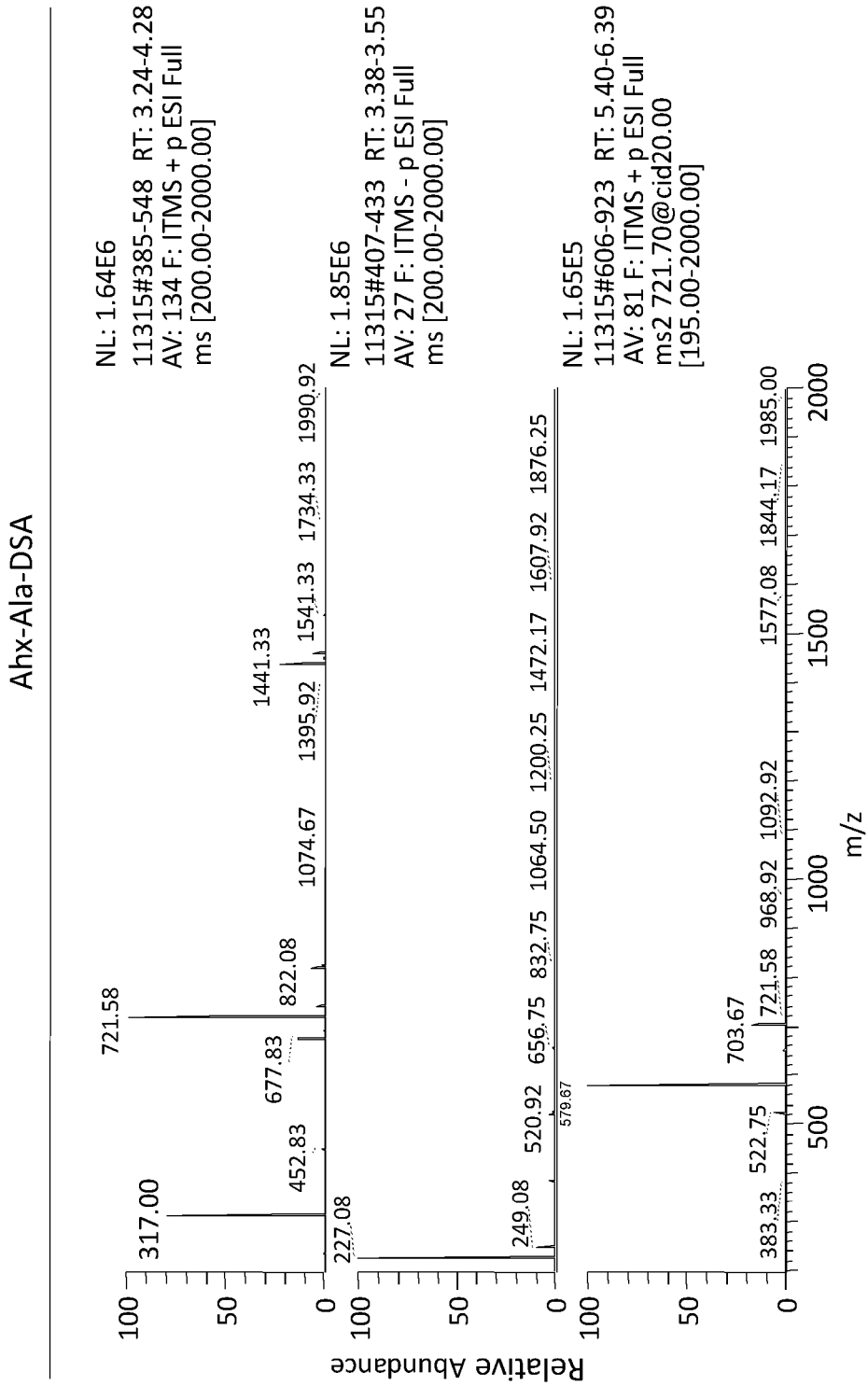
FIG. 19: ESI-MS Spectrum of Ala.Ala.DSA.

We performed the same quantification on excised tumour. These mice were sacrificed at 5 h post treatment for direct comparison of excised tumours. FIG. 19 presents the NIRF signal analysis derived from the excised tumours coming from a small matched region (e.g. centre of the tumour), indicating that for that area a 2-fold increase in NIRF-antibody signal. These results demonstrate that 3 rounds of mild hyperthermia accelerate and increase the tumoral uptake of the antibody therefore changing the pharmacokinetics of the therapy. The tumours were excised immediately after the application of the last FUS induced hyperthermia. It is possible that the enhanced vascular permeability could enhance even further the accumulation of the antibody after the last treatment.

a. Uptake Comparison Between Several Proteins and Tumour Models

In order to study the phenomenon of tumoral uptake induced by hyperthermia, two NIRF labelled non-specific proteins to the tumour: IgG and albumin, were also tested in mice bearing IGROV-1 tumours as before. Both presented similar uptake trends as the anti-Her2 antibodies in response to hyperthermia (see FIG. 20 upper panel). This result suggests that the presence of the receptor in the tumour is not the limiting factor in the rate of uptake and the enhancement due to the hyperthermia.

The effects of the 3 rounds of FUS treatment were assessed on three different tumour models expressing different levels of HER2 receptor. The selected models were SKOV-3 and BT474, ovarian and breast cancer cell lines respectively, which express higher level of HER2 receptor than IGROV-1 [35]. BT474 breast cancer cells are known for their high expression of Her-2 [36]. The level of Her-2 expression of the cancer cell lines appeared not to affect the biodistribution of the antibody in tumours after 3× FUS treatments.

The comparison between the cell lines suggest that tumoral uptake of antibodies is not restricted by the levels of HER2 receptors but to wider phenomena. The vascularisation and its permeability of the tumour may be the main obstacles to overcome in order for the molecules to penetrate the tumoral tissue. Hyperthermia increase locally the blood flow and the perfusion of the tumour and as described by Li et al. will also permeate the tumoral tissue for several hours [37].

4. Discussion

The application of mild hyperthermia offers the possibility to accelerate and increase the accumulation in the tumours of any antibody in agreement with previous study [32]. In the study presented by Khaibullina et al. and Wang et al hyperthermia was applied for 8-15 min and only once [17,32]. In our studies the repetition of mild hyperthermia induced by FUS has an additive effect on the uptake of the macromolecule by the tumour. Our results indicate that this effect is independent on the specificity of the macromolecule to a receptor overexpressed in the tumour. Imaging of the labelled antibodies Trastuzumab and IgG as well as albumin indicate that hyperthermia affects significantly their uptake by tumoral tissue. The uptake appears to be dependent on the repetitions of FUS induced treatments. In our study we performed the short treatments only thrice. As most antibodies have long half-lives these FUS treatments could be performed repeatedly during the blood circulation of the therapeutic. This methodology has definitely a clinical significance, but a better understanding and handling of the method are required to achieve improved specific tumour targeting. Despite good experimental and clinical observation on the positive effects of hyperthermia [12] more physiological studies need to be performed in order to understand what are the physiological changes and their magnitude upon the gradual raise of temperature from 37° C. to 43° C.

This methodology is compatible with different imaging modality not only with optical imaging but with MRI and PET which are widely present in clinical premises.

Nanotheranostics including antibodies have the potential to lead to a new era in treating tumours with a real time monitoring of the therapy. This may lead to a personalisation of the treatment with a better adjustment to the patient therapeutic needs. In combination with hyperthermia, it may offer a better control and optimize the treatments with an improved targeting that will reduce the dosage of administered drug. The entire procedure of image guided drug delivery has the potential to accelerate the therapy and improve the quality and efficacy of the treatment at a reduced cost. Thus, FUS-induced short duration hyperthermia applied non-invasively and locally in the tumour can increase the accumulation of macromolecular drugs such as antibodies specifically in the tumours. The effect appears to be dependent on the repetition of focused ultrasound treatments.

5. References for Example 3

1 Chen Q, Ke H, Dai Z, Liu Z. Nanoscale theranostics for physical stimulus-responsive cancer therapies. Biomaterials 2015; 73:214-230.

2 Mahajan A, Goh V, Basu S, Vaish R, Weeks A J, Thakur M H, Cook G J. Bench to bedside molecular functional imaging in translational cancer medicine: To image or to imagine? Clin Radiol 2015; 70:1060-1082.

3 Etrych T, Lucas H, Janouskova O, Chytil P, Mueller T, Mader K. Fluorescence optical imaging in anticancer drug delivery. J Control Release 2016; 226:168-181.

4 Kiessling F, Fokong S, Bzyl J, Lederle W, Palmowski M, Lammers T. Recent advances in molecular, multimodal and theranostic ultrasound imaging. Adv Drug Deliv Rev 2014; 72:15-27.

5 Kelkar S S, Reineke T M. Theranostics: Combining imaging and therapy. Bioconjug Chem 2011; 22:1879-1903.

6 Fleuren E D, Versleijen-Jonkers Y M, Heskamp S, van Herpen C M, Oyen W J, van der Graaf W T, Boerman O C. Theranostic applications of antibodies in oncology. Mol Oncol 2014; 8:799-812.

7 Weber W A, Czernin J, Phelps M E, Herschman H R. Technology insight: Novel imaging of molecular targets is an emerging area crucial to the development of targeted drugs. Nat Clin Pract Oncol 2008; 5:44-54.

8 Oude Munnink T H, Nagengast W B, Brouwers A H, Schroder C P, Hospers G A, Lub-de Hooge M N, van der Wall E, van Diest P J, de Vries E G. Molecular imaging of breast cancer. Breast 2009; 18 Suppl 3:S66-73.

9 Ebbini E S, ter Haar G. Ultrasound-guided therapeutic focused ultrasound: Current status and future directions. Int J Hyperthermia 2015; 31:77-89.

10 Thanou M, Gedroyc W. Mri-guided focused ultrasound as a new method of drug delivery. J Drug Deliv 2013; 2013:616197.

11 Lanza G M, Moonen C, Baker J R, Jr., Chang E, Cheng Z, Grodzinski P, Ferrara K, Hynynen K, Kelloff G, Lee Y E, Patri A K, Sept D, Schnitzer J E, Wood B J, Zhang M, Zheng G, Farahani K. Assessing the barriers to image-guided drug delivery. Wiley Interdiscip Rev Nanomed Nanobiotechnol 2014; 6:1-14.

12 Datta N R, Ordonez S G, Gaipl U S, Paulides M M, Crezee H, Gellermann J, Marder D, Puric E, Bodis S. Local hyperthermia combined with radiotherapy and-/or chemotherapy: Recent advances and promises for the future. Cancer Treat Rev 2015; 41:742-753.

13 Wu F. Extracorporeal high intensity focused ultrasound in the treatment of patients with solid malignancy. Minim Invasive Ther Allied Technol 2006; 15:26-35.

14 Quinn S D, Gedroyc W M. Thermal ablative treatment of uterine fibroids. Int J Hyperthermia 2015; 31:272-279.

15 May J P, Li S D. Hyperthermia-induced drug targeting. Expert Opin Drug Deliv 2013; 10:511-527.

16 Kneidl B, Peller M, Winter G, Lindner L H, Hossann M. Thermosensitive liposomal drug delivery systems: State of the art review. Int J Nanomedicine 2014; 9:4387-4398.

17 Wang S, Shin I S, Hancock H, Jang B S, Kim H S, Lee S M, Zderic V, Frenkel V, Pastan I, Paik C H, Dreher M R. Pulsed high intensity focused ultrasound increases penetration and therapeutic efficacy of monoclonal antibodies in murine xenograft tumors. J Control Release 2012; 162:218-224.

18 Miyamoto R, Oda T, Hashimoto S, Kurokawa T, Inagaki Y, Shimomura O, Ohara Y, Yamada K, Akashi Y, Enomoto T, Kishimoto M, Yanagihara H, Kita E, Ohkohchi N. Cetuximab delivery and antitumor effects are enhanced by mild hyperthermia in a xenograft mouse model of pancreatic cancer. Cancer Sci 2016; 107:514-520.

19 Yarden Y, Sliwkowski M X. Untangling the erbb signalling network. Nat Rev Mol Cell Biol 2001; 2:127-137.

20 Pinto A C, Ades F, de Azambuja E, Piccart-Gebhart M. Trastuzumab for patients with her2 positive breast cancer: Delivery, duration and combination therapies. Breast 2013; 22 Suppl 2:S152-155.

21 Nitta H, Kelly B D, Allred C, Jewell S, Banks P, Dennis E, Grogan T M. The assessment of her2 status in breast cancer: The past, the present, and the future. Pathol Int 2016

22 Cuadros M, Villegas R. Systematic review of her2 breast cancer testing. Appl Immunohistochem Mol Morphol 2009; 17:1-7.

23 de Goeij B E, Lambert J M. New developments for antibody-drug conjugate-based therapeutic approaches. Curr Opin Immunol 2016; 40:14-23.

24 Sonnenblick A, de Azambuja E, Agbor-Tarh D, Bradbury I, Campbell C, Huang Y, Dueck A C, Pritchard K I, Wolff A C, Jackisch C, Lang I, Untch M, Smith I, Boyle F, Xu B, Gomez H, Perez E A, Piccart M, Azim H A, Jr. Lapatinib-related rash and breast cancer outcome in the altto phase iii randomized trial. J Natl Cancer Inst 2016; 108

25 Stipsanelli E, Valsamaki P. Monoclonal antibodies: Old and new trends in breast cancer imaging and therapeutic approach. Hell J Nucl Med 2005; 8:103-108.

26 Cohen R, Vugts D J, Stigter-van Walsum M, Visser G W, van Dongen G A. Inert coupling of irdye800cw and zirconium-89 to monoclonal antibodies for single- or dual-mode fluorescence and pet imaging. Nat Protoc 2013; 8:1010-1018.

27 Zhu W, Okollie B, Bhujwalla Z M, Artemov D. Pamam dendrimer-based contrast agents for mr imaging of her-2/neu receptors by a three-step pretargeting approach. Magn Reson Med 2008; 59:679-685.

28 de Jong M, Essers J, van Weerden W M. Imaging preclinical tumour models: Improving translational power. Nat Rev Cancer 2014; 14:481-493.

29 Wang S, Frenkel V, Zderic V. Optimization of pulsed focused ultrasound exposures for hyperthermia applications. J Acoust Soc Am 2011; 130:599-609.

30 Zelmer A, Ward T H. Noninvasive fluorescence imaging of small animals. J Microsc 2013; 252:8-15.

31 Hijnen N, Langereis S, Grull H. Magnetic resonance guided high-intensity focused ultrasound for image-guided temperature-induced drug delivery. Adv Drug Deliv Rev 2014; 72:65-81.

32 Khaibullina A, Jang B S, Sun H, Le N, Yu S, Frenkel V, Carrasquillo J A, Pastan I, Li K C, Paik C H. Pulsed high-intensity focused ultrasound enhances uptake of radiolabeled monoclonal antibody to human epidermoid tumor in nude mice. J Nucl Med 2008; 49:295-302.

33 Leveque D, Gigou L, Bergerat J P. Clinical pharmacology of trastuzumab. Curr Clin Pharmacol 2008; 3:51-55.

34 Escoffre J M, Deckers R, Sasaki N, Bos C, Moonen C. Mild hyperthermia influence on herceptin((r)) properties. Radiol Oncol 2015; 49:41-49.

35 Bijman M N, van Berkel M P, Kok M, Janmaat M L, Boven E. Inhibition of functional her family members increases the sensitivity to docetaxel in human ovarian cancer cell lines. Anticancer Drugs 2009; 20:450-460.

36 Chakraborty A K, Mehra R, Digiovanna M P. Co-targeting er and her family receptors induces apoptosis in her2-normal or overexpressing breast cancer models. Anticancer Res 2015; 35:1243-1250.

37 Li L, ten Hagen T L, Haeri A, Soullie T, Scholten C, Seynhaeve A L, Eggermont A M, Koning G A. A novel two-step mild hyperthermia for advanced liposomal chemotherapy. J Control Release 2014; 174:202-208.

The invention claimed is:

1. A thermosensitive lipid nanoparticle comprising:
   (i) at least one phospholipid selected from the group consisting of a phosphatidylcholine, a phosphatidylethanolamine, a phosphatidylglycerol, a phosphatidylserine, a phosphatidic acid, a phosphatidylinositol, and a sphingolipid;
   (ii) at least one lysolipid selected from the group consisting of a monoacylphosphatidylcholine, a monoacylphosphatidylglycerol, a monoacylphosphatidylinositol, and a monoacylphosphatidylethanolamine;
   (iii) at least one phospholipid comprising a hydrophilic polymer,
   wherein the hydrophilic polymer comprises one or more selected from the group consisting of polyethylene glycol, polyvinylpyrolidine, polylactic acid, polyglycolic acid, copolymers of polylactic acid and polyglycolic acid, polyvinyl alcohols, polyvinylpyrrolidone, dextrans, and oligosaccharides; and
   (iv) at least one structural lipid selected from the group consisting of a gadolinium (III) 2,2',2''-(10-(2-(((2-(dioctadecylamino)-2-oxoethyl)amino)-6-oxohexyl)amino)-2-oxoethyl)-1,4,7,10-tetraazacyclododecane-1,4,7-triyl)triacetate (Gd.DOTA.AHX.DSA); or gadolinium (III) 2,2',2''(10-(2-((8-((2-(dioctadecylamino)-2-oxoethyl)amino)-8-oxooctyl)amino)-2-oxoethyl)-1,4,7,10-tetraazacyclododecane-1,4,7-triyl)triacetate (Gd.DOTA.AOC.DSA);
   wherein (i) phospholipid:(ii) lysolipid:(iii) phospholipid comprising a hydrophilic polymer:(iv) Gd.DOTA.AHX.DSA, or Gd.DOTA.AOC.DSA are present in the thermosensitive lipid nanoparticle in a molar ratio of about (i) 30-90:(ii) 2-15:(iii) 4-10:(iv) 20-30;
   wherein the thermosensitive lipid nanoparticle has improved thermal stability and a sharp temperature release profile at a temperature range of 39.0° C.-43.0° C.

2. The thermosensitive lipid nanoparticle according to claim 1, wherein the phospholipid comprises at least one phosphatidylcholine.

3. The thermosensitive lipid nanoparticle according to claim 2, wherein
   (a) the phospholipid comprises two or more different 1,2-di(C12-C20 saturated lipid)-snglycero-3-phosphocholines; or
   (b) the phospholipid comprises 1,2-dipalmitoyl-sn-glycero-3-phosphocholine (DPPC) or 1,2-distearoyl-sn-glycero-3-phosphocholine (DSPC); or
   (c) the phospholipid comprises 1,2-dipalmitoyl-sn-glycero-3-phosphocholine (DPPC) and 1,2-distearoyl-sn-glycero-3-phosphocholine (DSPC).

4. The thermosensitive lipid nanoparticle according to claim 1, wherein the lysolipid comprises a monoacylphosphatidylcholine which is one or more selected from the group consisting of monopalmitoylphosphatidylcholine (MPPC), monolaurylphosphatidylcholine (MLPC), monomyristoylphosphatidylcholine (MMPC) and monostearoylphosphatidylcholine (MSPC).

5. The thermosensitive lipid nanoparticle according to claim 1, wherein the phospholipid comprising the hydrophilic polymer (a) is a polyethylene glycol derivatized (PEGylated) lipid, or
(b) comprises a phospholipid which is one or more selected from the group consisting of a phosphatidylcholine, a phosphatidylethanolamine, a phosphatidylglycerol, a phosphatidylserine, a phosphatidic acid, a phosphatidylinositol, and a sphingolipid.

6. The thermosensitive lipid nanoparticle according to claim 5, wherein the phospholipid in the phospholipid comprising a hydrophilic polymer comprises a phosphatidylethanolamine which is one or more selected from the group consisting of polyethylene glycol (2000)-distearoylphosphatidylethanolamine ($PEG^{2000}$-DSPE) and polyethylene glycol (2000)-dipalmitoylphosphatidylethanolamine ($PEG^{2000}$-DPPE).

7. The thermosensitive lipid nanoparticle according to claim 1, wherein
(a) the lipid nanoparticle comprises about 5-8 mol % of $PEG^{2000}$-DSPE; or
(b) the lipid nanoparticle comprises a first phosphatidylcholine in an amount of 40-70 mol %, and a second phosphatidylcholine in an amount of about 0-10 mol %.

8. The thermosensitive lipid nanoparticle according to claim 1, further comprising
(a) at least one active pharmaceutical ingredient (API) selected from the group consisting of an anti-inflammatory agent; an anti-cancer and anti-tumour agent; an anti-microbial and antiviral agent; an anti-parasitic agent; a vasodilator; a bronchodilator, an anti-allergic and anti-asthmatic agent; a peptide; a protein; a glycoprotein; a lipoprotein; a carbohydrate; a receptor; a growth factor; a hormone and steroid; a neurotransmitter; an analgesic and anesthetic; a narcotic; a catalyst and enzyme; a vaccine; a genetic material; a nucleic acid; and a polynucleotide or an antibody, or
(b) an anti-cancer agent, an antibody or an antibiotic; or
(c) an anti-cancer agent selected from topotecan and doxorubicin.

9. The thermosensitive lipid nanoparticle according to claim 8, comprising DPPC:DSPC:MSPC:$PEG^{2000}$-DSPtE: Gd.DOTA.AHX.DSA:XL750.DSA or DPPC:DSPC:MSPC: $PEG^{2000}$-DSPtE: Gd.DOTA.AOC.DSA:XL750.DSA in a molar ratio of 54:5:5:6:30:0.05 and the API.

10. The thermosensitive lipid nanoparticle according to claim 8,
(a) further comprising a targeting agent, or
(b) further comprising a targeting agent wherein the targeting agent is a tumour targeting agent, or
(c) further comprising one or more imaging agents; wherein the further imaging agent is a Positron emission tomography (PET) imaging agent, Single-photon emission computed tomography (SPECT) imaging agent, or both PET and SPECT imaging agent.

11. A pharmaceutical composition comprising
(a) a therapeutic amount of the thermosensitive lipid nanoparticle according to claim 8 and a pharmaceutically acceptable carrier, wherein the therapeutic amount is effective for treatment of a human or animal body using hyperthermia or application of ultrasound; or
(b) a diagnostic amount of the thermosensitive lipid nanoparticle according to claim 1 and a pharmaceutically acceptable carrier, wherein the diagnostic amount is effective for diagnosis of a human or animal body using hyperthermia or application of ultrasound.

12. A method of treating or diagnosing a subject in need thereof, comprising hyperthermia, the application of ultrasound, or both, the method comprising:
(a) administering to the subject a pharmaceutical composition containing a therapeutic amount of the thermosensitive lipid nanoparticle according to claim 1 and a pharmaceutically acceptable carrier;
(b) monitoring the progress of, or detecting, the thermosensitive lipid nanoparticle or pharmaceutical composition to or in an area of interest using MRI, optical imaging, or both; and
(c) inducing heating or applying ultrasound to the area of interest.

13. The method according to claim 12, comprising generating hyperthermia by at least one method selected from laser heating, radiofrequency thermal ablation (RFA), microwave hyperthermia and focused ultrasound (FUS).

14. The method according to claim 12, wherein
(a) the hyperthermia is generated using focused ultrasound (FUS); or
(b) the hyperthermia is generated using continuous focused ultrasound (FUS), high frequency focused ultrasound (FUS) or both; or
(c) the method is effective for treating cancer; or
(d) the method is effective for treating rheumatoid arthritis.

15. The method of treating or diagnosing a subject in need thereof according to claim 12,
wherein a near infrared fluorescence (NIRF) imaging label comprises a near infrared fluorescence (NIRF) imaging agent is conjugated to the lipid.

16. The method according to claim 15, wherein
(a) the hyperthermia is generated by at least one method selected from laser heating, radiofrequency thermal ablation (RFA), microwave hyperthermia or focused ultrasound (FUS); or
(b) the hyperthermia is generated using continuous focused ultrasound, high frequency focused ultrasound (FUS), or both.

* * * * *